United States Patent
Tsuruda et al.

(10) Patent No.: US 11,865,123 B2
(45) Date of Patent: Jan. 9, 2024

(54) METHODS OF INHIBITING PATHOLOGICAL ANGIOGENESIS

(71) Applicant: Unity Biotechnology, Inc., South San Francisco, CA (US)

(72) Inventors: Pam Tsuruda, South San Francisco, CA (US); Jill Hopkins, South San Francisco, CA (US); Harry Sweigard, South San Francisco, CA (US); Yan Poon, South San Francisco, CA (US); Jamie Dananberg, South San Francisco, CA (US); Daniel Marquess, South San Francisco, CA (US); Nathaniel David, South San Francisco, CA (US)

(73) Assignee: Unity Biotechnology, Inc., South San Francisco, CA (US)

( * ) Notice: Subject to any disclaimer, the term of this patent is extended or adjusted under 35 U.S.C. 154(b) by 11 days.

(21) Appl. No.: 17/412,003

(22) Filed: Aug. 25, 2021

(65) Prior Publication Data

US 2022/0072015 A1 Mar. 10, 2022

Related U.S. Application Data

(60) Division of application No. 16/791,960, filed on Feb. 14, 2020, now Pat. No. 11,129,838, which is a division of application No. 16/160,840, filed on Oct. 15, 2018, now Pat. No. 10,588,916, which is a continuation of application No. PCT/US2018/046553, filed on Aug. 13, 2018.

(60) Provisional application No. 62/579,793, filed on Oct. 31, 2017.

(51) Int. Cl.
| | |
|---|---|
| *A61K 31/635* | (2006.01) |
| *A61P 27/02* | (2006.01) |
| *A61K 9/00* | (2006.01) |
| *A61K 47/26* | (2006.01) |
| *A61K 47/20* | (2006.01) |
| *A61K 47/10* | (2017.01) |

(52) U.S. Cl.
CPC .......... *A61K 31/635* (2013.01); *A61P 27/02* (2018.01); *A61K 9/0019* (2013.01); *A61K 9/0048* (2013.01); *A61K 47/10* (2013.01); *A61K 47/20* (2013.01); *A61K 47/26* (2013.01)

(58) Field of Classification Search
CPC ..... A61P 27/02; A61K 31/496; A61K 31/675; C07D 403/12; C07D 401/12
USPC ...................................................... 514/157
See application file for complete search history.

(56) References Cited

U.S. PATENT DOCUMENTS

| | | | |
|---|---|---|---|
| 6,228,873 B1 | 5/2001 | Brandt et al. | |
| 8,563,735 B2 | 10/2013 | Bruncko et al. | |
| 8,691,184 B2 | 4/2014 | Wang et al. | |
| 9,096,625 B2 | 8/2015 | Wang et al. | |
| 9,248,140 B2 | 2/2016 | Diebold et al. | |
| 9,849,128 B2 | 12/2017 | Laberge et al. | |
| 9,901,080 B2 | 2/2018 | Campisi et al. | |
| 9,968,076 B2 | 5/2018 | Kirkland et al. | |
| 10,010,546 B2 | 7/2018 | Laberge et al. | |
| 10,195,213 B2 | 2/2019 | David | |
| 2005/0282803 A1 | 12/2005 | Haley et al. | |
| 2012/0189539 A1 | 7/2012 | Wang et al. | |
| 2013/0225603 A1 | 8/2013 | Chavala et al. | |
| 2014/0199234 A1 | 7/2014 | Wang et al. | |
| 2016/0122758 A1 | 5/2016 | Krizhanovsky et al. | |
| 2016/0339019 A1 | 11/2016 | Laberge et al. | |
| 2017/0056421 A1 | 3/2017 | Zhou et al. | |
| 2017/0196858 A1 | 7/2017 | Laberge et al. | |
| 2017/0216286 A1 | 8/2017 | Kirkland et al. | |
| 2017/0266211 A1 | 9/2017 | David et al. | |
| 2018/0000816 A1 | 4/2018 | David et al. | |

FOREIGN PATENT DOCUMENTS

| | | |
|---|---|---|
| EP | 3441069 | 2/2019 |
| WO | WO2012103059 | 8/2012 |
| WO | WO2014174511 | 10/2014 |
| WO | WO2016024230 | 2/2016 |
| WO | WO2016127135 | 8/2016 |
| WO | WO2017008060 | 1/2017 |
| WO | WO2017101851 | 6/2017 |
| WO | WO201903311 | 2/2019 |

OTHER PUBLICATIONS

Baar et al., (2017) "Targeted Apoptosis of Senescent Cells Restores Tissue Homeastasis in Response to Chemotoxicity and Aging," cell, 169(1): 132-147.
Baker et al., (2016) "Naturally occurring p16Ink4a-positive cells shorten healthy lifespan," Nature, 530(7589): 184-189.

(Continued)

*Primary Examiner* — Kahsay Habte
(74) *Attorney, Agent, or Firm* — Bozicevic, Field & Francis LLP; Rudy J. Ng

(57) ABSTRACT

This invention is based on the discovery that many eye conditions associated with aging are mediated at least in part by cells bearing a senescent phenotype. Senescent cells accumulate with age, and express factors that contribute to the pathophysiology of age related conditions. The data show that in age-matched patients, the severity of age-related conditions correlates with the abundance of senescent cells, and that clearing senescent cells can help abrogate the condition. Small molecule drugs that remove senescent cells from affected tissue in the eye are provided that have special efficacy in treating ophthalmic conditions. They not only inhibit progression of the disease, they can also reverse some of the pathophysiology—such as neovascularization and vaso-obliteration—that lead to vision loss. These senolytic agents have an appropriate dose and specificity profile to be effective in the clinical management of previously intractable ophthalmic conditions.

6 Claims, 19 Drawing Sheets

(56) References Cited

OTHER PUBLICATIONS

Barakat et al., (2009) "VEGF inhibitors for the treatment of neovascular age-related macular degeneration," Expert Opinion on Investigational Drugs, 18, 1-2.
Bai et al., (2014) "BM-1197: A Novel and Specific Bcl-2/Bcl-xL Inhibitor Inducing Complete and Long-Lasting Tumor Regression In Vivo," PLOS ONE, 9(6): 1-13.
Blagosklonny (2013) "Selective anti-cancer agents as anti-aging drugs," Cancer Biology & Therapy 14(12): 1092-1097.
Braun et al., (2012) "Cellular Senescence Limits Regenerative Capacity and Allograft Survival," J Am Soc. Nephrol., 23(9): 1467-1473.
Campisi & Robert (2014) "Cell senescence, role in aging and age-related diseases," Interdiscip Top Gerontol, 39: 45-61.
Childs et al., (2017) "Senescent cells: an emerging target for diseases of ageing," Nat Rev Drug Discov., 16(10): 718-735.
Crespo-Garcia et al., (2021) Pathological angiogenesis in retinopathy engages cellular senescence and is amenable to therapeutic elimination via BCL-xL inhibition, Cell Metabolism, Article 33, 1-15.
Excerpt of file history of EP 18188799.3 (2019), pp. 1-17.
Excerpts from file history of U.S. Appl. No. 15/675,171 (2019), pp. 1-117.
Ferrara et al., (2010) "Analysis of Major Alleles Associated with Age-Related Macular Degeneration in Patients with Multifocal Choroiditis," Evidence-Based Ophthalmology, 11: 16-17.
Jeon et al., (2017) "Local clearance of senescent cells attenuates the development of post-traumatic osteoarthritis and creates a pro-regenerative environment," Nature for Medicine, 1-9.
Kirkland & Tchkonia (2015) "Clinical Strategies and Animal Models for Developing Senolytic Agents," Exp Gerontol, 68: 19-25.
Liton et al., (2005) "Cellular senescence in the glaucomatous outflow pathway," Experimental Gerontology, 40: 475-748.
Miller et al., (2004) "The association of prior cytomegalovirus infection with neovascular age-related macular degeneration," American Journal of Ophthalmology 138: 323-328.
Oubaha et al., (2016) "Senescence-associated secretory phenotype contributes to pathological angiogenesis in retinopathy" Sci. Transl. Med. 8: 1-16.
Yosef et al., (2016) "Directed Elimination of senescent cells by inhibition of BCL-W and BCL-XL," Nature Communications, Article 1-11.
Zhu et al (2017) "New agents that target senescent cells: the flavone, fisetin, and the BCL-XL inhibitors, A1331852 and A1155463," Aging, 9: 1-9.
EP18188799 Article 94(3) EPC Communication dated Jun. 28, 2019 pp. 1-4.
EP18188799 Article 94(3) EPC Communication dated Nov. 27, 2019 pp. 1-5.
EP18188799 Article 94(3) EPC Communication dated Aug. 3, 2020 pp. 1-4.
EP18188799 Article 94(3) EPC Communication dated Apr. 2, 2020 pp. 1-5.
EP18188799 Article 94(3) EPC Communication dated Feb. 8, 2021 pp. 1-4.
EP18188799 Search Report dated Dec. 12, 2018 pp. 1-8.
Acasigua GA et al. (2015) "BH3-mimetic small molecule inhibits the growth and recurrence of adenoid cystic carcinoma. Oral Oncol.," 51(9):839-47.

Normal

Diabetes

Sickle Cell

Vasculitis

METHODS OF INHIBITING PATHOLOGICAL ANGIOGENESIS

RELATED APPLICATIONS

This disclosure follows the filing of international patent application PCT/US2018/46553, filed Aug. 13, 2018, which claims the priority benefit of U.S. patent application Ser. No. 15/675,171, filed Aug. 11, 2017 (pending), and U.S. patent application 62/579,793, filed Oct. 31, 2017. Another previous disclosure is European patent application 18188799.3, filed Aug. 13, 2018. The aforelisted disclosures are hereby incorporated herein by reference in their entirety for all purposes.

BACKGROUND

The prevalence of adult vision impairment and blindness due to age-related eye disease is one of the largest challenges facing modern medicine.

According to the World Health Organization, three eye conditions have emerged as potential threats to the status of sight of people in middle-income and industrialized countries throughout the world. The increase in the prevalence of Type II diabetes has caused diabetic retinopathy to take top place on the WHO's priority list. Glaucoma, a disabling eye disease known for centuries, remains on the public health agenda due to difficulties in its early diagnosis and frequent necessity of life-long treatment. Age-related macular degeneration (AMD) ranks third among the global causes of visual impairment with a blindness prevalence of 8.7%. It is the primary cause of visual impairment in industrialized countries.

According to the National Eye Institute (NEI), in the U.S. population 2.1 million have age-related macular degeneration, 7.7 million have diabetic retinopathy, 2.7 million have glaucoma, and 24.4 million have cataracts. This represents a remarkable 26% of the American population over 40 years of age.

In spite of the prevalence of visual disability, and all the attention it receives in the medical research community, these disorders remain largely intractable. Many conditions have no available or disease-modifying therapeutic alternatives. With few exceptions, most drugs currently approved for treating these disorders are directed at late-stage pathophysiology or the relief of symptoms, rather than addressing the factors that initiate and/or maintain the disease.

Currently available modes of therapy include inhibitors of vascular endothelial growth factor (VEGF) agents for the treatment of VEGF-associated eye disease (for example, wet AMD, diabetic eye disease), vitamins and anti-oxidants for dry AMD, and agents that lower intraocular pressure for glaucoma. Laser treatments are available to treat some conditions: for example, retinal photocoagulation for retinal edema or neovascularization secondary to diabetes, vein occlusion, and choroidal neovascularization; and laser trabeculoplasty to address elevated intra-ocular pressure resistant to medical therapy. For many ocular disorders including dry AMD, there are no currently approved therapeutic agents. A Phase 3 clinical trial for a humanized antibody designed for treatment of geographic atrophy in dry AMD (lampalizumab) recently failed to meet its primary endpoint of preventing atrophy progression. Even for eye diseases where therapeutic agents are available, the treatment regimens are often burdensome and have limited long term efficacy.

The invention provided here creates a new paradigm for the treatment of eye disease through the elimination of senescent cells implicated in the pathophysiology of disorders of the visual system. The disclosure that follows outlines its implementation and use, and describes many of the ensuing benefits.

SUMMARY

This invention is based on the discovery that many eye conditions associated with aging are mediated at least in part by cells bearing a senescent phenotype. Senescent cells accumulate with age, and express factors that contribute to the pathophysiology of age related conditions. The data show that in age-matched patients, the severity of age-related conditions correlates with the abundance of senescent cells, and that clearing senescent cells can help abrogate the condition.

Small molecule drugs that remove senescent cells from affected tissue in the eye are provided as part of this invention that have special efficacy in treating ophthalmic conditions. They not only inhibit progression of the disease, they can also reverse some of the pathophysiology—such as neovascularization and vaso-obliteration—that lead to vision loss. These senolytic agents have an appropriate dose and specificity profile to be effective in the clinical management of previously intractable ophthalmic conditions.

In general terms, this invention provides technologies for preventing or treating an ophthalmic condition in a subject by removing senescent cells in or around an eye of the subject so that progression of the condition is delayed or at least one sign or symptom of the disease is decreased in severity.

For purposes of this disclosure, ophthalmic diseases are classified according to six general types of pathophysiology: an ischemic or vascular condition; a degenerative condition; a genetic condition; a bacterial, fungal, or virus infection; an inflammatory condition; or an iatrogenic condition. The underlying pathophysiology is instructive in the implementation of a senolytic strategy to treat each disease. Classification of ophthalmic diseases within these types is provided in the disclosure that follows.

Included in the invention are methods of treatment, unit doses, and dedicated uses of particular inhibitors and senolytic agents. Effective agents that can be used in the context of this invention to remove senescent cells and treat ophthalmic conditions include compounds having the following formula, or a phosphorylated form thereof:

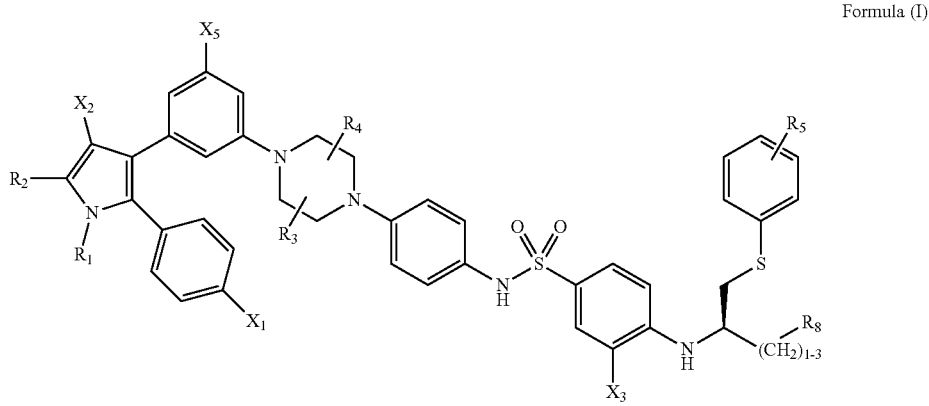

Formula (I)

wherein:
R$_1$ and R$_2$ are independently C$_1$ to C$_4$ alkyl
R$_3$, R$_4$ and R$_5$ are independently —H or —CH$_3$;
R$_8$ is —OH or —N(R$_6$)(R$_7$), wherein R$_6$ and R$_7$ are independently alkyl or heteroalkyl, and are optionally cyclized;
X$_1$ is —F, —Cl, —Br, or —OCH$_3$;
X$_2$ is —SO$_2$R' or —CO$_2$R', where R' is —H, —CH$_3$, or —CH$_2$CH$_3$;
X$_3$ is —SO$_2$CF$_3$; —SO$_2$CH$_3$; or —NO$_2$; and
X$_5$ is —F, —Br, —Cl, —H, or —OCH$_3$.

In some implementations, X$_3$ is —SO$_2$CF$_3$ or —NO$_2$, and R$_8$ is —N(R$_6$)(R$_7$), wherein R$_6$ and R$_7$ are independently alkyl or heteroalkyl, and are optionally cyclized.

Depending on how the technology is implemented, besides generally improving symptomatology or preventing advancement of a particular ophthalmic condition, the technology may have one or more of the following effects in any combination:
  reducing the number of p16 positive senescent cells in or around an eye of the subject;
  inhibiting or reversing neovascularization in an eye of the subject;
  inhibiting or reversing vaso-obliteration in an eye of the subject; and
  inhibiting or reversing increased intra-ocular pressure (IOP) in an eye of the subject.

Also provided as part of this invention are novel screening methods. One such method comprises selecting a test agent as a possible pharmaceutical compound for treating glaucoma by contacting trabecular meshwork (TM) cells in culture or in a tissue of a non-human test subject, and determining whether the test agent reduces the number of senescent cells in the culture or tissue. Another such screening method comprises administering a test agent to an eye of a non-human test subject, and determining whether the test agent inhibits or reverses neovascularization or vaso-obliteration caused in the course of an animal disease model.

Other features of the technology of the invention are provided in the sections below and in the appended claims.

DRAWINGS

FIG. 1A is a flow chart that shows the pathophysiologic interactions in the eye that result from ischemia. FIG. 1B is a flow chart that shows the multifactorial pathophysiology of glaucoma, leading to retinal ganglion cell (RGC) cell death. FIG. 1C is a flow chart that shows the pathophysiologic cascade in age related macular degeneration. FIG. 1D is a flow chart that shows events leading to cell degeneration and cell death in Leber's Hereditary Optic Neuropathy.

FIG. 2A comprises images of histopathology that show retinal cell loss in stages of Retinitis Pigmentosa. FIGS. 2B, 2C, 2D, and 2E are fluorescein angiograms of a normal retina and retinal non-perfusion and neovascularization from diabetes, sickle cell disease and inflammatory vasculitis, respectively.

FIGS. 3A and 3B show nine particular compounds selected from a library on the basis of binding to Bcl-2 or Bcl-xL.

FIGS. 4A, 4B, and 4C show quantitative binding affinity of the nine compounds to Bcl isoforms Bcl-xL, Bcl-2, and Bcl-w, respectively. Each of the compounds for which the data is shown are identified according to their designated BM number.

FIGS. 5A, 5B, and 5C shows how effective compounds were compared structurally to determine what substructures contribute to the desired properties of the compounds.

Figure 8:
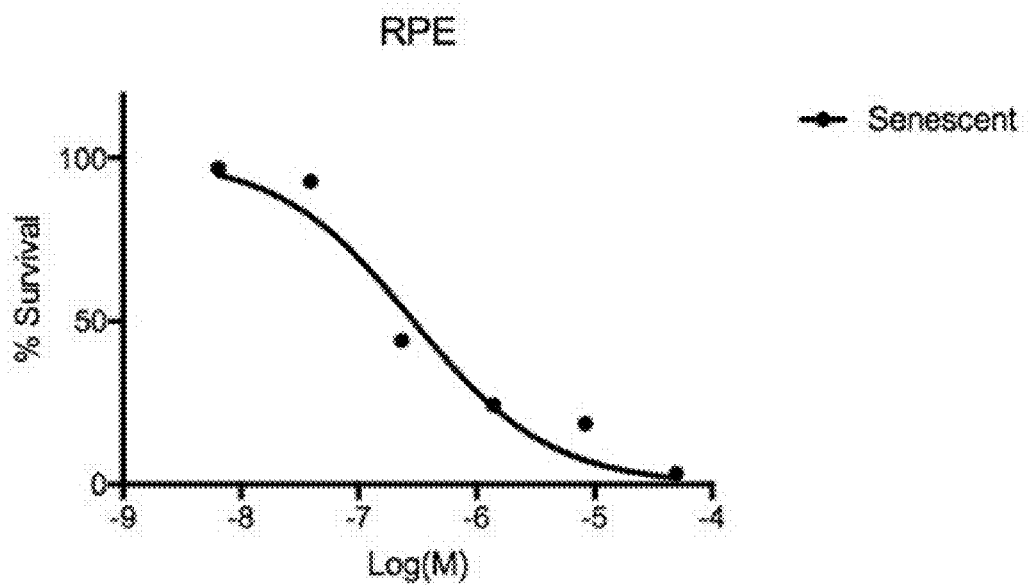

FIG. 8 is a concentration-response curve for senescent retinal pigment epithelium (RPE) cells and control cells treated in vivo with a senolytic agent. The agent has a much higher potency (lower LD$_{50}$) for the senescent cells than for normal proliferating RPE cells. It has a selectivity index for senescent RPE cells compared with non-senescent RPE cells of between 10 and 100.

Figure 9A:
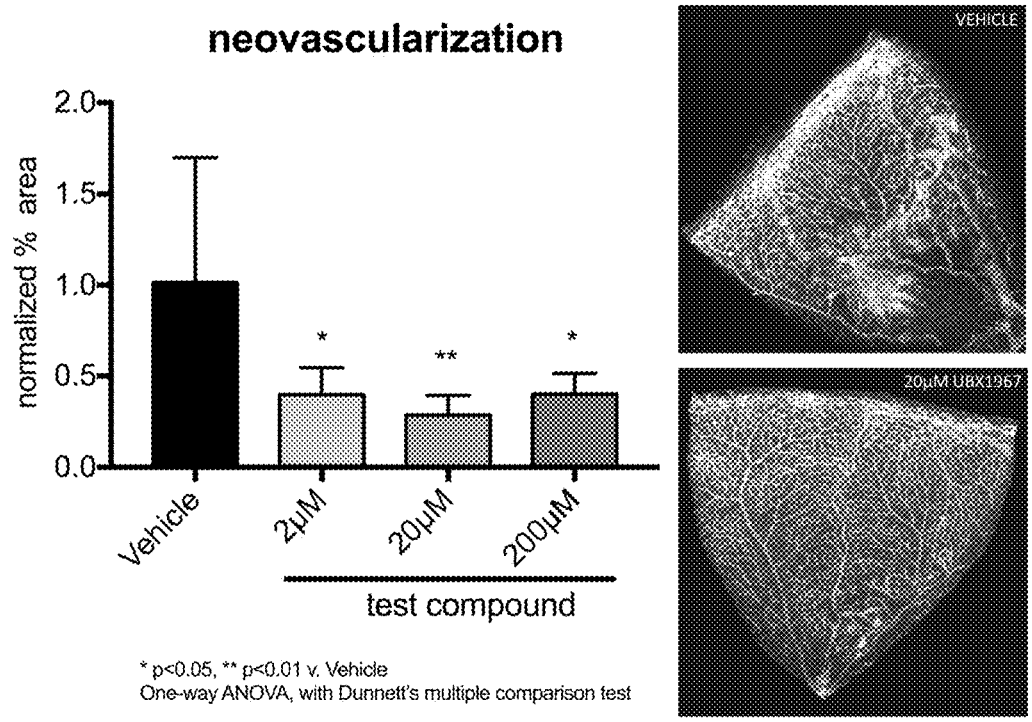
Figure 9B:
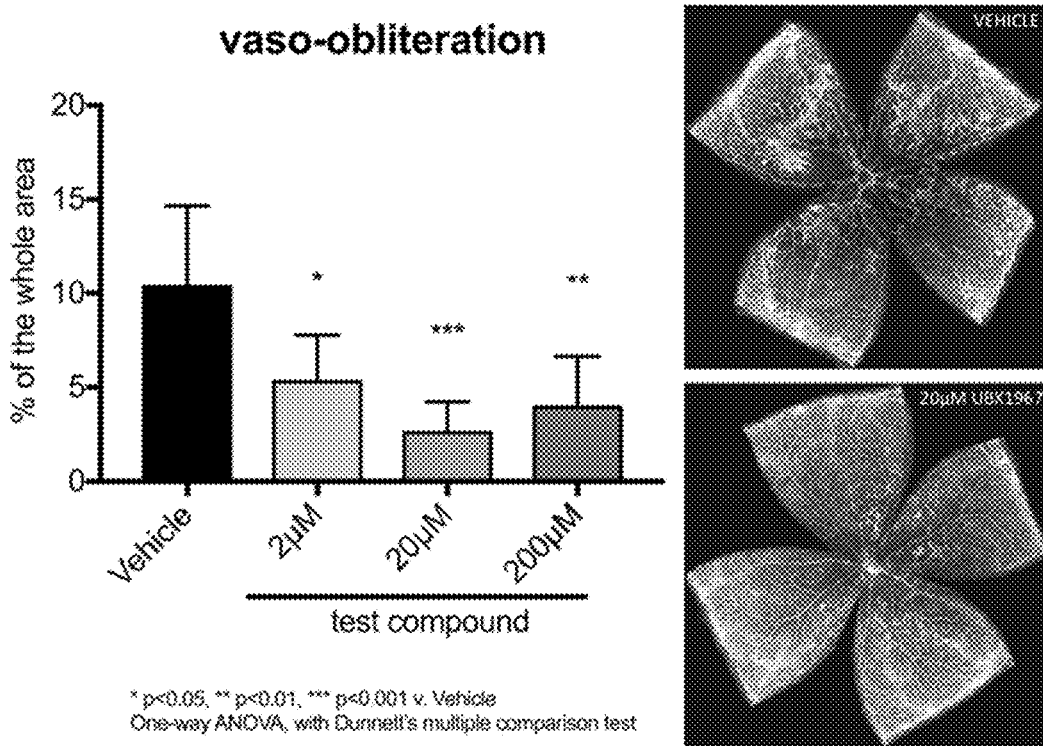

FIGS. 9A and 9B show reversal of both neovascularization and vaso-obliteration in the mouse oxygen-induced retinopathy (OIR) model when intravitreally administered with the senolytic agent UBX1967.

FIGS. 10A, 10B, 10C, and 10D show decreased expression levels at the RNA transcript level of senescence-associated markers, following treatment with UBX1967.

Figure 11A:
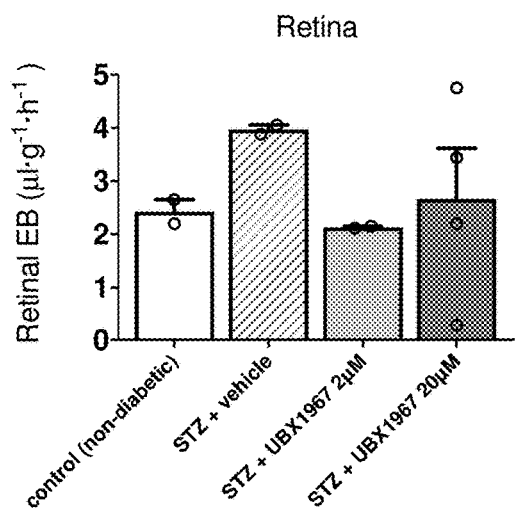
Figure 11B:
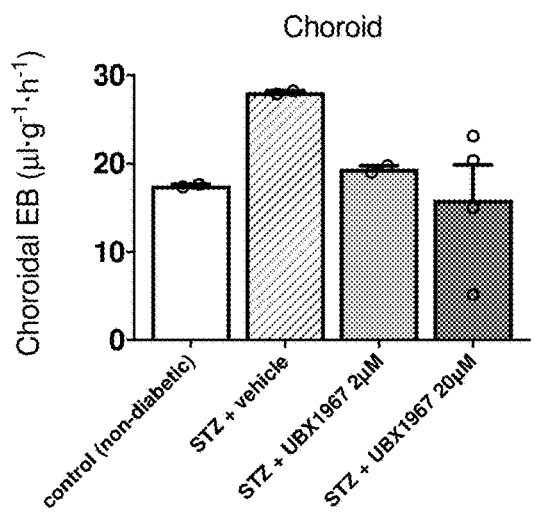

FIGS. 11A and 11B are taken from the streptozotocin (STZ) model for diabetic retinopathy. STZ-induced vascular leakage is attenuated with the intravitreal administration of UBX1967.

Figure 12A:
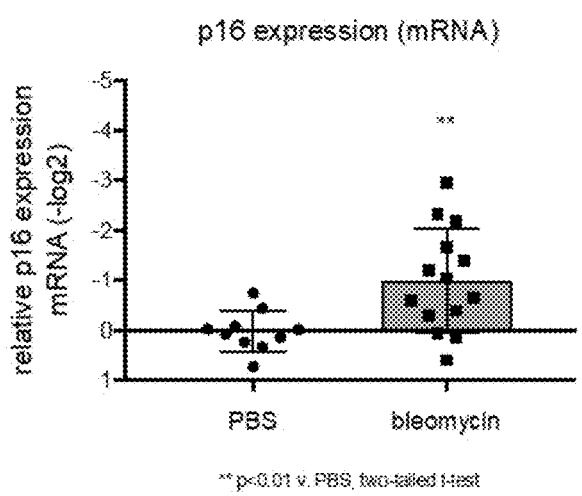
Figure 12B:
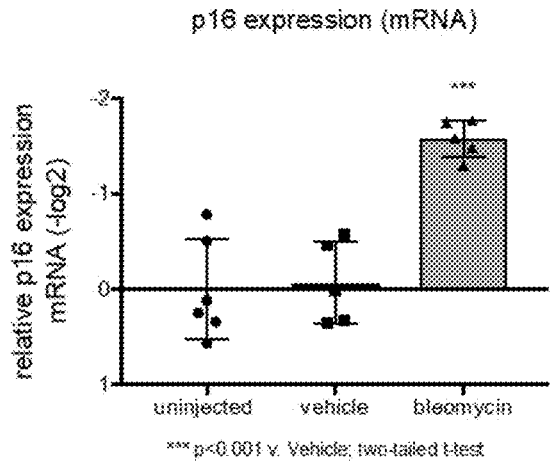

FIGS. 12A and 12B show immunohistochemistry staining for p16 (a marker for senescent cells) in tissue taken from a patient with primary open angle glaucoma (POAG). p16 positive cells are prominent in the trabecular meshwork (TM).

Figure 13A:
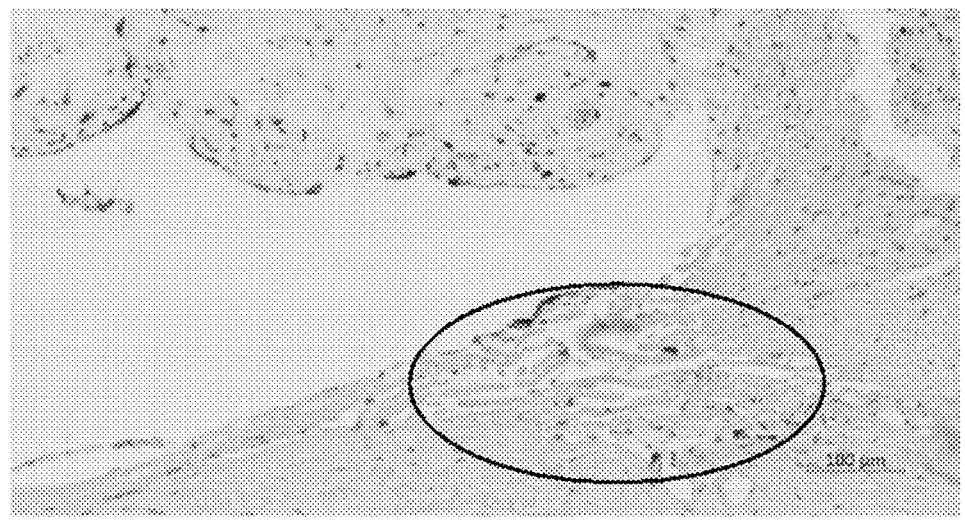
Figure 13B:
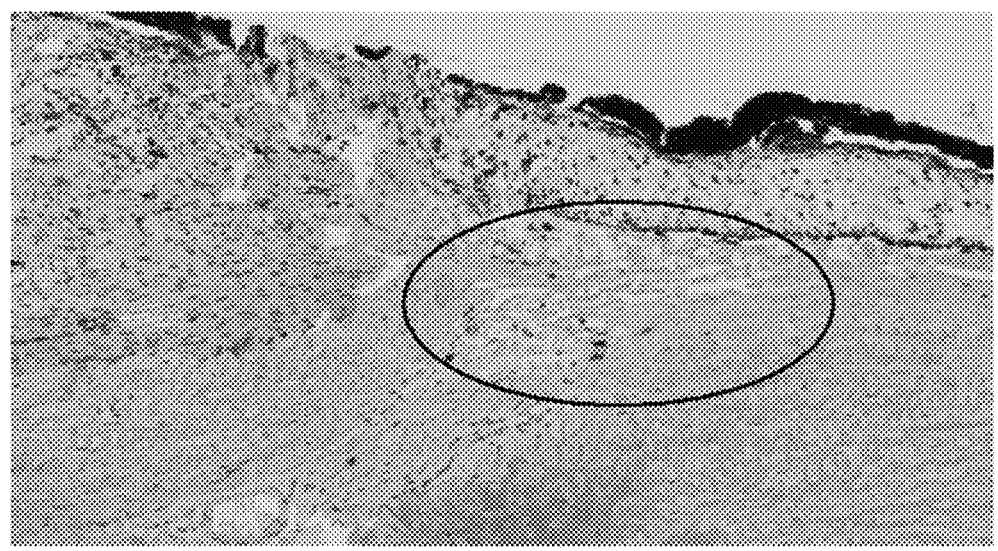

FIGS. 13A and 13B show the expression of p16 in human eye tissue obtained from donors diagnosed with primary open angle glaucoma (POAG).

Figure 14A:
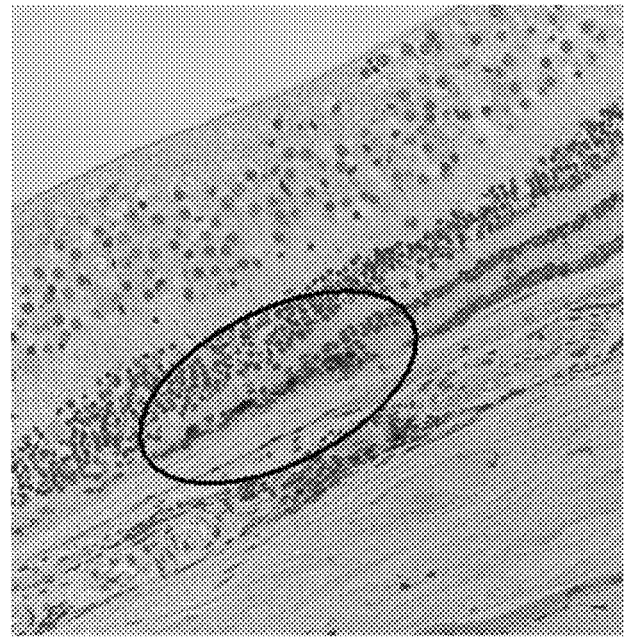
Figure 14B:
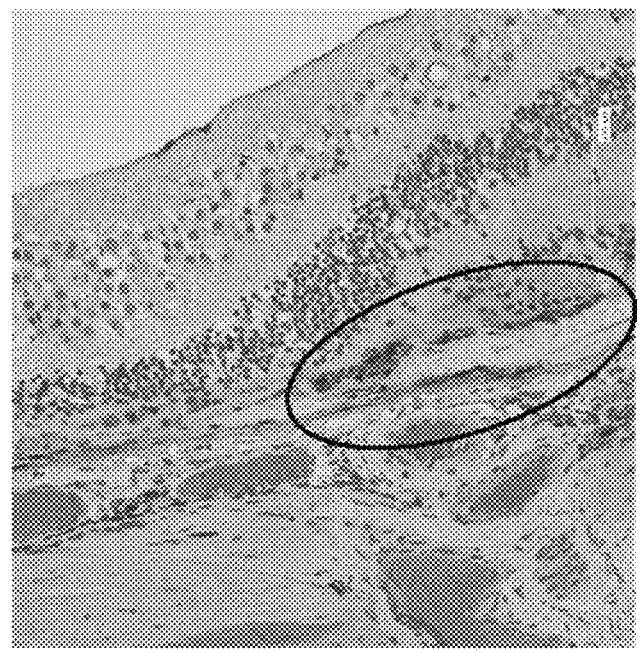

FIGS. 14A and 14B show immunohistochemistry staining for p16 in human retinal tissue of a patient with age-related macular degeneration (AMD).

DETAILED DESCRIPTION

Overview

It is a premise of this disclosure that many or most ophthalmic conditions that are age-related, or are associated with cellular defects that lead to an accelerated aging phenotype, are caused or mediated at least in part by senescent cells, which accumulate with age and with deleterious impact on ophthalmic tissues. Senescent cells are typically cells that no longer have replicative capacity, but remain in the tissue of origin, eliciting a senescence-associated secretory phenotype (SASP). Senescent cells are thought to derive from proliferative cells of a variety of tissue types, including cells that reside in and around the eye. SASP factors include molecules that are angiogenic, inflammatory, fibrotic, and extracellular matrix modifying molecules (Acosta et al., 2013). Some factors implicated in ocular pathologies are part of the constellation of factors produced by senescent cells. For this reason, elimination or control of senescent cells provides a means by which to treat eye disease, not only through the elimination of senescent cells but also through reduction of their associated SASP factors and impact on surrounding cells.

Different eye conditions present in the clinic with different signs and symptoms, and have different types of pathophysiologic mechanisms. The heterogeneity of eye conditions is consistent with the putative role of senescent cells in the disease pathology, because senescent cells may be from different cell lineages, induced by different stressors, reside in different ocular tissues, and interact with surrounding cells in a different fashion. Nevertheless, senescent cells in the various tissues of the eye have a related secretory phenotype that contributes to disorders throughout the visual system. The specific clearance of senescent cells from tissue is referred to in this disclosure as senolysis. Small molecule compounds capable of senolysis are referred to as senolytic agents, and clear senescent cells irrespective of mechanism of senescence induction, SASP profile or cell lineage.

By way of illustration, we have found that inhibitors of the Bcl family of proteins trigger apoptosis in senescent cells derived from a cell type known to reside in the back of the eye and are cells implicated in retinal disease such as AMD—and also trigger apoptosis in senescent cells derived from a cell type known to reside in the anterior compartment of the eye and are cells implicated in diseases such as glaucoma.

Discoveries that Change the Current Paradigm for Drug Development

Besides a new understanding of the general role of senescent cells in mediating ophthalmic conditions, other discoveries are described in this disclosure that open new avenues for drug development.

One is the discovery that senescent cells are abundant in the trabecular meshwork of patients with glaucoma, and in corresponding animal models. Intraocular pressure increase is caused by either an overproduction of aqueous humor primarily in the ciliary body, or a decrease in outflow of aqueous fluid primarily through the trabecular meshwork The data presented here are consistent with the idea that at least part of the pathophysiology underlying the disease is impaired drainage of intraocular fluid through the trabecular meshwork and down the canal of Schlemm and the episcleral veins into the orbital venous system. Targeting senolytic drugs to cells in the trabecular network is an important new avenue for pharmaceutical development: both as monotherapies, and in combination with drugs that work by regulating fluid production.

Another discovery is that removing senescent cells from the back of the eye in diseases such as diabetic retinopathy doesn't just inhibit disease progression: it actually reverses some of the pathophysiology that leads to loss of vision, including neovascularization and vaso-obliteration. To our knowledge, there is no current therapy (either in the clinic or in development) that is able to reverse the course of retinopathy to this extent. The objective of therapy for ophthalmic conditions can now be more ambitious—giving renewed hope to patients with these diseases for an improved quality of life.

Advantages of Treating Ophthalmic Conditions by Clearing Senescent Cells

The role of senescent cells in promoting or mediating a variety of ophthalmic conditions provides an approach to treatment with a number of advantages for the managing clinician.

Since senescent cells are non-proliferative, eliminating senescent cells has the potential for a clinically beneficial effect that persists for an extended time between episodes of treatment. Features of the condition mediated by senescent cells resolve at least until senescent cells re-accumulate. Since senescent cells are likely to accumulate slowly (given the nature of age related diseases is to evolve over a period of many years), the effects of a single treatment or treatment cycle may last for weeks, months, or years.

To the extent that senescent cells exacerbate other types of pathology such as inflammation or tissue breakdown, the long-lasting effect of senolysis provides a window in which such pathology is held at bay, potentially giving the tissue a chance for repair. This means that senescent cell medicine has the potential not just to halt progression of ophthalmic conditions, but allow some degree of reversal of the disease and its symptoms for the benefit of the patient.

Since senescent cells in different parts of the eye respond to the same senolytic agents, several different eye diseases can be treated in the same patient at the same time. For example, a patient may present to the clinician with several disease processes already under way: such as glaucoma and macular degeneration. It may be possible to administer a single senolytic agent in a treatment protocol that addresses the disease and its symptoms of each of the multiple conditions. Beyond the convenience of this approach, it has the added benefit of lowering the risk of side effects that may result from multiple drugs being given in combination to treat each of the conditions individually. Furthermore, it is possible that factors elicited by cells in one part of the eye may impact other parts of the eye such that treating senescence to two locations may have a beneficial effect on both diseases.

By addressing the early pathology in a disease, senolytic medicine can be an important adjunct to other types of therapy that are administered to treat later stage pathology, or to relieve the symptoms that result from the condition. The two modes of therapy potentially work synergistically or additively to reduce the burden, frequency and side effects of either mode administered separately.

Classification of Eye Disease According to Underlying Pathophysiology

As a guide to treating ophthalmic conditions in accordance with this invention, the conditions can be classified according to the primary underlying pathophysiology. Conditions that fall within the same classification are amenable to applying senolytic medicine with the same principles and with similar objectives.

Ophthalmic conditions suitable for treatment are discussed in more detail below, within the following classifications:

TYPE 1: Ischemic or vascular conditions: result from a restriction in blood supply to tissues, causing a deficiency of oxygen and/or essential nutrients needed for cellular metabolism to keep tissue functional.

TYPE 2: Degenerative conditions: characterized by a progressive deterioration in quality, function, or structure of a tissue or organ, leading to progressive visual impairment.

TYPE 3: Genetic conditions: caused by a mutation, deletion, or insertion in an individual's DNA sequence.

TYPE 4: Infectious conditions, caused by pathogenic microorganisms, such as bacteria, viruses, parasites or fungi; the diseases can be spread, directly or indirectly, from one person to another.

TYPE 5: Inflammatory conditions characterized by a localized response elicited by injury, foreign object, or destruction of tissues, which serves to destroy, dilute, or wall off both the injurious agent and the injured tissue via the production of pro-inflammatory mediators and recruitment of immune system cells.

TYPE 6: Iatrogenic conditions, defined as disease that is the result of diagnostic and therapeutic procedures undertaken on a patient.

This classification is provided to assist the reader in understanding and applying the invention to a particular patient, and is not meant to limit application of this technology. Certain conditions may invoke several of these categories: for example, an inflammatory process may contribute to pathological processes having other underlying causes. Similarly, the SASP may trigger additional pathologic processes regardless of the primary insult.

Treatment Design

Senescent cells accumulate with age, which is why conditions mediated by senescent cells occur more frequently in older adults. In addition, different types of stress on ocular tissues may promote the emergence of senescent cells and the phenotype they express. Cell stressors include oxidative stress, metabolic stress, DNA damage (for example, as a result of environmental ultraviolet light exposure or genetic disorder), oncogene activation, and telomere shortening (resulting, for example, from hyperproliferation). Ocular tissue subject to such stressors may have a higher prevalence of senescent cells, which in turn may lead to presentation of certain eye diseases at an earlier age, or in a more severe form. An inheritable susceptibility to certain eye diseases suggests that the accumulation of disease-mediating senescent cells may directly or indirectly be influenced by genetic components, which can lead to earlier presentation.

To treat a particular ophthalmic condition with a senolytic agent according to this invention, the therapeutic regimen will depend on the location of the senescent cells, and the pathophysiology of the disease.

With respect to location, disorders of the visual system are broadly classified as anterior and posterior. An anterior ocular condition is a disease, ailment or condition that affects or involves an anterior ocular region or site, such as periocular muscle, eyelid or eye tissue or fluid which is located anterior to the posterior wall of the lens capsule or ciliary muscles. A posterior ocular condition is a disease, ailment or condition which primarily affects or involves a posterior ocular region or site such as choroid, ciliary body, vitreous, vitreous chamber, retina, retinal pigment epithelium, Bruch's membrane, optic nerve (i.e. the optic disc), visual pathway and blood vessels and nerves which vascularize or innervate a posterior ocular region or site.

With respect to pathophysiology, senescent cells and SASP production can contribute to ongoing cell dysfunction and degeneration/death. Senescent cells and their associated SASP factors can mediate the associated contributions to ongoing cell dysfunction, cell loss, and disease progression via blockage of the angiogenic, inflammatory, fibrotic, and extracellular matrix-modifying proteins present in the pathophysiology.

Thus, elimination or reduction in the number of senescent cells in or around the site of the pathology removes at least one of the causes or mediators of the condition, as it is manifested in the clinic. The senolytic agent is formulated and administered in such a way that it contacts senescent cells in or around the site of the pathology, clearing them and/or inhibiting their activity to an extent that halts progression of the condition and/or signs and symptoms of the condition are relieved.

Different conditions mediated by senescent cells in about the same location and/or with a similar underlying pathology will often be treated in the same way. For example, a senolytic agent can be administered by local topical administration to the site affected in disorders of the anterior segment e.g., to the conjunctiva and/or cornea, for example using eye drops, ointment, or via application of a contact lens. Intraocular injection, either intracameral or intravitreal can be administered for disorders of both the anterior and posterior segments.

Diagnosis and Monitoring of Disorders of the Visual System:

The approach to the diagnosis and monitoring of all ocular conditions and diseases, and evaluation of therapeutic effects, is facilitated by the widespread availability of a standard battery of tests of ocular structure and function. These tests can evaluate individual layers of the eye extending from the lids and anterior segment to the vitreous and all retinal cell layers, the optic nerve and the visual cortex.

Standardized ophthalmic examination includes a detailed slit lamp biomicroscopic evaluation which allows evaluation of the lids, ocular adnexa, lashes, corneal surface, anterior chamber, pupils, lens, vitreous cavity and central retinal anatomy including the optic nerve and macula. Gonioscopy allows detailed examination of the anterior chamber angle, important in the diagnosis and monitoring of all forms of glaucoma. Indirect ophthalmoscopy allows for evaluation of the retinal periphery, important in the monitoring of vitreous and peripheral retinal disorders.

Ancillary testing is also widely used in the diagnosis and monitoring of therapeutic response in all disorders of the visual system and these tests include the following:

Functional tests of visual acuity (including best corrected acuity, contrast acuity, and low luminance acuity), color vision (including Ishihara and Farnsworth Munsell tests) and visual field evaluation (including Humphrey automated perimetry and microperimetry), tear production (Schirmer test), and tonometry to measure intraocular pressure (IOP). These are used in conjunction with structural tests including anterior and posterior segment photographs, corneal pachymetry, ultrasound, ultrasound biomicroscopy, optical coherence tomography (OCT), intravenous fluorescein angiography (IVFA), and fundus autofluorescence (FAF). Imaging such as computerized tomography (CT) or magnetic resonance imaging (MRI) scans are utilized to evaluate ocular, periocular and orbital structures, and the intracranial portion of the optic nerve, visual pathway and visual cortex in the brain. These tests allow visualization of structural integrity and thickness of the layers of the eye and surrounding structures, and assessment of blood flow and circulation.

Advanced functional testing of the retina, optic nerve and visual pathway/cortex is also used, including electrophysiologic tests such as full field and multifocal electroretinography, visual evoked potentials and microperimetry to diagnose and monitor disease progression and impact of therapy (Mengini and Duncan. 2014). While currently available only in research settings, other imaging technologies may become important adjuncts in the diagnosis and treatment of disease of the eye, including those due to senescence, such as the use of adaptive optics and optical coherence angiography.

Clinical examination, structural and functional measurements and correlations can be obtained in both animal models and the clinical setting and are applicable to the conditions and diseases of the visual system outlined in this application. The battery of tests as outlined above is part of the diagnosis, evaluation and response to treatment for these conditions.

As examples, retinal non-perfusion and neovascularization seen secondary to retinal ischemia produced by a range of different etiologic factors (e.g. diabetic retinopathy, vascular occlusive disease due to atherosclerotic or inflammatory causes, retinopathy of prematurity and genetic vascular disorders such as Sickle Cell retinopathy) can be structurally evaluated by IVFA and OCT to both diagnose and monitor response to a senolytic. Glaucomatous optic neuropathy with loss of retinal ganglion cells and visual field function that are the result of optic nerve susceptibility to increased IOP stemming from a host of causes (for example, remodeling of trabecular meshwork, primary open angle glaucoma (POAG), pseudoexfoliation, pigmentary dispersion, steroid treatment, trauma) can be diagnosed and monitored by OCT and visual field testing. The role of senescent cells as identified by molecular markers such as p16 in trabecular meshwork tissue of glaucoma patients (Example 5) and in retinal tissue in donor eyes with AMD (Example 6), and the presence of SASP factors known to be implicated in various stages of these diseases, highlight the potential impact of senolytic medicine on these conditions.

A consequence of this invention is that regardless of the exact means by which senescent cells accumulate and subsequently express SASP, senolytic therapy can have a beneficial impact on ocular disease features through the restoration of homeostasis in the cellular milieu. This results in disease modification via a change in the disease course and outcome.

Comparison of Senolytic Medicine with Currently Available Therapy

Therapies that are currently in clinical use are limited in their ability to achieve disease modification or potential reversal of pathology. The standard of care for the most prevalent ocular diseases (glaucoma and retinal and choroidal vascular disease) are topical drops to lower intraocular pressure (IOP) in glaucoma, intra-ocular injection of anti-VEGF agents for retinal and choroidal neovascular disease, and laser photocoagulation for both IOP control (Stein and Challa, 2007) and vitreo-retinal disorders (AAO Retina/Vitreous Panel, 2014).

Topical agents that lower intraocular pressure (IOP) and therapies targeting VEGF-related eye diseases, are burdened by a frequent administration schedule that must be adhered to in order to maximize efficacy. Even when administered optimally, anti-VEGF therapies are associated with a significant rate of incomplete response, disease recurrence, and ongoing progression of non-VEGF mediated aspects of the ocular disease (for example atrophy of the macula in treated wet AMD (Bhisitkhul, 2015). These same issues are a concern for IOP lowering agents used in glaucoma, which must be administered at least daily to lower IOP, and have been associated with ongoing glaucomatous disease progression even when used appropriately and associated with decreased IOP (Levin, 2005).

Laser photocoagulation has been another mainstay of ocular therapy used across a wide range of ocular diseases, over which senolytic administration can have many advantages. Although clinically effective, retinal laser photocoagulation leads to collateral damage and side effects including reduced night vision, macular and peripheral scotomata with decrease in central and peripheral vision, exacerbation of macular edema and disruption of the retinal anatomy through scarring (Kozak and Luttrul, 2015). In its application to the trabecular meshwork to lower IOP, laser therapy is associated with IOP spikes, peripheral anterior synechiae formation, need for additional laser or surgical procedures, and no reduction in the need for IOP-lowering drops following the procedure (Damji et al., 2006).

Removal of senescent cells and the associated SASP with senolytic therapy can positively impact disease course via the modulation of multiple disease-mediating factors including inflammatory, angiogenic and extracellular matrix-modifying aspects of the disease. With limited or no damage or destruction to healthy cells required to maintain visual function, and an infrequent dosing schedule with prolonged therapeutic effect this invention represents a major advance over currently available therapies that do not specifically target senescent cells or the multiple factors associated with the SASP, thus limiting their ability to modify multiple aspects of disease pathophysiology.

As an example, the elimination of senescent cells in the setting of ischemia can impact visual function by allowing functioning retinal ganglion cells to thrive in a healthier local environment, free of the SASP associated detrimental inflammatory, angiogenic and extracellular matrix-modifying factors. This can be monitored structurally by optical coherence tomography (OCT) measurements of retinal thickness, and functionally by electrophysiology testing (VEP and ERG) that can isolate function of the retinal ganglion cell layer. Automated perimetry can also be used to evaluate peripheral visual field function in patients.

Figure 2A:
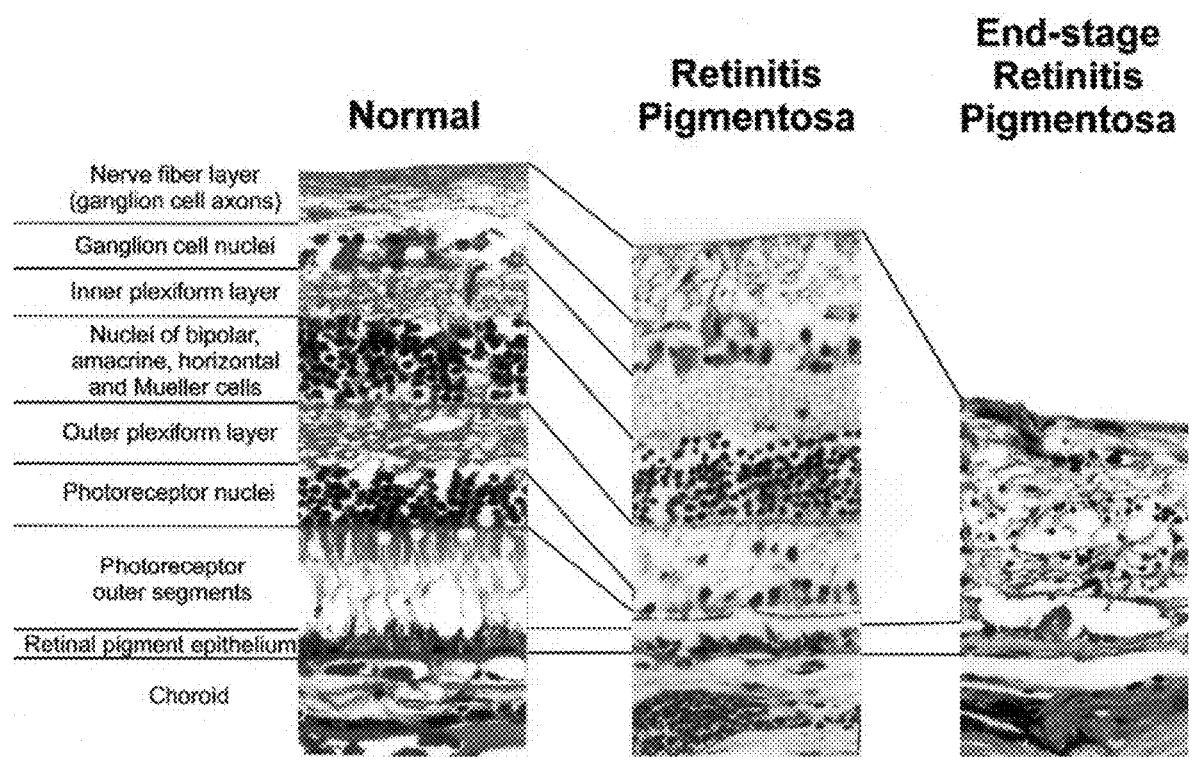
Figure 2B:
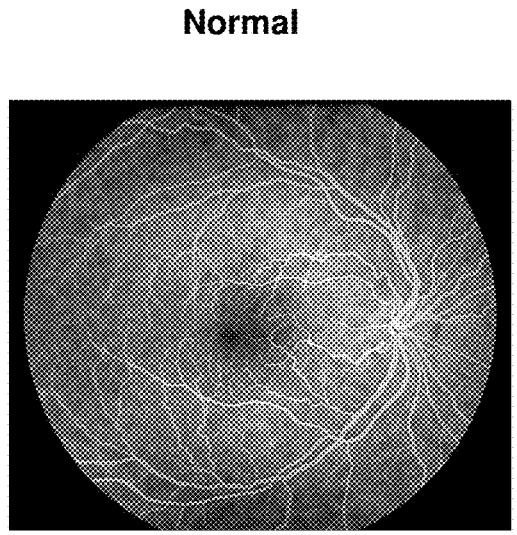
Figure 2C:
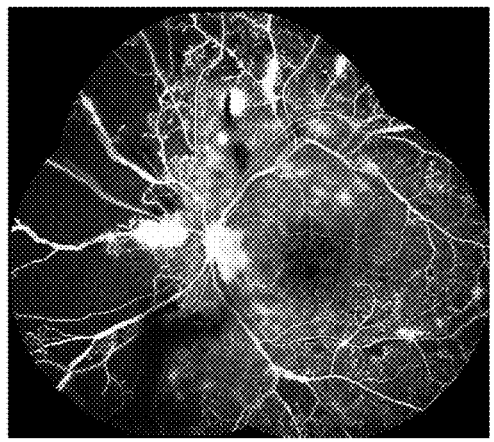
Figure 2D:
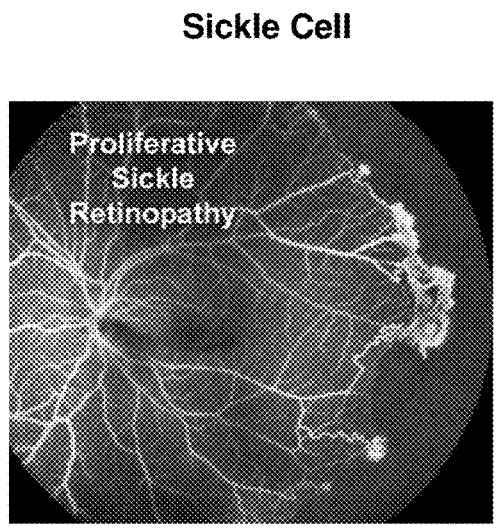
Figure 2E:
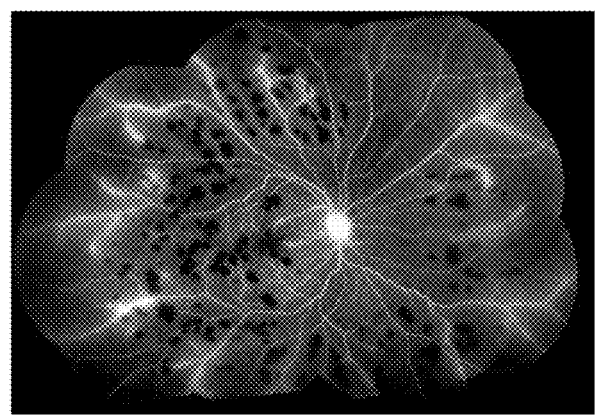

Similarly, in the setting of vaso-obliterative disease and neovascularization, the removal of senescent cells and SASP can potentially ameliorate ongoing associated cell damage and allow for re-perfusion of the affected vascular beds and decreased neovascular drive. The similarity of the ischemic phenotype (vaso-obliteration and neovascularization) regardless of etiology can be evaluated, and structural and functional response to therapy monitored by IVFA, OCT, and ERG. FIG. 2B (Image from Carver College of Medicine, University of Iowa website, sourced Oct. 30, 2017), FIG. 2C (Image from Retina Gallery website, sourced Oct. 30, 2017), FIG. 2D (Image from Retina Vitreous Associates of Florida website, sourced Oct. 30, 2017), and FIG. 2E (Image from Retina Gallery website, sourced Oct. 30, 2017) demonstrate fluorescein angiographic examples of a normal retina (FIG. 2B) and retinal non-perfusion and neovascularization from diabetes (FIG. 2C), sickle cell disease (FIG. 2D) and inflammatory vasculitis (FIG. 2E). Response to senolytic therapy can be monitored with intravenous fluorescein angiography (IVFA) and OCT. Factors known to be involved in the SASP of senescent cells may be measured directly in ocular fluids, including tears, aqueous humor and vitreous humor.

The impact of senolytic medicine on the treatment of eye disease incorporates three main concepts. First, once senescent cells are deleted, it is expected that the associated SASP factors derived from senescent cells will also be greatly diminished. In the absence of these inflammatory, angiogenic, and fibrotic proteins and extra-cellular matrix modifying enzymes, it is postulated that many or most of the symptoms of the ocular diseases described herein can be greatly impacted. Importantly, after senescent cells are deleted, it is possible that surrounding cells can restore some functional capacity. This represents a major pathophysiologic advance over currently available treatments for ocular disease. The impact of the senolytic agent and restoration of function can be monitored clinically with structural and functional testing such as outlined above.

Second, depending on the circumstances, a senolytic agent can be delivered as a single administration. If retreatments are necessary, the time between doses is considerably extended. As macular degeneration, glaucoma, and vascular and hereditary retinopathies are characterized by slow degradation of the retina over a period of many years, re-accumulation of senescent cells takes a substantial period of time. Further therapy may not be needed for several years. This represents a major improvement over for example the dosing schedule of existing anti-VEGF therapies which require once monthly to every other month administration and are associated with suboptimal visual and anatomic outcomes if delivered on a less frequent schedule (Maguire et al. 2016, Holz et al. 2014). Topical IOP lowering agents require daily administration and a significant percentage of patients demonstrate glaucomatous progression despite IOP lowering (Levin, 2005).

Finally, senolytic therapy of eye diseases may address an underlying common mechanistic cause of the ocular disease rather than impacting only symptoms generated from downstream signaling pathways. A senolytic agent can for example impact on multiple pathology-associated cytokines (inflammatory, cytotoxic, angiogenic, fibrotic) rather than the specific inhibition of a single factor involved in a single aspect of the disease (for example, anti-VEGF therapy for the VEGF related aspect of neovascularization).

As an example, senolytic therapy can reduce a range of growth factors known to be implicated in various stages of AMD. FIG. 1C (Kumar and Fu, 2014) indicates that early deposits in the RPE impact the degeneration of the extracellular matrix including elastin and fibronectin. Increasing oxidative stress induces mitochondrial DNA damage, a known potent inducer of senescence. Additional activation of pro-inflammatory cytokines and chemokines (IL-1, IL-6) follows, with eventual induction of VEGF and metalloprotease (MMPs) and inflammasome activation. A senolytic therapy that targets this range of factors (all identified as components of the SASP) can exert a multi-pronged impact along the pathophysiologic course of AMD, with the ability to modulate and potentially reverse the course of disease. True disease modification has not to date been demonstrated by available therapies for ocular disorders, highlighted by the necessity for frequent administration to control the diseases. The potential for infrequent dosing and disease modification offered by senolytic therapy represents a major advance in ocular disease therapy.

Senescent cell deletion may be a disease modifying treatment for ocular diseases arising from ischemia, degeneration or genetic root causes, by either halting progression or potentially allowing endogenous reparative systems or improved cell function to modify outcomes.

Suitable Senolytic Agents

Compounds that may be useful for clearing senescent cells in or near the eye for purposes of treating ophthalmic conditions according to this invention include Bcl-2 inhibitors, Bcl-xL inhibitors, MDM2 inhibitors, and Akt inhibitors. See U.S. Pat. Nos. 8,691,184, 9,096,625, and 9,403,856; published applications WO 2015/17159, WO 2015/116740, WO 2016/127135, and WO 2017/008060; and unpublished application PCT/CN2016/110309.

Candidate senolytic agents that act as Bcl-2, Bcl-w, and Bcl-xL inhibitors can be characterized as a benzothiazole-hydrazone, an amino pyridine, a benzimidazole, a tetrahydroquinolin, or a phenoxyl compound. Examples of compounds that inhibit Bcl isoforms include WEHI 539, A 1155463, ABT 737, and ABT 263 (Navitoclax).

Candidate senolytic agents that act as MDM2 inhibitors can be characterized as a cis-imidazoline, a dihydroimidazothiazole, a spiro-oxindole, a benzodiazepine, or a piperidinone. Candidate in MDM2 include Nutlin-1, Nutlin-2, Nutlin-3a, RG-7112, RG7388, R05503781, DS-3032b, MI-63, MI-126, MI-122, MI-142, MI-147, MI-18, MI-219, MI-220, MI-221, MI-773, 3-(4-chlorophenyl)-3-((1-(hydroxymethyl)cyclopropyl)methoxy)-2-(4-nitrobenzyl)isoindolin-1-one, Serdemetan, AM-8553, CGMO97, R0-2443, and R0-5963.

Candidate senolytic agents that act as inhibitors of Akt (protein kinase B) are the competitive Akt inhibitors CCT128930, GDC-0068, GSK2110183 (afuresertib), GSK690693, and AT7867; the lipid-based Akt inhibitors Calbiochem Akt Inhibitors I, II and III, PX-866, and Perifosine (KRX-0401); the pseudosubstrate inhibitors vKTide-2 T and FOXO3 hybrid; allosteric inhibitors of the Akt kinase domain, particularly MK-2206 (8-[4-(1-aminocyclobutyl)phenyl]-9-phenyl-2H-[1,2,4]triazolo[3,4-f][1,6]naphthyridin-3-one;dihydrochloride); the antibody GST-anti-Akt1-MTS; the compounds that interact with the PH domain of Akt Triciribine and PX-316; and other compounds exemplified by GSK-2141795, VQD-002, miltefosine, AZD5363, GDC-0068, and API-1.

Exemplary Bcl inhibitors for use in treating ophthalmic conditions according to this invention contain a structure according to Formula I as shown below, or a phosphorylated form thereof.

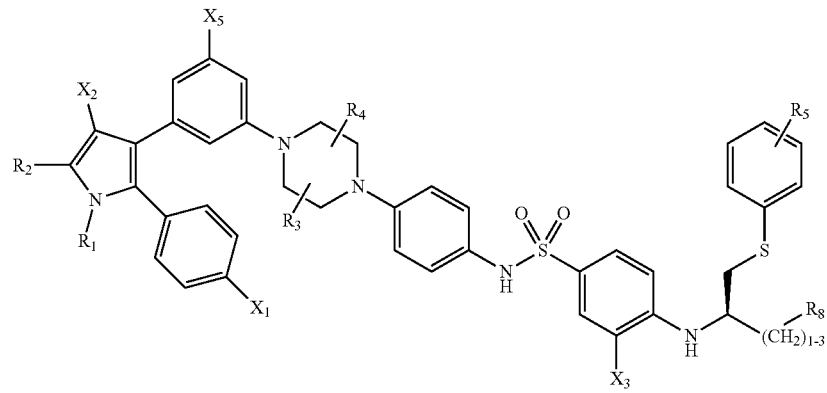

Formula (I)

wherein:

$R_1$ and $R_2$ are independently $C_1$ to $C_4$ alkyl $R_3$, $R_4$ and $R_5$ are independently —H or —$CH_3$;

$R_8$ is —OH or —N($R_6$)($R_7$), wherein $R_6$ and $R_7$ are independently alkyl or heteroalkyl, and are optionally cyclized;

$X_1$ is —F, —Cl, —Br, or —$OCH_3$;

$X_2$ is —$SO_2R'$ or —$CO_2R'$, where R' is —H, —$CH_3$, or —$CH_2CH_3$;

$X_3$ is —$SO_2CF_3$; —$SO_2CH_3$; or —$NO_2$ $X_5$ is —F, —Br, —Cl, —H, or —$OCH_3$.

Optionally, $R_8$ is —N($R_6$)($R_7$), wherein $R_6$ and $R_7$ are independently alkyl or heteroalkyl, and are optionally cyclized.

Optionally, $R_1$ and $R_2$ are independently $C_1$ to $C_4$ alkyl;

$R_3$ and $R_4$ are both —H;

$R_5$ is —H or —$CH_3$;

$R_6$ and $R_7$ are independently alkyl or heteroalkyl, and are optionally cyclized;

$X_1$ is —F or —Cl;

$X_2$ is —$SO_2R'$ or —$CO_2R'$, where R' is —H, —$CH_3$, or —$CH_2CH_3$;

$X_3$ is —$SO_2CF_3$ or —$NO_2$; and $X_5$ is —F or —H;

Other exemplary Bcl inhibitors for use in treating ophthalmic conditions according to this invention contain a structure according to Formula II, as shown below, or a phosphorylated form thereof.

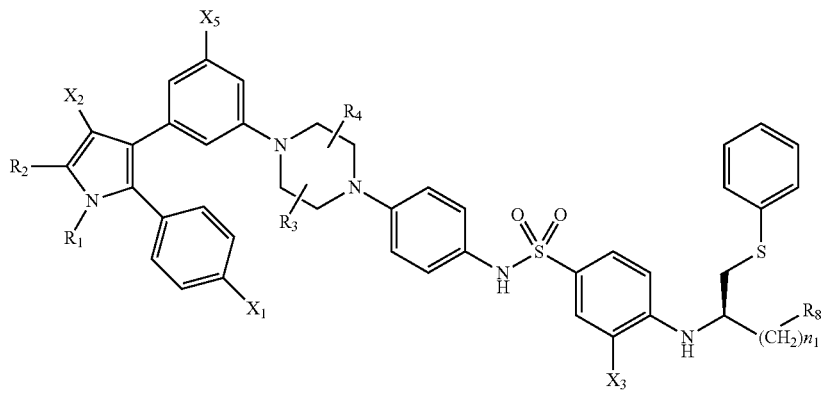

Formula (II)

wherein:

$R_1$ and $R_2$ are independently $C_1$ to $C_4$ alkyl;

$R_3$ and $R_4$ are independently —H or —$CH_3$;

$R_8$ is —OH or

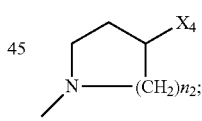

$X_1$ is —F, —Cl, —Br, or —$OCH_3$;

$X_2$ is —$SO_2R'$ or —$CO_2R'$, where R' is —H, —$CH_3$, or —$CH_2CH_3$;

$X_3$ is —$SO_2CF_3$; —$SO_2CH_3$; or —$NO_2$ $X_4$ is —OH, —COOH or —$CH_2OH$;

$X_5$ is —F, —Cl, or —H; and $n_1$ and $n_2$ are independently 1, 2, or 3.

Optionally, $X_3$ is —$SO_2CF_3$ or —$NO_2$, and $R_8$ is

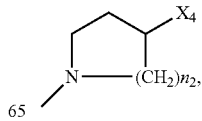

wherein $X_4$ is —OH or —COOH.

Optionally, the compound may have one, two, three, more than three, or all of the following features in any combination:
$R_1$ is isopropyl;
$R_2$ is methyl;
$R_3$ is —H;
$R_4$ is —H;
$X_1$ is —Cl;
$X_2$ is —SO$_2$CH$_3$;
$X_3$ is —SO$_2$CF$_3$;
$X_4$ is —OH;
$n_1$ is 2; and
$n_2$ is 2.

Other exemplary Bcl inhibitors for use in treating ophthalmic conditions according to this invention contain a structure according to Formula III, as shown below, or a phosphorylated form thereof.

Formula (III)

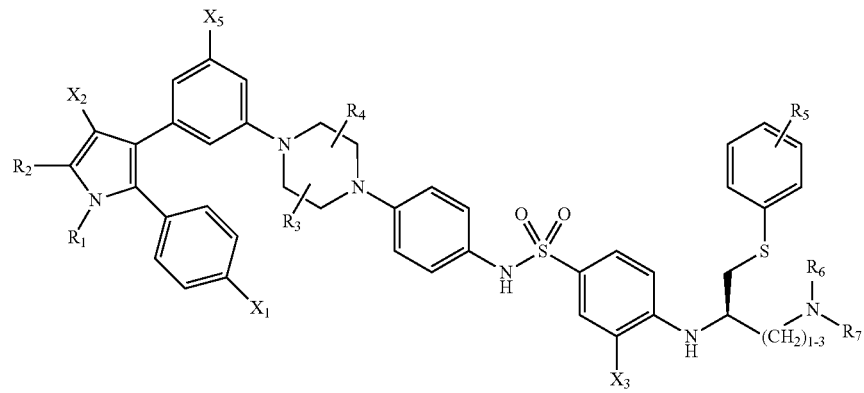

wherein
$R_1$ and $R_2$ are independently $C_1$ to $C_4$ alkyl;
$R_3$, $R_4$ and $R_5$ are independently —H or —CH$_3$;
$R_6$ and $R_7$ are independently alkyl or heteroalkyl, and are optionally cyclized;
$X_1$ is —F, —Cl, —Br, or —OCH$_3$;
$X_2$ is —SO$_2$R' or —CO$_2$R', where R' is —H, —CH$_3$, or —CH$_2$CH$_3$;
$X_3$ is —SO$_2$CF$_3$ or —NO$_2$; and
$X_5$ is —F, —Br, —Cl, —H, or —OCH$_3$;
or alternatively, wherein:
$R_1$ and $R_2$ are independently $C_1$ to $C_4$ alkyl;
$R_3$ and $R_4$ are both —H;
$R_5$ is —H or —CH$_3$;
$R_6$ and $R_7$ are independently alkyl or heteroalkyl, and are optionally cyclized in the manner shown in Formula VII;
$X_1$ is —F or —Cl;
$X_2$ is —SO$_2$R' or —CO$_2$R', where R' is —H, —CH$_3$, or —CH$_2$CH$_3$;
$X_3$ is —SO$_2$CF$_3$ or —NO$_2$; and
$X_5$ is —F or —H.

Other exemplary Bcl inhibitors for use in treating ophthalmic conditions according to this invention contain a structure according to Formula IV, as shown below, or a phosphorylated form thereof.

Formula (IV)

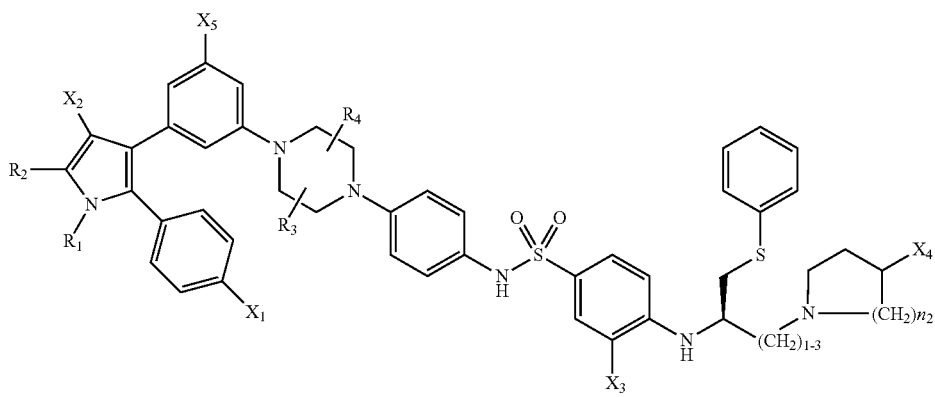

wherein:
R$_1$ and R$_2$ are independently C$_1$ to C$_4$ alkyl;
R$_3$ and R$_4$ are independently —H or —CH$_3$;
X$_1$ is —F, —Cl, —Br, or —OCH$_3$;
X$_2$ is —SO$_2$R' or —CO$_2$R', where R' is —H, —CH$_3$, or —CH$_2$CH$_3$;
X$_3$ is —SO$_2$CF$_3$ or —NO$_2$;
X$_4$ is —OH or —COOH;
X$_5$ is —F —Cl or —H; and
n$_1$ and n$_2$ are independently 1, 2, or 3.

Screening Compounds for Senolytic Activity

These and other compounds can be screened on the molecular level for their ability to perform in a way that indicate that they are candidate agents for use according to this invention.

For example, where the therapy includes triggering apoptosis of senescent cells by way of Bcl-2, Bcl-xL, or Bcl-w, compounds can be tested for their ability to inhibit binding between Bcl-2, Bcl-xL, or Bcl-w and their respective cognate ligand. Example 1 provides an illustration of a homogeneous assay (an assay that does not require a separation step) for purposes of determining binding to the Bcl isoforms. Compounds can be screened on the molecular level for their ability to act as agonists of MDM2, thereby promoting p53 activity and causing senolysis. Example 2 provides an illustration of an assay for this purpose.

Cell Culture Systems for Testing Senolytic Agents

Compounds can be screened for biological activity in an assay using senescent cells. Cultured cells are contacted with the compound, and the degree of cytotoxicity or inhibition of the cells is determined. The ability of the compound to kill or inhibit senescent cells can be compared with the effect of the compound on normal cells that are freely dividing at low density, and normal cells that are in a quiescent state at high density.

Example 3 provides an illustration using the human lung fibroblast IMR90 cell line. Because of the facility of expanding IMR90 cells, they are effective as an early screening tool. Since this disclosure reveals cell types in the eye that generate senescent cells implicated in eye disease, compounds selected in early screening can be rescreened using primary cultures of target eye cells: particularly trabecular meshwork cells, as illustrated in Example 4, and RPE cells, as illustrated in Example 5.

Where technically feasible, tissue explants from human patient donor eyes can be generated and the reduction of senescent cell and disease relevant markers measured after incubation with test compounds. In this format, senolysis, and its downstream impact, can be measured in an intact tissue, where relevant cell types are present and senescence was driven by disease pathogenesis. Tissue explants can also provide a means to assess disease-relevant cell types that are not easily amenable to standard in vitro cell culture methods in isolation (for example, photoreceptors and neurons).

Animal Models for Testing Senolytic Agents

Test compounds can be assessed in preclinical animal models to gain confidence in target engagement of relevant cell types and downstream readouts such as reduction of SASP or efficacy against functional endpoints in mechanistic/disease models.

Evidence of target engagement can be investigated in vivo using models of induced senescence. In order to understand whether test compounds access the disease relevant cell types in the eye, several methods of senescence induction can be pursued. DNA damaging agents such as doxorubicin, bleomycin, and irradiation can induce cellular senescence, and can be directly injected (for example, intravitreal, intracameral, subretinal, etc.) into the eyes of mice (or local or whole-body exposure in the case of irradiation) to drive senescence in the trabecular meshwork or retina. Test compounds can then be administered to determine access of the compounds to appropriate cell layers (as measured by loss of senescence markers). Additionally, many of the SASP factors can be measured from these tissues to understand the downstream impact of senescence induction, and the impact of senolysis on such mediators.

By way of illustration, administration of bleomycin, a DNA damaging agent, to the anterior chamber of the mouse eye leads to cellular senescence in the trabecular meshwork (TM), as detected by the induction of p16 transcript in the TM (Example 8). Elevated relative expression of p16 mRNA was observed 14 days after intracameral (IC) injection of bleomycin in the right eye relative to the control left eye. Intracameral administration of a senolytic (UBX1967) on day 7 post-bleomycin resulted in a reduction of p16 mRNA on day 14, suggesting clearance of senescent cells by UBX1967 in the mouse TM.

The oxygen-induced retinopathy (OIR) model (Scott and Fruttiger, Eye (2010) 24, 416-421, Oubaha et al, 2016) mimics elements of ischemic retinopathies in humans, such as diabetic retinopathy (DR), retinopathy of prematurity (ROP), and diabetic macular edema (DME). Exposure of young mice to a hyperoxic environment leads to obliteration of retinal vasculature, followed by pathological angiogenesis (neovascularization) upon return to ambient air.

The examples below show the efficacy of the model compound UBX1967 in the mouse oxygen-induced retinopathy (OIR) model. Intravitreal (IVT) administration of UBX1967 showed statistically significant improvement in the degree of neovascularization and vaso-obliteration at all dose levels (Example 6A). Additionally, we measured the relative abundance of several transcripts associated with senescence (p16, pai1) and human disease (VEGF) and found that treatment with UBX1967 resulted in a reduction in these transcripts. Senescence-associated β-galactosidase (SA-BGal) activity was also reduced after administration of UBX1967.

The streptozotocin (STZ) rodent model (Feit-Leichman et al, IOVS 46:4281-87, 2005) recapitulates features of diabetic retinopathy and diabetic macular edema through the induction of hyperglycemia via the direct cytotoxic action of STZ on pancreatic beta cells. Hyperglycemia occurs within days following STZ administration and phenotypic aspects of diabetic retinopathy occur within weeks, with vascular leakage and reduced visual acuity and contrast sensitivity demonstrated in these rodents. This model has thus been widely used for the evaluation of therapeutic agents in diabetic eye disease. The data provided below show that UBX1967 improved retinal and choroidal vascular leakage.

Other models of retinal ganglion cell damage can be used in testing that are relevant to glaucoma, where increased intraocular pressure (IOP) is thought to cause retinal ganglion cell loss and optic nerve damage. In preclinical species, increased anterior chamber pressure can result in retinal neuron loss as reported in several established models, including the magnetic microbead occlusion (Ito et al., Vis Exp. 2016 (109): 53731) and other glaucoma models (Almasieh and Levin, Annu Rev Vis Sci. 2017). Additionally, ischemia-reperfusion has been demonstrated to cause retinal injury which may result in cellular senescence. Presence of retinal senescence in such models can be used to monitor the impact of senolysis after intravitreal injection of test compounds.

Routes of Administration

Typically a senolytic of this invention is administered directly to the exterior or interior of the eye of the subject, or to a surrounding tissue. Local administration includes topical administration, administration via syringe and/or administration via an implantable device. Included is the treatment of anterior (front of the eye) ocular conditions and posterior (back of the eye) ocular conditions.

An anterior ocular condition is a disease, ailment or condition that affects or involves an anterior ocular region or site, such as a periocular muscle, an eyelid or an eye tissue or fluid which is located anterior to the posterior wall of the lens capsule or ciliary muscles. An anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerves which vascularize or innervate an anterior ocular region or site. Examples include dry eye syndromes, conjunctival diseases, conjunctivitis, corneal diseases, presbyopia, cataract, and refractive disorders. Glaucoma can also be considered to be an anterior ocular condition because a clinical goal of glaucoma treatment can be to reduce a hypertension of aqueous fluid in the anterior chamber of the eye (i.e., reduce intraocular pressure).

A posterior ocular condition is a disease, ailment or condition which primarily affects or involves a posterior ocular region or site such as sclera, ciliary body, choroid (in a position posterior to a plane through the posterior wall of the lens capsule), vitreous, posterior chamber, retina, retinal pigment epithelium, Bruch's membrane, optic nerve (i.e., the optic disc), and blood vessels and nerves which vascularize or innervate a posterior ocular region or site. Examples include acute macular neuroretinopathy; choroidal neovascularization; histoplasmosis; infections, such as virus-caused infections; non-exudative age related macular degeneration and exudative age related macular degeneration; edema, such as macular edema, cystoid macular edema and diabetic macular edema; multifocal choroiditis; ocular trauma which affects a posterior ocular site or location; retinal disorders, such as central retinal vein occlusion, diabetic retinopathy, proliferative vitreoretinopathy (PVR), retinal arterial occlusive disease, retinal detachment, inflammatory chorio-retinal disease; sympathetic ophthalmia; retinitis pigmentosa, and glaucoma. Glaucoma can be considered a posterior ocular condition because the therapeutic goal is to prevent the loss of or reduce the occurrence of loss of vision due to damage to or loss of retinal ganglion cells or optic nerve cells (i.e. neuroprotection).

In some cases, an effective amount of a senolytic is delivered to the anterior chamber of the eye via topical administration. The senolytic may be instilled in the anterior of the eye using eye drops, ointment or gel (e.g., to the conjunctiva and/or cornea) as is needed to treat, ameliorate, and/or prevent the eye disease of interest. The senolytic agent can be an ophthalmic preparation in the form of eye drops that contains an amount of the active agent sufficient to provide for a therapeutically effective concentration at the site of action inside the eye.

Local administration to the front of the eye (e.g., to the conjunctiva and/or cornea) may also be done using a contact lens that carries the senolytic agent. This can improve the bioavailability and prolong the residence time of an active agent.

To increase the amount of drug load and to control drug release, a contact lens or hydrogel may include: (i) polymeric hydrogels with controlled hydrophilic/hydrophobic copolymer ratio; (ii) hydrogels for inclusion of drugs in a colloidal structure dispersed in the contact lenses; (iii) ligand-containing hydrogels; (iv) molecularly imprinted polymeric hydrogels; (v) hydrogel with the surface containing multilayer structure for drugs loading and releasing. Hydrogels are a preferred material of soft contact lenses because of their biocompatibility and transparent characteristic. A hydrogel contact lens can be used to release an active agent to the front of the eye in a controlled release upon contact with the thin film of tears coating the eye. The contact lens can be worn daily according to a dosing schedule to provides for local administration of an effective amount of the senolytic for treatment of an eye disease (e.g., as described herein). Contact lens devices include those devices described in U.S. Pat. No. 6,827,996 and U.S. Publication Nos. 2010/0330146 and 2006/0251696.

Local administration to the front of the eye can also be done by subconjunctival injection. A subconjunctival injection can be used to inject a senolytic to either the subconjunctival space or the sub-Tenon's space. Since the subconjunctival space is more anterior that the sub-Tenon's space, subconjunctival injections can have a more pronounced effect on drug delivery to the anterior segment, while sub-Tenon's injections can have more of an effect the posterior segment.

Local administration to the anterior and posterior segments of the eye can also be achieved by intraocular injection, e.g., an intracameral or intravitreal injection. An intracameral injection is an injection that is generally delivered into a chamber in the anterior of the eye (e.g., in front of the lens). An intravitreal injection is an injection delivered into the vitreous chamber in the posterior of the eye (e.g., behind the lens). Because of the risk of damage to the retina layers and optic nerve by raising intraocular pressure, a maximum volume of about 0.1 mL should be administered by either intracameral or intravitreal injection. In some cases, an intracameral injection can provide administration without an increase in intraocular pressure that is associated with an intravitreal injection. A sudden increase in intraocular pressure can cause discomfort to a patient and place the optic nerve at risk of damage. Administration via injection is generally performed in a manner that minimizes exposure of the eye to pathogens.

Local administration can also be done via an implantable ocular device, placed in the eye, for example, by corneal incision. Ocular devices include stents (e.g., trabecular stent), organo-gel implant, and those compositions and devices described in U.S. Pat. Nos. 5,501,856, 5,869,079, 5,824,072, 4,997,652, 5,164,188, 5,443,505 and 5,766,242.

U.S. Pat. No. 5,501,856 discloses controlled-release pharmaceutical preparations for intraocular implants to be applied to the interior of the eye after a surgical operation for disorders in retina/vitreous body or for glaucoma. U.S. Pat. No. 5,869,079 discloses combinations of hydrophilic and hydrophobic entities in a biodegradable sustained release implant, and describes a polylactic acid polyglycolic acid (PLGA) copolymer implant comprising dexamethasone. U.S. Pat. No. 5,824,072 discloses implants for introduction into a suprachoroidal space or an avascular region of the eye, and describes a methylcellulose implant comprising dexamethasone. U.S. Pat. Nos. 4,997,652 and 5,164,188 disclose biodegradable ocular implants comprising microencapsulated drugs, and describes implanting microcapsules comprising hydrocortisone succinate into the posterior segment of the eye. U.S. Pat. No. 5,164,188 discloses encapsulated agents for introduction into the suprachoroid of the eye, and describes placing microcapsules and plaques comprising hydrocortisone into the pars plana. U.S. Pat. Nos. 5,443,505 and 5,766,242 discloses implants comprising active agents for introduction into a suprachoroidal space or an avascular region of the eye, and describes placing microcapsules and plaques comprising hydrocortisone into the pars plana.

To provide a delayed release drug delivery implant or depot, an injectable formulation including the subject active agent can be injected into a subject, which results in the in situ formation of an organogel implant. Upon contact with bodily fluid, crosslinking agents begin to crosslink the organogel to form a more stable matrix that modulates the escape of the active agent to the eye of the subject. In some instances, this method of administration can provide a prolonged release period of the active agent. In some cases, an in vivo biodegradable cross-linked matrix is formed that includes a non-aqueous aprotic biocompatible solvent system that is non-miscible with water (Zhou, T, et al.," Journal of Controlled Release 55: 281-295, 1998).

Formulation of Medicaments

An ophthalmic preparation can be prepared by mixing a senolytic agent with a pharmaceutically acceptable base or carrier and as needed one or more pharmaceutically acceptable excipients. Ingredients acceptable in an ophthalmic formulation are excipients or carriers that cause little to no ocular irritation, provide suitable preservation if needed, and deliver one or more agents in a suitable volume. Examples of a base or carrier include water; an aqueous solvent such as a polar solvent; a polyalcohol; a vegetable oil; and an oily base. Examples of the base or carrier for an intraocular injection include water for injection and physiological saline.

For ophthalmic delivery, a senolytic agent may be combined with acceptable excipients for use in and around the eye, such as a surfactant, preservatives, co-solvents, a flavor or cooling agent, an antiseptic, a bactericide or antibacterial agent, a pH adjusting agent, a tonicity agent, a chelating agent, a buffering agent, a stabilizer, an antioxidant, viscosity enhancers, penetration enhancers, sodium chloride and a thickening agent. In some cases, a composition for intraocular injection may contain one or more of a solubilizing agent, a suspending agent, a tonicity agent, a buffering agent, a soothing agent, a stabilizer, and an antiseptic. The ophthalmic composition carrier and excipients can be combined to form an aqueous, sterile ophthalmic suspension, solution, or viscous or semi-viscous gels or other types of solid or semisolid composition such as an ointment.

Exemplary excipients and additives that can be used include the following. Surfactants: for example, nonionic surfactants such as polyoxyethylene (hereinafter sometimes referred to as "POE")-polyoxypropylene (hereinafter sometimes referred to as "POP") block copolymers (e.g., poloxamer 407, poloxamer 235, poloxamer 188), ethylenediamine POE-POP block copolymer adducts (e.g., poloxamine), POE sorbitan fatty acid esters (e.g., polysorbate 20, polysorbate 60, polysorbate 80 (TO-10 etc.)), POE hydrogenated castor oils (e.g., POE (60) hydrogenated castor oil (HCO-60 etc.)), POE castor oils, POE alkyl ethers (e.g., polyoxyethylene (9) lauryl ether, polyoxyethylene (20) polyoxypropylene (4) cetyl ether), and polyoxyl stearate; amphoteric surfactants such as glycine-type amphoteric surfactants (e.g., alkyl diaminoethyl glycine, alkyl polyaminoethyl glycine), betaine-type amphoteric surfactants (e.g., lauryldimethylaminoacetic betaine, imidazolinium betaine); cationic surfactants such as alkyl quaternary ammonium salts (e.g., benzalkonium chloride, benzethonium chloride); etc.

Flavors or cooling agents: for example, camphor, borneol, terpenes (these may be in the d-form, l-form, or dl-form); essential oils such as mentha water, *eucalyptus* oil, bergamot oil, anethole, eugenol, geraniol, menthol, limonene, mentha oil, peppermint oil, rose oil, etc.

Antiseptics, bactericides, or antibacterial agents: for example, polidronium chloride, alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl paraoxybenzoate, ethyl paraoxybenzoate, propyl paraoxybenzoate, butyl paraoxybenzoate, oxyquinoline sulfate, phenethyl alcohol, benzyl alcohol, biguanide compounds (in particular, polyhexamethylene biguanide or its hydrochloride etc.), Glokill (Rhodia Ltd.), etc.

pH adjusting agents: for example, hydrochloric acid, sodium hydroxide, potassium hydroxide, calcium hydroxide, magnesium hydroxide, triethanolamine, monoethanolamine, diisopropanolamine, sulfuric acid, phosphoric acid.

Tonicity agents: for example, sodium bisulfite, sodium sulfite, potassium chloride, calcium chloride, sodium chloride, magnesium chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, glycerin, propylene glycol.

Chelating agents: for example, ascorbic acid, edetic acid tetrasodium, sodium edetate, citric acid. Buffering agents: for example, phosphate buffering agents; citrate buffering agents such as citric acid and sodium citrate; acetate buffering agents such as acetic acid, potassium acetate, and sodium acetate; carbonate buffering agents such as sodium bicarbonate and sodium carbonate; borate buffering agents such as boric acid and borax; amino acid buffering agents such as taurine, aspartic acid and its salts (e.g., potassium salts etc.), and ε-aminocaproic acid.

Ophthalmic solution formulations may be prepared by dissolving the agent in a physiologically acceptable isotonic aqueous buffer. Further, the ophthalmic solution may include an ophthalmologically acceptable surfactant to assist in dissolving the agent. Viscosity building compounds, such as hydroxymethyl cellulose, hydroxyethyl cellulose, methylcellulose, polyvinylpyrrolidone may be added to improve the retention of the compound.

Sterile ophthalmic gel formulations may be prepared by suspending the agent in a hydrophilic base prepared from the combination of, for example, CARBOPOL®-940. VISCOAT® (Alcon Laboratories, Inc., Fort Worth, Tex.) may be used for intraocular injection. Other compositions of the present invention may contain penetration enhancing materials such as CREMOPHOR® (Sigma Aldrich, St. Louis, Mo.) and TWEEN® 80 (polyoxyethylene sorbitan monolaureate, Sigma Aldrich), in the event the agents of the present invention are less penetrating in the eye.

This invention provides commercial products that are kits that enclose unit doses of one or more of the agents or compositions described in this disclosure. Such kits typically comprise a pharmaceutical preparation in one or more containers. The preparations may be provided as one or more unit doses (either combined or separate). The kit may contain a device such as a syringe for administration of the agent or composition in or around the eye of a subject in need thereof. The product may also contain or be accompanied by an informational package insert describing the use and attendant benefits of the drugs in treating the senescent cell associated eye disease, and optionally an appliance or device for delivery of the composition.

Ophthalmic Conditions Suitable for Treatment

Provided in the sections that follow is a discussion of specific eye diseases arranged by broad etiologic category (supra) that are candidates for treatment with a senolytic agent in accordance with this invention. The degree to which a particular ophthalmic condition will be amenable to treatment with a senolytic agent will depend on the degree and extent senescent cells play a role in disease pathology or symptomatology. The treatment protocol and patient management are within the judgment of the managing clinician. The efficacy of the therapy can be determined empirically.

Type 1: Ischemic or Vascular Conditions.

These conditions are characterized by a restriction in blood supply to tissues, causing a deficiency of oxygen and/or essential nutrients needed for cellular metabolism to keep tissue functional. Ischemia is generally caused by diseases associated with blood vessels, with resultant damage to or dysfunction of tissue. It also includes local deficiencies that arise in a given part of a body resulting from issues affecting blood flow but not the vessel itself (such as vasoconstriction, thrombosis, or embolism).

Examples of ischemic or vascular ocular diseases include diabetic retinopathy, glaucomatous retinopathy, ischemic arteritic optic neuropathies, and vascular diseases characterized by arterial and venous occlusion, retinopathy of prematurity and/or sickle cell retinopathy.

The general approach and objectives of senolytic therapy for ischemic or vascular conditions are based on the following:

Ischemia produces a well-known series of pathophysiologic interactions in the eye. Senolytic therapy impacts this pathophysiology by amelioration of the multiple known inducers of senescence that populate the ischemic pathway. The primary insult of an ischemic event triggers a cascade that exposes the cells of the affected tissue to inducers of senescence that include mitochondrial and DNA damage, oxidative stress, inflammation and lipid peroxidation.

The accumulation of senescent cells and release of their associated SASP has a negative impact on the tissue microenvironment, both for directly and indirectly impacted cells. The objective of senolytic therapy for ischemic diseases of the eye is to decrease the population of senescent cells present in the impacted region, and decrease the associated SASP factor impact on surrounding cells. This limits ongoing damage in tissue following an ischemic event, and potentially restore function through improved features of the cellular microenvironment.

As an example, the elimination of senescent cells in the setting of ischemia impacts visual function by allowing functioning retinal ganglion cells to thrive in a healthier local environment, free of the SASP associated detrimental inflammatory, angiogenic and extracellular matrix-modifying factors. Ischemic events of the visual system commonly affect posterior structures of the eye. The ischemia can be influenced by anterior segment features of certain diseases. Thus, the senolytic agent can be delivered in the anterior compartment, or both the anterior and posterior compartment.

Underlying Pathophysiology

Retinal ischemia contributes to multiple ocular disorders, and occurs secondary to multiple underlying etiologies. Ischemia has been implicated in glaucoma, diabetic retinopathy, retinal and choroidal vascular occlusive disease, retinopathy of prematurity and ischemic and traumatic optic neuropathies. Retinal and macular edema associated with these conditions is also secondary to the consequences of the ischemic cascade.

Figure 1A:
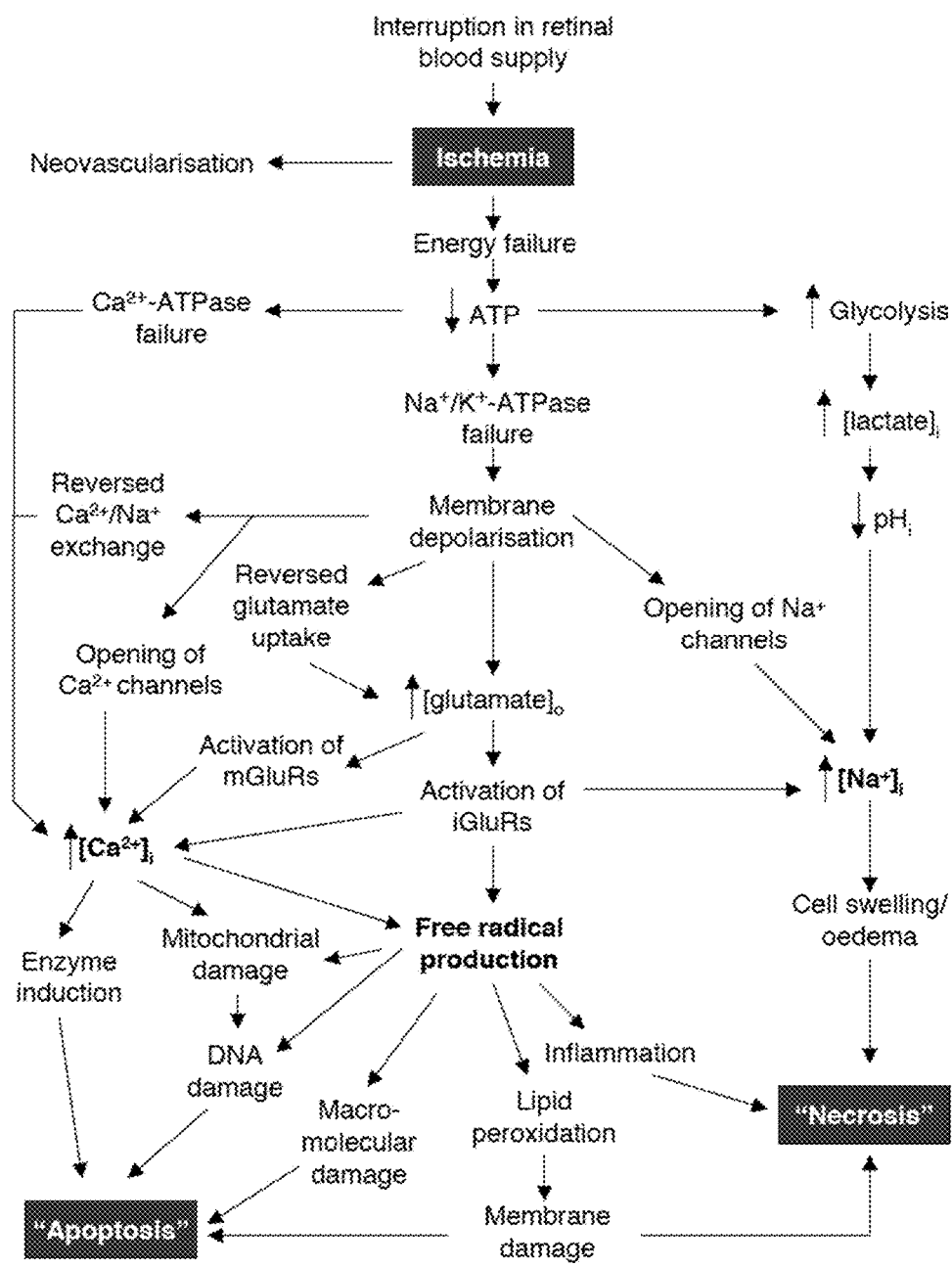

FIG. 1A shows the pathophysiologic interactions in the eye that result from ischemia. All known retinal ischemic paradigms result in loss of ganglion cells, crucial to the maintenance of functional vision (Osborne N et al. 2004). Additionally, neovascularization mediated by multiple growth factors such as vascular endothelial growth factor (VEGF), TNFα, TGFβ, FGF, PKC, angiopoietins, PDGF, among others (Ucuzian et al., 2010), is another end stage effect of ischemia and is associated with vision threatening complications of both retinal and choroidal neovascular disease (Campochiaro 2015).

Ischemia secondary to the interruption of retinal blood supply of any etiology initiates a cascade that can ultimately lead to cell death and is known to involve selective neuronal death, cellular edema and neovascularization. This is outlined in detail in FIG. 1A, which highlights the key steps in the cascade which include failure of the sodium-potassium ATPase pump, membrane depolarization, and accumulation of sodium and calcium ions in the cytoplasm with subsequent formation of destructive free radicals. This process ultimately leads to cell death by necrosis or apoptosis (Osborne N et al. 2004). The ischemic pathway is thus populated with known inducers of senescence, and supports the hypothesis that a senolytic agent can impact the effects of multiple ischemia-induced senescent responses.

Glaucoma is another example of an ocular disease that illustrates this progression to retinal ganglion cell death, influenced by a range of factors that include ischemia (Choi and Kook, 2015), increased IOP, genetic susceptibility and oxidative stress (Wang et al. 2014), each of which may induce senescence and contribute to the changes in the environmental milieu produced by senescent cells and their associated SASP factors.

Figure 1B:
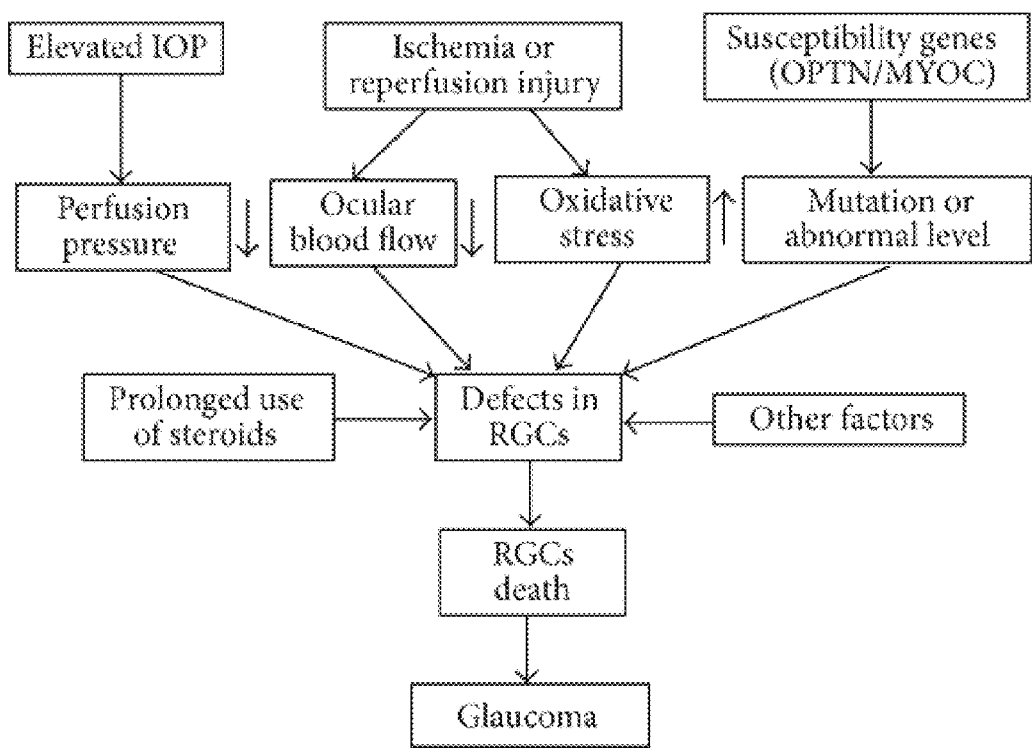
Figure 1C:
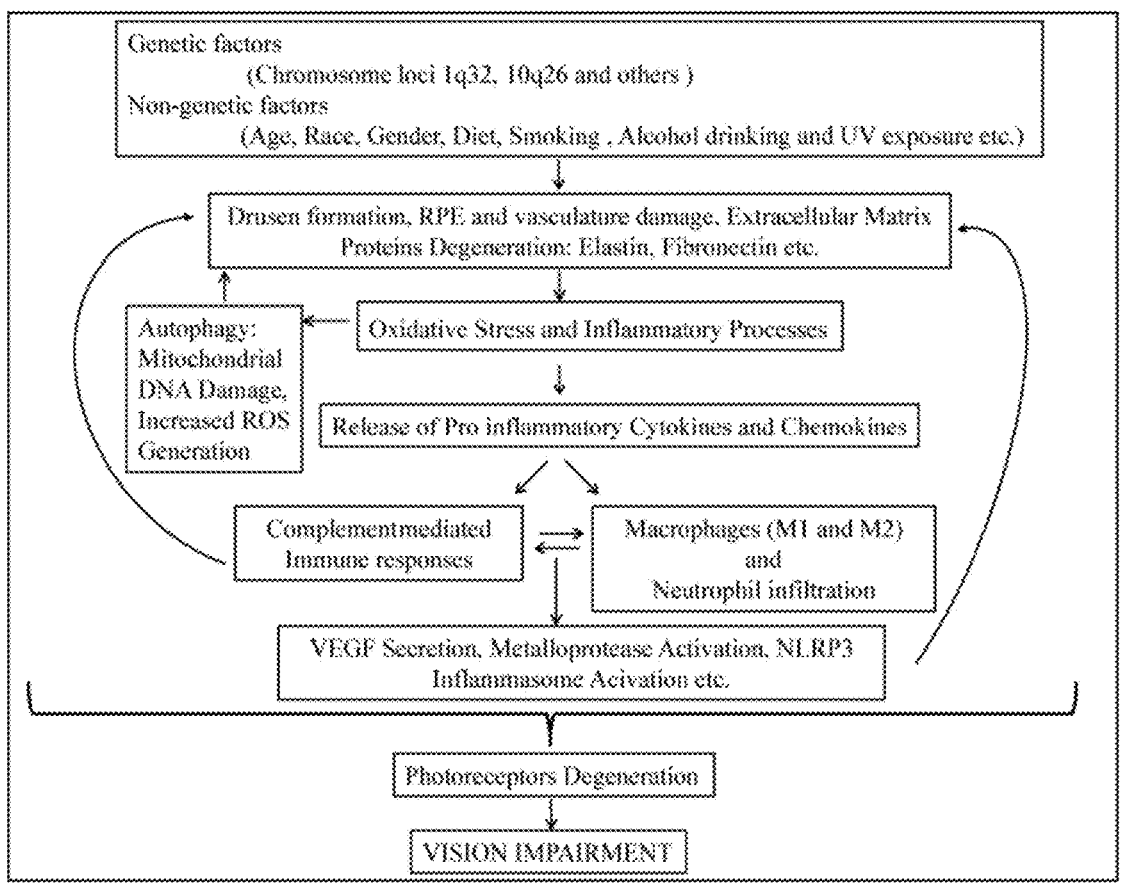

FIG. 1B shows the multifactorial pathophysiology of glaucoma, leading to retinal ganglion cell (RGC) cell death (Wang et al. 2014).

Glaucoma

Glaucoma has significant associations with age both in prevalence and pathophysiologic characteristics. The prevalence of glaucoma increases markedly over the age of 60 in Caucasians and over 40 in African-Americans and Hispanics. Age is the most consistent and least variable risk factor in glaucoma, including IOP. Age is also associated with decreased outflow facility in the eye and associated IOP increase, stiffening of the sclera with subsequent impact on the biomechanical properties of the optic nerve, and a diminished population of retinal ganglion cells (Caprioli, 2013).

Glaucoma is a form of optic neuropathy (a disorder of the optic nerve) that is associated with an increase in intraocular pressure resulting from an inability to relieve pressure in the anterior chamber of the eye caused by an abnormal buildup of the clear fluid known as "aqueous humor." There are two primary types of glaucoma: open-angle glaucoma and angle-closure glaucoma. Glaucoma can be classified on the basis of pathogenesis as primary glaucoma: primary open-angle glaucoma or primary angle-closure glaucoma; and secondary glaucoma induced by other disorders, including steroid-induced glaucoma, pseudoexfoliation or pigment dispersion glaucoma. In open-angle glaucoma (also referred to as wide-angle glaucoma), the trabecular meshwork drain structure or channel of the eye does not drain fluid produced by the ciliary body as it should, leading to an increase in intraocular pressure. In angle-closure (or narrow-angle) glaucoma, the eye doesn't drain correctly due to a too narrow angle between the iris and cornea, which can cause a sudden buildup of intraocular pressure. The presentation of angle closure glaucoma may be acute or chronic. Angle-closure glaucoma can be linked to farsightedness and cataracts.

Aqueous humor, which is formed in the ciliary body in the posterior chamber of the eye at the rate of about 2.5 microliters per minute, enters the anterior chamber through a cleft between the front of the lens and the back of the iris through the pupillary opening in the iris. When the eye is functioning normally, the aqueous humor flows out of the anterior chamber at the same or substantially the same rate it enters and, as result, the pressure in the eye remains within the normal range of about 12 to 22 mm Hg. Fluids are relatively incompressible, and thus intraocular pressure is distributed relatively uniformly throughout the eye. Increase in intraocular pressure takes place when an imbalance between ciliary body production of aqueous fluid and outflow of this fluid occurs.

Outflow of aqueous humor from the anterior chamber is by two routes. A minor amount (about 10%) exits through "uveoscleral drainage" between muscle fibers in the ciliary body. This flow is independent of intraocular pressure. However, the major route of outflow is through the trabecular meshwork (TM) into Schlemm's canal and is pressure dependent. When this route becomes impeded, the intraocular pressure can become elevated because the inflow of aqueous humor is not balanced until the pressure in the eye rises sufficiently to overcome the impediment to outflow. Our finding of senescent cells in the TM of patients with glaucoma supports TM dysfunction in the pathophysiology of this disease. In time, this can result in loss of vision, both peripheral and central, and eventually lead to complete blindness via loss of retinal ganglion cell and optic nerve function.

Subjects with open-angle glaucoma and chronic angle-closure glaucoma may have no obvious symptoms early in the course of the disease. Visual field loss can occur at later stages of glaucoma. A subject in need of treatment for glaucoma may exhibit one or more symptoms including, but not limited to, elevated intraocular pressure, optic-nerve abnormalities with corresponding visual field loss, decreased visual acuity, corneal swelling and a closed drainage angle. In certain instances, a subject with fluctuating levels of intraocular pressure may experience haziness of vision and see haloes around lights. In some cases, the symptoms of acute angle-closure include the rapid onset of eye pain, headache, nausea, vomiting and visual blurring. The eyes of patients with acute angle-closure glaucoma can appear red, and the pupil of the eye may be large and nonreactive to light. In certain cases, the cornea may appear cloudy to the naked eye.

Subjects to be treated according to this invention can be selected based on a clinical presentation or ophthalmic examination that suggests the presence of glaucoma, using the diagnostic methods outlined previously. These include slit lamp and gonioscopy, tonometry, optic nerve imaging and examination, fundus photography and OCT methods.

The senolytic agents of this invention can provide for a reduction of intraocular pressure in the eye of a subject in need of treatment, e.g., a reduction from an elevated intraocular to a normal intraocular pressure through the elimination of senescent cells and associated SASP in the TM and anterior chamber. Optic nerve damage can be alleviated and inhibited by sufficiently reducing intra-ocular pressure and in some cases, can provide for restoration or improvement of retinal visual capacity.

In some instances, the senolytic is administered by intra-cameral injection into the anterior chamber of the eye, or by intravitreal injection into a posterior segment, vitreous, or vitreous chamber of the eye. The senolytic agents of this invention may be effective to enhance aqueous humor outflow thereby reducing intraocular pressure. Intravitreal administration may take advantage of the eye's natural fluid flow: the vitreous humor delivers the active agent to the trabecular meshwork and uveoscleral pathway as it flows to the anterior chamber. This can provide for delivery of the active agent to the site of action in the anterior segment of the eye. Intravitreal delivery may also directly target retinal ganglion cells impacted in glaucoma.

Optionally, a senolytic agent can be administered in conjunction with a surgical method of relieving intraocular pressure: for example, canaloplasty, laser trabeculoplasty, trabeculectomy, and the insertion of shunts or other implanted devices. Generally, surgical interventions provide temporary relief from elevated intraocular pressure. Implanted drainage devices include those described in U.S. Pat. No. 9,468,558, which can be inserted in the eye via an incision and positioned, e.g., on the sclera posterior to the limbus to facilitate drainage.

Diabetic Retinopathy

The prevalence of diabetes and diabetic retinopathy increases with age and is the most common cause of blindness in people over the age of 50. It is a multifactorial disorder, with hyperglycemia exerting toxic effects on cells and inflammatory cytokine implicated in many aspects of diabetic eye disease (Lutty 2013).

Diabetic eye disease develops in subjects that have diabetes due to changes in the cells that line blood vessels and encompasses both vascular and neural dysfunction. Patients with diabetes often develop ophthalmic complications, such as corneal abnormalities, glaucoma, iris neovascularization, cataracts and neuropathies. Diabetic retinopathy is a common and potentially serious complication of diabetes.

The duration and severity of hyperglycemia is a factor linked to the development of diabetic retinopathy. When glucose levels are high, as in diabetes, glucose can cause damage in a number of ways. For example, glucose, or a metabolite of glucose, binds to the amino groups of proteins, leading to tissue damage. In addition, excess glucose enters the polyol pathway resulting in accumulations of sorbitol. Sorbitol cannot be metabolized by the cells of the retina and can contribute to high intracellular osmotic pressure, intracellular edema, impaired diffusion, tissue hypoxia, capillary cell damage, and capillary weakening. Diabetic retinopathy involves thickening of capillary basement membranes and prevents pericytes from contacting endothelial cells of the capillaries. Loss of pericytes increases leakage of the capillaries and can lead to a breakdown of the blood-retina barrier. Weakened capillaries can lead to aneurysm formation and further leakage. These effects of hyperglycemia can also impair neuronal functions in the retina. This is an early stage of diabetic retinopathy termed nonproliferative diabetic retinopathy.

Diabetic retinopathy is also a degenerative disease of the neural retina, associated with alterations in neuronal function prior to the onset of clinical vascular disease. Retinal capillaries can become occluded in diabetes causing areas of ischemia in the retina. The non-perfused tissue responds by eliciting new blood vessel growth from existing vessels (i.e., angiogenesis). These new blood vessels can also cause loss of sight, a condition called proliferative diabetic retinopathy, since the new blood vessels are fragile and tend to leak blood into the eye. In advanced proliferative diabetic retinopathy, an angiogenic, VEGF-mediated response with retinal neo-vascularization ensues, placing the eye at further risk for severe visual loss due to the development of vitreous hemorrhage or traction retinal detachment. Irreversible vascular or neuronal damage is possible without treatment, underscoring the need for early intervention.

Symptoms of diabetic retinopathy include loss of central vision, inability to see colors, blurry vision, floaters, distortion, holes or black spots in vision. In the initial stages of diabetic retinopathy, in some cases, a subject can be asymptomatic. However, microaneurysms in the eye can be an early clinical sign of diabetic retinopathy. In some cases, the microaneurysm occurs secondary to capillary wall outpouching due to pericyte loss, and can appear as small, red dots in the superficial retinal layer.

Diagnostic methods include complete ophthalmic examination as outlined previously, with fluorescein angiography, optical coherence tomography scanning (OCT) and B-scan ultrasonography commonly used ancillary tests to stage and monitor response to therapy. The severity of nonproliferative diabetic retinopathy can be assessed by the presence, number and locations of microaneurysms and hemorrhages. Microaneurysms can appear as pinpoint, hyperfluorescent lesions in early phases of the angiogram and typically leak in the later phases of a fluorescein angiography test. Proliferative diabetic retinopathy can be assessed in part via the presence of neovascularization, preretinal hemorrhages, hemorrhage into the vitreous, fibrovascular tissue proliferation, and traction retinal detachments. OCT can be used to determine the thickness of the retina and the presence of swelling within the retina, as well as associated vitreomacular traction.

Further signs and symptoms of diabetic retinopathy include: 1) Dot and blot hemorrhages, which can appear similar to microaneurysms if small and can occur as microaneurysms rupture in the deeper layers of the retina (inner nuclear and outer plexiform layers); 2) Flame-shaped hemorrhages which are splinter hemorrhages that occur in the more superficial nerve fiber layer; 3) Retinal edema and hard exudates which are caused by the breakdown of the blood-retina barrier, allowing leakage of serum proteins, lipids, and protein from the vessels; 4) Cotton-wool spots which are nerve fiber layer infarctions from occlusion of precapillary arterioles; they are frequently bordered by microaneurysms and vascular hyperpermeability; 5) Venous loops and venous beading which can occur adjacent to areas of nonperfusion; they reflect increasing retinal ischemia, and their occurrence can be a predictor of progression to proliferative diabetic retinopathy (PDR); 6) Intraretinal microvascular abnormalities which include remodeled capillary beds without proliferative changes; these can usually be found on the borders of the nonperfused retina; and 7) Macular edema that causes visual impairment.

Other Vascular Eye Diseases

Other vascular eye diseases are exemplified by arterial and/or venous occlusion of the retina and/or optic nerve and retinopathy (e.g., retinopathy of prematurity and/or sickle cell retinopathy).

Retinal vein occlusion (RVO) is a blockage of the small veins that carry blood away from the retina. Blockage of smaller veins (e.g., branch veins) in the retina can occur in places where retinal arteries that have been thickened or hardened by atherosclerosis cross over and place pressure on a retinal vein. With blockage, pressure builds up in the capillaries, leading to hemorrhage and leakage of fluid and blood. This can lead to macular edema with leakage near the macula. Macular ischemia occurs when these capillaries, which supply oxygen to the retina, manifest leakage and nonperfusion. Neovascularization, new abnormal blood vessel growth, then occurs, which can result in neovascular glaucoma, vitreous hemorrhage, and, in late or severe cases, retinal detachment. Visual morbidity and blindness that occurs in RVO can result from events of macular edema, retinal hemorrhage, macular ischemia, and/or neovascular glaucoma.

A related event is central or branch retinal artery occlusion (RAO) that can occur when a plaque (e.g., blood clot or fat deposit) obstructs a blood vessel or artery in the eye. This can result in a sudden and permanent loss of vision, usually in just one eye. In some cases of central RAO, fundoscopic examination of the affected eye can show a pale retina with a cherry red macula (i.e., a cherry red spot) that results from obstruction of blood flow to the retina from the retinal artery, causing pallor, and continued supply of blood to the choroid from the ciliary artery, resulting in a bright red coloration at the thinnest part of the retina (i.e., macula). In general, this does not develop until after an embolism, and can resolve within days of the acute event. In some cases, by this time visual loss is permanent and primary optic atrophy has developed. In some cases, where a cilioretinal artery supplies the macula, a cherry red spot is not observed. Branch RAO can occur when the plaque lodges in a more distal branch of the retinal artery and can involve the temporal retinal vessels. In some cases, a subject at risk of retinal artery occlusion is identified and treated using a senolytic agent before serious occlusion occurs.

Retinopathy of prematurity (ROP) (also referred to as retrolental fibroplasia (RLF)) is a vascular eye disease caused by fibrovascular proliferation, e.g., disorganized growth of retinal blood vessels, which may result in scarring and retinal detachment. Oxygen toxicity and relative hypoxia can contribute to the development of ROP. Various stages of ROP disease have been defined (Committee for the Classification of Retinopathy of Prematurity, Arch Ophthalmol. 102(8): 1130-1134, 1984.

Sickle cell retinopathy (SCR) can develop in subjects suffering from sickle cell disease, in some cases, during the second decade of life. The ocular manifestations of sickle cell disease (SCD) result from vascular occlusion, which may occur in the conjunctiva, iris, retina, and choroid. SCR is triggered by vaso-occlusion of the ocular microvasculature, as opposed to diabetic retinopathy which can be associated with overexposure of the vascular tissues to hyperglycemia. SCR may lead to visual impairment depending on its localization and affected tissue. SCR can be classified as non-proliferative or proliferative according to the presence or absence of neovascularization in the eye.

In the non-proliferative form of SCR clinical findings can include salmon patch hemorrhages, iridescent spots and black sunbursts, which can be observed in the peripheral retina. Venous tortuosity, enlargement of the foveal avascular zone, central retinal artery obstruction and peri-papillary and peri-macular arteriolar occlusions can also be observed in the central part of the retina.

Proliferative SCR complications can lead to visual impairment or loss in 10-20% of affected eyes. In some cases, a subject may be diagnosed by a history of spontaneous regression after an initial development of proliferative SCR. Peripheral retinal neovascularization can develop after vaso-occlusion of the peripheral retina that can grow anteriorly from perfused to non-perfused retina. Initially these new vessels are flat and resemble sea fans. Neovascularization is capable of causing vitreous hemorrhage due to the constant leaking of blood components into the vitreous through the fragile neovascular tissue. The repetition of this hemorrhagic phenomenon leads to worsening of the vitreoretinal traction, with the potential of causing rhegmatogenous or tractional retinal detachment.

Senolytic therapy can be applied to a range of ischemic ocular disease phenotypes that include RGC loss in glaucoma, diabetic and vascular occlusive retinopathies (e.g. arterial and venous occlusion, retinopathy of prematurity, sickle cell retinopathy, inflammatory and infectious retinopathies, radiation retinopathy, etc.) and neovascular AMD (known to be mediated by VEGF and other known SASP factors such as IL-6). These phenotypes have well defined clinical features that can be diagnosed and monitored by a variety of clinical testing procedures including examination and tests of retinal structure (for example, fluorescein angiography for areas of non-perfusion, optical coherence tomography for retinal cellular layer structure, fluid presence, thickness) and function (visual field testing, electrophysiology which can specifically measure function of the retinal ganglion cells).

In support of this invention, the images in FIGS. 12A and 12B show the presence of senescent cells in trabecular meshwork tissue of patients with glaucoma. There is an association of senescent cells with retinal ganglion cell layer loss in glaucoma (Skowronska-Krawcyzk, 2015; Li et al 2017).

Type 2: Degenerative Conditions.

These conditions are characterized by a progressive deterioration in quality, function, or structure of the eye, leading to a progressive decrease in visual acuity.

Examples of degenerative ocular diseases include dermatochalasis, ptosis, keratitis sicca, Fuch's corneal dystrophy, presbyopia, cataract, wet age related macular degeneration (wet AMD), dry age related macular degeneration (dry AMD); degenerative vitreous disorders, including vitreomacular traction (VMT) syndrome, macular hole, epiretinal membrane (ERM), retinal tears, retinal detachment, and proliferative vitreoretinopathy (PVR).

The general approach and objectives of senolytic therapy for degenerative conditions are based on the following:

Degenerative ocular conditions affect all anatomic locations of the visual system, and are associated with a pathophysiologic cascade that is populated with features of senescence and SASP-related factors induced by a multitude of cellular stressors. These include environmental factors such as UV light exposure and smoking, oxidative stress and inflammatory factors, mitochondrial and DNA damage and extracellular matrix degradation. These stressors are further associated with the secretion and accumulation of SASP-like factors which continue to disrupt the local tissue microenvironment and produce ongoing degenerative changes.

The objective of senolytic therapy is to disrupt this cycle via the elimination of senescent cells and their associated SASP. This would limit ongoing damage in tissue and potentially restore function through improved features of the cellular microenvironment. As an example, senolytic therapy can reduce a range of growth factors known to be implicated in various stages of AMD. A senolytic agent that blocks production of SASP factors can exert a multi-pronged impact to the pathophysiologic course of AMD, and can modulate and potentially reverse the course of disease.

Degenerative disorders of the visual system affect anterior and posterior structures therefore the approach to senolytic delivery for these diseases will include both anterior and posterior delivery mechanisms, depending on the site of the primary pathology.

Dermatochalasis

Dermatochalasis is an age-related change in the upper and lower lids characterized by loose, redundant skin and orbicularis muscle often with bulging of the orbital fat pockets. It may be associated with ptosis of the eyebrows and forehead relaxation. When severe in the upper lids, it can limit peripheral vision and obstruct the central visual axis. The localization, severity and frequency of visually significant ptosis increases with age.

Systemic diseases such as thyroid-related orbitopathy, renal failure, trauma, cutis laxa, Ehlers-Danlos syndrome, amyloidosis, hereditary angioneurotic edema and xanthelasma may predispose a subject to dermatochalasis. In some cases, dermatochalasis is associated with an inherited disorder. Dermatochalasis is caused by a loss of elasticity in the connective tissue supporting the structure of the front portion of the eyelid. The pathophysiology of dermatochalasis is consistent with the normal aging changes seen in the skin. This includes loss of elastic fibers, thinning of the epidermis, redundancy of the skin, and lymphatic dilation. Subjects with dermatochalasis can also have blepharitis, a condition caused by the plugging of glands in the eye that produce lubricating fluid (meibomian glands).

Dermatochalasis can be severe enough that it pushes the eyelashes into the eye, causing entropion. Eyelid deformities, such as upper eyelid entropion and lower eyelid ectropion or retraction, can be observed with redundant upper or lower eyelid skin. The redundant upper eyelid skin overhangs the lashes, causing lash ptosis and entropion with resultant keratitis. In patients with severe lower eyelid dermatochalasis, laxity of the lower eyelid develops with resultant eyelid retraction or ectropion.

Dermatochalasis can lead to visual-field loss. In severe cases of dermatochalasis, a patient can lose 50% or more of their superior visual field. Patients with a purely aesthetic deformity may not experience any visual field defects. Blepharitis is in some cases observed in patients with moderate-to-severe dermatochalasis. Blepharitis is characterized by eyelid skin edema and erythema; scurf; meibomian gland inflammation and plugging; and, occasionally, hordeolum.

Local administration (e.g., via injection or topical administration to the eyelid skin and/or muscle) of the senolytic agent can deliver an effective dose to the subject for the treatment of dermatochalasis. The senolytic agents of this invention can halt progression of dermatochalasis in the subject. In some cases, this invention can halt or reverse at least part of the damage caused prior to treatment.

Ptosis

Ptosis refers to an abnormal position of the eyelid margin, the most common cause of which is aging. Acquired ptosis is a condition where patients have normal eyelids when born and develop droopy eyelids in adulthood. The condition can affect one eye or both eyes and is more common in the elderly, as muscles in the eyelids may begin to deteriorate. In some cases, a person may be born with congenital ptosis and experience early onset of the condition including drooping of either one of both eyelids.

Ptosis occurs due to dysfunction of the muscles that raise the eyelid or their nerve supply. Depending upon the cause, ptosis can be classified into several types: Neurogenic ptosis which includes oculomotor nerve palsy, Horner's syndrome, Marcus Gunn jaw winking syndrome, third cranial nerve misdirection; Myogenic ptosis which includes oculopharyngeal muscular dystrophy, myasthenia gravis, myotonic dystrophy, ocular myopathy, simple congenital ptosis, blepharophimosis syndrome; Aponeurotic ptosis which may be involutional or post-operative; Mechanical ptosis which occurs due to edema or tumors of the upper lid; Neurotoxic ptosis; and Pseudo ptosis.

The primary symptom of ptosis is a visible drooping or sagging of the upper eyelid, in one or both eyes. Ptosis generally gives the face a tired or severe appearance. Ptosis can also result in dry eyes or watery eyes, as the eyelids are no longer functioning effectively to keep the eyes moist. Severe ptosis can lead to visual field loss. In some cases, the subject experiences tiredness and aching around the eyes, as the eyebrows are constantly lifted in order to see properly.

Local administration can be done via injection or topical administration to the eyelid skin and/or muscle). In some cases, a senolytic agent can reverse or halt at least part of the damage caused by the condition.

Keratitis Sicca

Keratitis sicca is a condition characterized by dryness of the conjunctiva and/or cornea. Keratitis sicca is also referred to as keratoconjunctivitis sicca, dry eye, dry eye syndrome, dry eye disease (DED) or dysfunctional tear syndrome. Specific subtypes that fall within the scope of keratitis sicca include aqueous-deficient DED, evaporative DED, Sjögren syndrome, lacrimal gland insufficiency and Meibomian gland disease.

In some cases, keratitis sicca occurs due to inadequate tear production and may be referred to as aqueous tear-deficient dry eye or aqueous-deficient DED. Aqueous tear-deficient dry eye can be found among postmenopausal women or in subjects suffering from an autoimmune disorder or disease such as rheumatoid arthritis, systemic lupus erythematosus (lupus) or Sjögren syndrome. In certain cases, keratitis sicca occurs due to an abnormality of tear composition that results in rapid evaporation of the tears and as such may be referred to as evaporative dry eyes. Drying of the eye can also result from the eyes being partly open for periods of time at night (e.g., in a subject affected with nocturnal lagophthalmos) or from an insufficient rate of blinking (e.g., as can occur in subjects with Parkinson's disease). Damage to the surface of the eye that can result from the condition of keratitis sicca can include increased discomfort and sensitivity to bright light.

Symptoms of keratitis sicca may include eye irritation, stinging, burning, pain or soreness, itching, a pulling sensation, pressure behind the eye; a dry, scratchy, gritty, or sandy feeling in the eye; foreign body sensation, sensitivity to bright light, blurred vision, increased blinking, eye fatigue, photophobia, redness, mucus discharge, contact lens intolerance and excessive reflex tearing. Foreign body sensation refers to a sensation or feeling as if something is in the eye. In certain instances, a subject can experience blurred vision or eye irritation that is severe, frequent, and/or prolonged in duration. In some subjects with severe dry eye, the surface of the cornea can thicken, and/or ulcers and scars can develop. In some cases, blood vessels can grow across the cornea and impair vision.

Not all subjects suffering from keratitis sicca exhibit all symptoms. The subject may complain of an uncomfortable or burning sensation of the eyes. Photophobia or blurred vision may even be present in severe cases. The medical history of the patient may also be suggestive of dry eyes, for example in a patient with a pre-existing diagnosis of acne rosacea, radiation therapy, rheumatoid arthritis, systemic lupus erythematosus, or scleroderma, or other autoimmune disorder. Biomicroscopic examination with a slit lamp can be performed to detect meibomitis, conjunctival dilation, decreased tear meniscus, increased tear debris, mucus strands or staining patterns consistent with keratitis sicca. A tear breakup time of less than 10 seconds may also be assessed, and the Schirmer test can be performed to identify subjects who would benefit from treatment.

The senolytic may be delivered via topical administration to the site affected by the keratitis sicca, e.g., to the conjunctiva and/or cornea: for example, via eye drops, ointment, gel or via controlled sustained release from a contact lens installed on the outside of the eye. Delivery via punctal plug systems or direct injection in to the meibomian or lacrimal glands may also be considerations for delivery of the senolytic agent. An improvement in the condition may include reduction of inferior corneal fluorescein staining, improvement in a Schirmer test, or improvement in signs and/or symptoms of dry eye syndrome. Improvements may be measured using the Ocular Surface Disease Index, or the Ocular Comfort Index.

Fuch's Corneal Dystrophy (FCD)

Fuch's corneal dystrophy is a leading cause of corneal transplantation and affects 5% of the US population over the age of 40 years. It is characterized by a progressive loss of endothelial cells and corneal deposition of an abnormal cellular matrix. The cornea progressively swells and clouds as remaining endothelial cells are insufficient to dehydrate the cornea and maintain its clarity. Increased protein expression of known senescence-related genes CDKN1A and CDKN2A have been demonstrated (Matthaei et al, 2014). Symptoms of FCD include blurred vision and haze and may be associated with pain and corneal blistering. Diagnosis is made through standard ophthalmic tests as outlined previously, and corneal thickness can be measured with corneal pachymetry. Currently available therapies include topical drops and surgical intervention with partial or total penetrating keratoplasty. Administration of a senolytic agent can be achieved by local delivery to the cornea or to the anterior chamber adjacent to the cornea in the eye: for example, by intracameral injection, or via an ocular implantable device. This may halt progression or reverse at least part of the damage caused prior to treatment.

Presbyopia

Presbyopia is a condition directly associated with aging, and is nearly universal as middle age is reached. Presbyopia is associated with aging of the eye and results in progressively worsening ability to focus clearly on close objects. It is due to hardening and loss of flexibility of the lens of the eye causing the eye to focus light behind rather than on the retina when looking at close objects. Lens hardening can be the result of decreasing levels of alpha-crystallin in the lens. Weakening of the ciliary body muscle fibers may also contribute to the inability of the ciliary muscle to deform the lens and cause presbyopia. Senolytic administration may strengthen the ciliary muscle through elimination of senescent cells and subsequent decrease in muscle fibrosis that occurs with age.

Symptoms include refractive errors, difficulty reading small print (e.g., in low light conditions), requirement to hold reading material farther away, blurring of near objects, eyestrain, headaches and tiredness when performing tasks requiring near vision. Diagnosis can be performed by an ophthalmologist eye examination including tests for assessing vision and ability to focus on and discern objects.

Administration can be done by local delivery to the lens or to a chamber adjacent to the lens in the eye: for example, by intracameral injection, intravitreal injection, or via an ocular implantable device. This may halt progression or reverse at least part of the damage that has occurred.

Cataracts

Cataracts remain the largest cause of global blindness, accounting for 18 of the 39 million blind individuals worldwide. The incidence is known to increase with age and there is no region in the world that is immune to the age-related onset or impact of vision threatening lens opacity.

A cataract is an opacification of the lens of the eye that causes a progressive, painless loss of vision. Cataracts can be classified by their location. A subcapsular cataract occurs at the back of the lens. People with diabetes or those taking high doses of steroid medications can have a greater risk of developing a subcapsular cataract. A nuclear cataract forms deep in the nucleus (e.g., a central zone) of the lens and can be associated with aging. A cortical cataract is characterized by white, wedge-like opacities that start in the periphery of the lens and work their way to the center in a spoke-like fashion. Cortical cataracts can occur in the lens cortex, which surrounds the central nucleus.

A normal lens inside the eye works much like a camera lens, receiving and focusing light onto the retina for clear vision. The lens also adjusts the eye's focus, letting us see things clearly both up close and far away. The lens is composed primarily of water and protein that is assembled into a highly ordered, interactive macro-structure essential for lens transparency and refractive index. Disruption of intra- or inter-protein interactions can alter this structure, exposing hydrophobic surfaces, and causing protein aggregation associated with cataract formation. Over time, a cataract may grow larger and cloud more of the lens, blocking some light from passing through the lens and scattering the light, preventing crisp focus on the retina.

A number of risk factors are associated with formation of cataracts, including but not limited to, ultraviolet radiation exposure, diabetes, hypertension, obesity, smoking, prolonged use of corticosteroid medications, statin medicines used to reduce cholesterol, previous eye injury or inflammation, previous eye surgery, hormone replacement therapy, significant alcohol consumption, high myopia, family history. In some cases, cataracts are associated with oxidative disorders. Senile cataract is an age-related, vision-impairing disease characterized by gradual progressive thickening of the lens of the eye. As outlined throughout this application, all of these risk factors may be associated with the induction of senescence and SASP factors contributing to the development of disorders of the visual system.

Symptoms that may be associated with cataracts include decreased visual acuity, glare (e.g., seeing halos and starbursts around lights), myopic shift and monocular diplopia. In some cases, the symptoms are exhibited by one or more of the following: difficulty reading because of a worsening ability to distinguish the contrast between the light and dark of printed letters on a page, needing more light to see well, problems distinguishing dark blue from black, blurred vision, colors appearing more yellow and less vibrant, and mild double vision (also called ghost images). In certain instances, cataracts can swell and increase the pressure in the eye, causing glaucoma.

A cataract is identified via examination of the eye as outlined previously. Diagnostic methods specific to cataract formation include: 1) Examination of the ocular adnexa and intraocular structures, which may provide clues to the patient's cataract etiology, concomitant disease, and eventual visual prognosis; 2) Swinging flashlight test to detect a Marcus Gunn pupil or a relative afferent pupillary defect (RAPD) indicative of optic nerve lesions or diffuse macular involvement which may be alternate causes of decreased vision; 3) Examination of nuclear size and brunescence (after dilation, nuclear size and brunescence as indicators of cataract density can be determined prior to phacoemulsification surgery); 4) Direct and indirect ophthalmoscopy—To evaluate the integrity of the posterior segment; or 5) genetic testing for a disease that predisposes a subject to development of a cataract.

A senolytic agent may be effective in preventing development of cataracts, reversing cataracts in a patient, reducing cataract severity, or increasing lens clarity. Administration can include local delivery to the lens or to a chamber of the eye adjacent to the lens, via intraocular or intracameral injection, or via an ocular implantable device. This can eliminate the need for conventional cataract surgery on the eye. In general, the method is performed without surgical removal of the lens or a portion thereof.

Age-Related Macular Degeneration (AMD)

Macular degeneration refers to a family of diseases that are characterized by a progressive loss of central vision associated with abnormalities of Bruch's membrane, the choroid, the neural retina and/or the retinal pigment epithelium. AMD can be classified into two types: dry macular degeneration and wet macular degeneration. Dry AMD is defined by the gradual loss of retinal pigment epithelial (RPE) and photoreceptor cells in the macula. Wet AMD is characterized by the growth of abnormal blood vessels beneath the macular epithelium. Age-related developmental changes in retinal morphology and energy metabolism, as well as cumulative effects of environmental exposures may render the neural and vascular retina and retinal pigment epithelium more susceptible to damage in late adulthood. The pathogenesis of age-related macular degeneration may be related to different processes associated with aging, including oxidative stress, mitochondrial dysfunction, and inflammatory processes.

Dry AMD (also referred to as nonexudative AMD) is a broad designation, encompassing all forms of AMD that are not neovascular and including early and intermediate forms of AMD, and an advanced form of dry AMD known as geographic atrophy or atrophic AMD. In geographic atrophy, progressive and irreversible loss of retinal cells leads to a loss of visual function. AMD-like pathology is characterized by a progressive accumulation of characteristic yellow deposits, called drusen (e.g., a buildup of extracellular proteins and lipids), in the macula, between the retinal pigment epithelium and the underlying choroid which is believed to damage the retina over time.

Dry AMD patients can have minimal symptoms in earlier stages of the disease. In approximately 10-20% of subjects, dry AMD progresses to the wet type of AMD. Patients who are affected by dry AMD have gradual loss of central vision due to the death of photoreceptor cells and their close associates, retinal pigmented epithelial (RPE) cells, with deposition of drusen. Photoreceptors, the cells in the retina that actually 'see' light, are essential for vision. RPE cells are necessary for photoreceptor survival, function and renewal. The RPE cells in the eye act as macrophages, which phagocytize and recycle components of the membranous outer segments of photoreceptors. If the mitochondria within the RPE cells are damaged, photoreceptor recycling is inhibited, with resultant accumulation of drusen. Drusen accumulation causes physical displacement of the RPE from its immediate vascular supply, the choriocapillaris. This displacement creates a physical barrier that may impede normal metabolite and cellular waste diffusion between the choriocapillaris and the retina.

Symptoms of dry AMD include drusen, visual distortion, e.g., straight lines appear bent, reduced central vision in one or both eyes, need for brighter light when reading, loss of contrast sensitivity, increased blurriness of printed words, decreased intensity or brightness of colors, difficulty recognizing faces.

The "wet" form of advanced AMD (wet AMD), also referred to as neovascular or exudative AMD, results in vision loss due to abnormal blood vessel growth (e.g., choroidal neovascularization) in the choriocapillaris, through Bruch's membrane. Wet AMD is preceded by the dry form of AMD and both forms commonly co-exist in the same individual—thus both processes may be impacted by simultaneous treatment with a senolytic agent. As the photoreceptor and RPE cells slowly degenerate and breaks from in Bruch's membrane, there is a tendency for blood vessels to grow from their normal location in the choroid into an abnormal location beneath the retina. Choroidal neovascularization (CNV) is stimulated by vascular endothelial growth factor (VEGF). The abnormal blood vessels can be fragile, ultimately leading to blood and protein leakage below the macula. Bleeding, leaking and scarring from these blood vessels eventually causes irreversible damage (e.g., hemorrhage, swelling and scar tissue) and severe loss of central vision to the photoreceptors and rapid vision loss. If left untreated, wet AMD is responsible for approximately 90% of all blindness resulting from AMD.

Symptoms of wet AMD include reduced central vision in one or both eyes, e.g., dark spot (or spots) in the center of their vision, normal side or peripheral vision, straight lines appearing bent, decreased intensity or brightness of colors, a general haziness in the overall vision, well-defined blurry or bling spot in field of vision, abnormal neovascularization, blood leakage in the eye, e.g., behind the macula and abrupt onset or rapid worsening of symptoms.

Eligible subjects may be identified via visual examination of the subject's eye or according to risk-factor criteria. Testing may include Fundus photography, dark adaptation testing, a Pelli Robson test, visual performance tests (e.g., Snellen chart, Amsler grid, Farnsworth-Munsell 100 hue test and Maximum Color Contrast Sensitivity test), preferential hyperacuity perimetry test, electroretinography, optical coherence tomography (OCT), and angiography (e.g., fluorescein angiography) in any combination.

AMD can be characterized into three stages: early, intermediate, and late, based in part on the extent (size and number) of drusen. Early AMD is diagnosed based on the presence of medium-sized drusen, and may be asymptomatic. Intermediate AMD is diagnosed by large drusen and/or any retinal pigment abnormalities. In some cases, intermediate AMD may cause some vision loss, however, it is also usually asymptomatic. In late AMD, enough retinal damage occurs that people have symptomatic central vision loss in addition to drusen. The risk of developing symptoms is higher when the drusen are large and numerous and associated with disturbance in the pigmented cell layer under the macula. Large and soft drusen are thought to be related to elevated cholesterol deposits.

Diagnosis of macular degeneration rests on signs in the macula, irrespective of visual acuity. A variety of procedures and tests can be used in the diagnosis of AMD as outlined previously.

Relevant drusen features used include number, en face area and volume of drusen detected; shape of drusen detected; density of drusen; and reflectivity of drusen. Retinal image data obtained using spectral-domain optical coherence tomography (SD-OCT) can be analyzed. The image data comprise a cross-section of the retina and an en face image of the retina. The image data are processed to obtain an accurate structure showing locations, shape, size, and other data on drusen. This structural information can provide quantitative drusen features that are indicative of a risk of progression of AMD from the dry form to the wet form of the disease in a given subject and defined time period (U.S. Pat. No. 9,737,205).

Optical coherence tomography can also be used in the diagnosis and the follow-up evaluation of the response to treatment. In wet AMD, angiography (e.g., fluorescein angiography) allows for the identification and localization of abnormal vascular processes and can be used to visualize the leakage of blood behind the macula.

Senolytic therapy can be applied to degenerative retinal diseases such as age-related macular degeneration (AMD) as follows. Deposits of abnormal compounds such as lipofuscin in the retinal pigment epithelium (RPE) lead to ongoing accumulation of debris that impacts support of the photoreceptors in the outer retina. In AMD, this occurs secondary to age-related changes in Bruch's membrane, choriocapillaris and retinal pigment epithelium (RPE). As in ischemia-related ocular disease, a complex pathophysiologic cascade is initiated, again with multiple avenues for senolytic therapy to impact disease stabilization and potential regression based on the ability to eliminate senescent cells and their associated SASP.

FIG. 1C (adapted from Kumar and Fu, 2014) shows factors that influence multiple points along the AMD pathophysiologic cascade. The presence of senescent cells in AMD is demonstrated in FIGS. 14A and 14B. FIG. 8 shows the impact of a senolytic agent in senescent RPE cells in accordance with this invention. The potential for the impact of a senolytic therapy on multiple features of both wet and dry AMD is new and unprecedented.

Degenerative Disorders of the Vitreous:

The vitreous body is a clear gel-like substance that fills the cavity of the posterior portion of the eye behind the lens. It is composed of a network of collagen fibrils and helps to stabilize the various retinal layers and retinal vasculature. Over time the vitreous gel collapses secondary to degradation of the collagen fiber network and this puts patients at risk for tractional forces to develop on the underlying retina. These forces are associated with numerous vitreo-retinal diseases, all of which increase with age and syneresis of the vitreous cavity which is known to occur in 70% of patients by the age of 70 years. These vitreo-retinal conditions are outlined below.

Vitreomacular Traction Syndrome

Vitreomacular traction syndrome (VMT) is a disorder of the vitreo-retinal interface characterized by: (i) an incomplete posterior vitreous detachment (PVD), (ii) an abnormally strong adherence of the posterior hyaloid face to the macula; and/or (iii) anteroposterior traction exerted by the syneretic vitreous pulling at adherent sites on the macula causing morphologic and often functional effects. With age, the vitreous gel undergoes liquefaction forming pockets of fluid within the vitreous which leads to a contraction or condensation (syneresis) of the vitreous. With loss of vitreous volume, there is a tractional pull exerted at sites of vitreoretinal and vitreopapillary attachments by means of the condensing dense vitreous cortex. At the same time, there can be a weakening of these attachments between the vitreous and the internal limiting membrane (ILM) leading to detachment of the posterior hyaloid. Symptoms include blurred or reduced vision, metamorphopsia, micropsia, scotoma, and difficulties with daily vision-related tasks such as reading.

Macular Hole

Macular hole is a retinal break that in general involves the fovea. Macular holes are related to aging and usually occur in people over age 60. Macular holes may be caused by tangential traction as well as anterior posterior traction of the posterior hyaloid on the parafovea. Macular holes can occur as a complication of a posterior vitreous detachment at its earliest stages. Risk factors for macular hole include age, myopia, trauma, and ocular inflammation.

Macular holes can begin gradually and develop in three stages: Foveal detachments (Stage I), which can progress without treatment; Partial-thickness holes (Stage II), which can progress without treatment; and Full-thickness holes (Stage III). The size of the hole and its location on the retina can determine how much it will affect vision. When a Stage III macular hole develops, most central and detailed vision can be lost. If left untreated, a macular hole can lead to a detached retina, a sight-threatening condition.

In the early stage of a macular hole, a subject may notice a slight distortion or blurriness in their central vision. Straight lines or objects can begin to look bent or wavy. Reading and performing other routine tasks with the affected eye become difficult. Symptoms of macular holes include, blurred vision, distorted central vision.

Epiretinal Membrane

Epiretinal membrane (ERM, also referred to as cellophane maculopathy or macular pucker) is an avascular, fibrocellular tissue that can develop on the inner surface of the retina. There are multiple cytokines associated with the development and proliferation of ERMs, and an increase of this condition with age and vitreous syneresis.

The tissue is semi-translucent and proliferates on the surface of the internal limiting membrane. In the development of ERM, residual cortical vitreous secondary to a posterior vitreous detachment or partial separation of the posterior hyaloid can allow for the proliferation of glial cells on the retina. In some cases, ERM is an idiopathic condition. In certain cases, inflammatory mediators promote fibrocellular growth in the setting of secondary ERM formation. Secondary ERMs can occur in association with retinal vascular diseases, ocular inflammatory disease, trauma, intraocular surgery, intraocular tumors, and retinal tear or detachment. Other risk factors include age, posterior vitreous detachment, and history of ERM in the fellow eye. Symptoms include painless loss of vision, metamorphopsia (visual distortion, e.g., in which shapes can appears wavy or crooked), double vision, light sensitivity and images appearing larger or smaller than normal.

In some cases, subjects with ERMs have few symptoms and their ERMs are diagnosed incidentally on dilated retinal exam or on retinal imaging such as with ocular coherence tomography (OCT). OCT imaging method can be used to assess the severity of the ERM. Fluorescein angiography can also be used to determine if other underlying retinal problems have caused the ERM.

Retinal Tear and Detachment

Retinal tears can occur as a result of vitreous traction to an area of preexisting vitreoretinal adhesion, most commonly associated with age related vitreous syneresis. In some cases, the retina frequently appearing completely normal before the acute tear event. A retinal tear may occur with or without subsequent retinal detachment. Vitreous humor fills the space in the eye between the lens and the retina. Usually, vitreous humor moves from the retina without causing problems, but in some cases, the movement pulls hard enough to tear the retina in one or more places. Fluid may pass through a retinal tear, lifting or detaching the retina from the back of the eye.

Retinal detachment occurs when subretinal fluid accumulates between the neurosensory retina and the retinal pigment epithelium. This process can occur in three ways. One mechanism involves the occurrence of a break in the retina that allows vitreous to directly enter the subretinal space and is known as a rhegmatogenous retinal detachment. Rhegmatogenous retinal detachments are often related to retinal tears associated with posterior vitreous detachment or trauma. A second mechanism involves proliferative membranes on the surface of the retina or vitreous. These membranes can pull on the neurosensory retina causing a physical separation between the neurosensory retina and retinal pigment epithelium, called a traction retinal detachment.

Tractional retinal detachments can be seen in proliferative retinopathy due to diabetic disease, sickle cell and other disease processes leading to neovascularization of the retina. Tractional retinal detachments can also be due to proliferative vitreoretinopathy after trauma or surgery. The third mechanism for retinal detachment is based on accumulation of subretinal fluid due to inflammatory mediators or exudation of fluid from a mass lesion. This mechanism is known as exudative or serous retinal detachment and can be caused by a number of inflammatory, or exudative retinal disease processes such as sarcoidosis or choroidal neoplasms. Rhegmatogenous retinal detachment has a characteristic appearance differentiating it from a tractional or serous detachment. A rhegmatogenous retinal detachment has a corrugated appearance and undulates with eye movements. Tractional detachments have smooth concave surfaces with minimal shifting with eye movements. Serous detachments show a smooth retinal surface and shifting fluid depending on patient positioning.

Retinal tears and rhegmatogenous and tractional detachments require repair via any or all of laser, cryotherapy, pneumatic retinopexy, scleral buckle and/or vitrectomy.

Proliferative Vitreoretinopathy

Proliferative vitreoretinopathy (PVR) occurs when a scar forms under or on the retina after retinal detachment, preventing the retina from healing and falling back into place. PVR is associated with failed repair of retinal detachment. When there is a hole in the retina, cells that normally reside under the retina enter the eyeball and settle on the inner layer of the eye on top of the retina. These cells multiply and form a scar on the surface (and in some cases under) the retina. This scar tissue then contracts and detaches the retina away from the innermost walls of the eye, resulting in a second retinal detachment.

The senolytic agents of this invention can be administered by intravitreal injection into the vitreous of the eye, or by topical administration.

Type 3: Genetic Conditions

Genetic ophthalmic conditions are characterized as a disease that is caused by a mutation, deletion, or insertion in an individual's DNA sequence.

Genetic disorders can be grouped into three main categories: 1. Single gene disorders: disorders caused by defects in one particular gene, often with simple and predictable inheritance patterns such as dominant, recessive and x-linked. 2. Chromosome disorders: disorders resulting from changes in the number or structure of the chromosomes. 3. Multifactorial disorders (complex diseases): disorders caused by changes in multiple genes, often in a complex interaction with environmental and lifestyle factors such as diet or cigarette smoke.

Examples of genetic ocular diseases include Retinitis Pigmentosa, Stargardt Disease, Best Disease and Leber's hereditary optic neuropathy (LHON).

The general approach and objectives of senolytic therapy for genetic conditions are based on the following:

Genetic disorders of the visual system can affect all ocular anatomic layers, and are associated with cellular defects that may lead to an accelerated aging phenotype, caused or mediated at least in part by senescent cells. An inheritable susceptibility to certain eye diseases suggests that the accumulation of disease-mediating senescent cells may directly or indirectly be influenced by genetic components, which again may lead to earlier presentation. Genetic disorders demonstrate a multifactorial cascade with senescent cells and SASP production contributing to ongoing cell dysfunction and degeneration/death.

These disorders can benefit from senolytic therapy because senescent cells and their associated SASP factors mediate associated contributions to ongoing cell dysfunction, cell loss, and disease progression via blockage of the angiogenic, inflammatory, fibrotic, and extracellular matrix-modifying proteins present in the pathophysiology. Genetic disorders of the visual system affect anterior and posterior structures. A senolytic agent is delivered either into the anterior or posterior region of the eye, or a combination thereof, depending on the site of the primary pathology.

Underlying Pathophysiology

Complex monogenic retinal disorders such as retinitis pigmentosa, Stargardt disease, or disorders of mitochondrial DNA such as Leber's Hereditary Optic Neuropathy, represent diseases with a known genetic basis that may accelerate the accumulation of senescent cells. Diagnosis, clinical monitoring and response to therapy is monitored in these diseases as in ischemic or degenerative diseases, by a combination of functional and structural tests including visual acuity, visual field, intravenous fluorescein angiogram (IVFA), OCT scanning, and electrophysiology including electroretinography (ERG) and visual evoked potential (VEP).

Figure 1D:
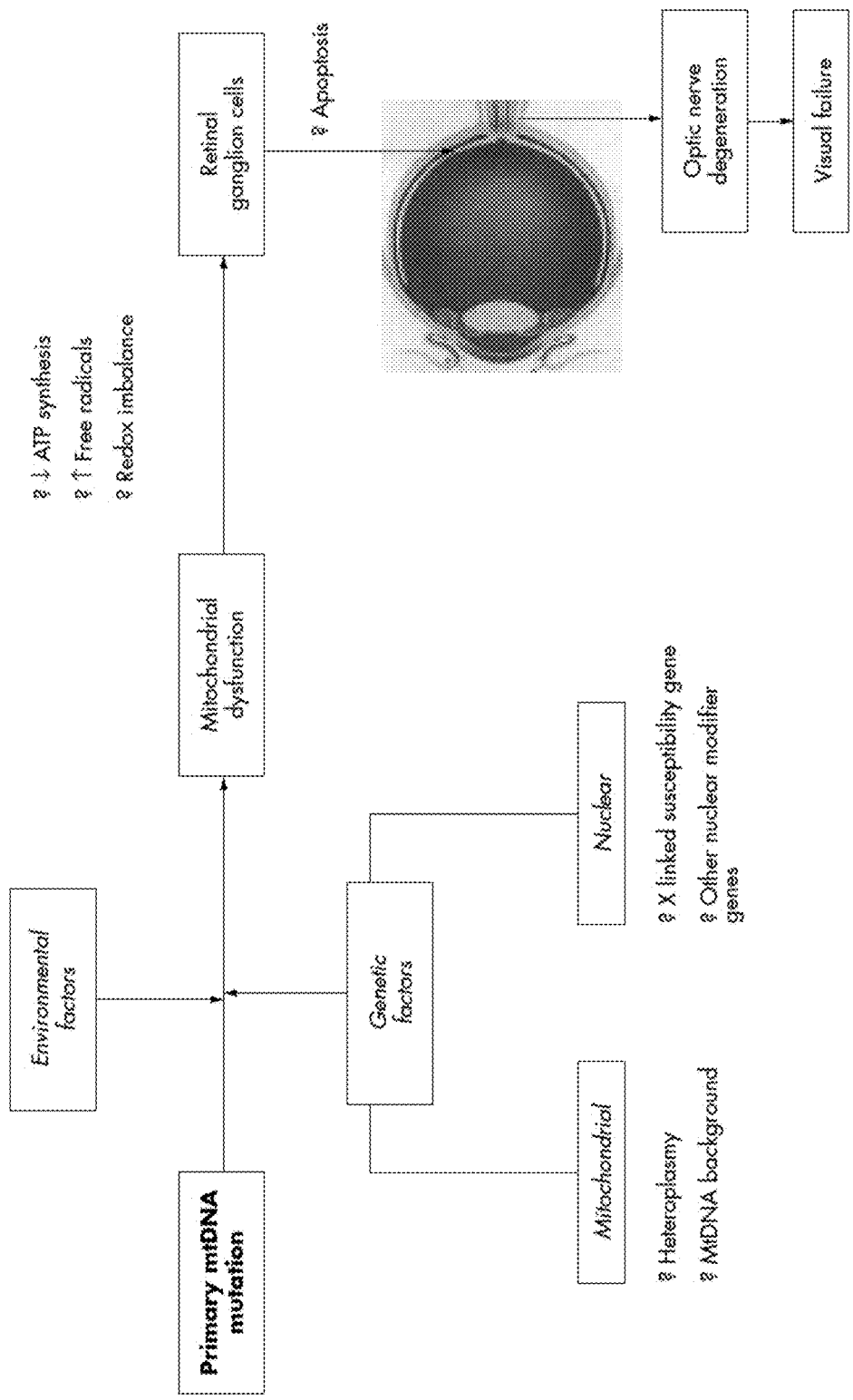

FIG. 1D shows events leading to cell degeneration and cell death in Leber's Hereditary Optic Neuropathy (Mann et al. 2002). FIG. 2A shows retinal cell loss in the clinical stages of Retinitis Pigmentosa (Dryja, 1986). These disorders can benefit from the application of a senolytic via senescent cell and SASP elimination.

In Stargardt disease, lipofuscin accumulation occurs secondary to a mutation in the ABCA4 gene. Diagnosis, clinical monitoring and response to therapy is monitored in these diseases as in ischemic diseases, by a combination of functional and structural tests including visual acuity, visual field, intravenous fluorescein angiogram (IVFA), OCT scanning, and electrophysiology including electroretinography (ERG) and visual evoked potential (VEP).

Retinitis Pigmentosa

Retinitis pigmentosa is a group of inherited disorders that results from harmful changes in any one of more than 200 genes and leads to degeneration of the retina involving a breakdown and loss of cells in the retina. Retinitis pigmentosa is characterized by progressive peripheral vision loss and night vision difficulties (nyctalopia) that can lead to central vision loss. In general, the result of the inherited gene is damage to the photoreceptor cells within the retina. Symptoms of retinitis pigmentosa include nyctalopia, visual loss, e.g., peripheral vision loss, tunnel vision and photopsia (light flashes).

Variability exists in the physical symptoms depending on the particular form of retinitis pigmentosa and not all subjects exhibit all symptoms simultaneously. Diagnostic methods include visual field testing, fundoscopic examination, electroretinogram (ERG) (measures the electrical activity of photoreceptor cells) and genetic testing. Ocular examination can involve assessment of visual acuity and pupillary reaction, as well as anterior segment, retinal, and fundoscopic evaluation. Subjects with retinitis pigmentosa can have a decreased electrical activity, reflecting the declining function of photoreceptors. Additional methods that find use in diagnosing other related diseases can be used to eliminate possible disease diagnoses.

In some cases, a DNA sample from the subject can be used for a genetic diagnosis of retinitis pigmentosa. Particular forms of the disorder can be genetically typed. Genetic testing is available through the National Ophthalmic Disorder Genotyping and Phenotyping Network (eyeGENE).

Stargardt Disease

Stargardt disease (also referred to as Stargardt macular dystrophy, juvenile macular degeneration and fundus flavimaculatus) is an inherited disorder of the retina. Stargardt disease is one of several genetic disorders that cause macular degeneration. Stargardt disease is characterized by excessive lipofuscin accumulation in the retina which causes progressive damage or degeneration of the macula, a small central area of the retina responsible for sharp, central vision.

Vitamin A is used to make light-sensitive molecules inside photoreceptors. Mutations in a gene called ABCA4 are the most common cause of Stargardt disease. This gene makes a protein that normally clears away potentially harmful vitamin A byproducts inside photoreceptors. Affected cells accumulate clumps of lipofuscin, a fatty substance that forms yellowish flecks. As the clumps of lipofuscin increase in and around the macula, central vision can become impaired. Eventually, these fatty deposits lead to the death of photoreceptors and vision becomes further impaired.

Symptoms of Stargardt disease include gray, black, or hazy spots in the center of their vision; lipofuscin deposits; color blindness, bright light sensitivity, long adjustment times moving from light to dark environments. The progression of symptoms in Stargardt disease can vary for each subject. Subjects with an earlier disease onset generally have more rapid vision loss. Vision loss may decrease slowly at first, then worsen rapidly until it levels off. Subjects with Stargardt disease can end up with 20/200 vision or worse. People with Stargardt disease may also begin to lose some of their peripheral vision as they get older.

Diagnostic methods that can be used to assess symptoms of vision loss in Stargardt disease include examination and ancillary testing as outlined previously and include visual field testing, color testing, fundus examination, electroretinography (ERG), optical coherence tomography (OCT) and genetic testing. The number, size, color, and appearance of lipofuscin deposits can be variable from subject to subject. The lipofuscin deposits can be observed as yellowish flecks in the macula. The flecks are generally irregular in shape and extend outward from the macula in a ring-like pattern.

Accumulation of lipofuscin may be a direct cause of RPE and photoreceptor demise in the retina. The senolytic agents of this invention may preserve vision in Stargardt disease patients affected by excessive accumulation of lipofuscin.

Best Disease

Best disease (also referred to as vitelliform macular dystrophy) is a form of early onset macular degeneration that is characterized by the appearance of lipofuscin deposits, e.g., in the retinal pigment epithelium layer of the macula. The lipofuscin deposits can appear as yellow or orange yolk-like or egg-like lesions. Abnormalities in the eye result from a disorder in the retinal pigment epithelium (RPE). A dysfunction of the protein bestrophin results in abnormal fluid and ion transport by the RPE. Lipofuscin can accumulate within the RPE cells and in the sub-RPE space, particularly in the foveal area. The RPE of a subject can degenerate over time and in some cases, lead to secondary loss of photoreceptor cells. In some cases, a breakdown of RPE/Bruchs membrane can lead to development of choroidal neovascularization.

Symptoms of Best disease include bilateral macular large yellow lesions with egg-like appearance, mild vision loss in the early stages, moderate vision loss in the late stages, choroidal neovascular membrane (CNVM) and sub-retinal hemorrhage that occurs with mild ocular trauma.

Diagnostic methods include those outlined previously such as electrooculography (EOG), electroretinography (ERG), optical coherence tomography (OCT), angiography (e.g., fluorescein angiography) and fundus autofluorescence imaging. Fundus autofluorescence (FAF) can be used to show hyperautofluorescence during the earlier vitelliform stages of the disease. This hyperfluorescence can settle with the pseduohypopyon stage, becomes mottled with areas of hypoautofluorescence during the vitelleruptive stage, and eventually become hypofluorescent during the atrophic stage of the disease. Changes seen with FAF may precede or appear more striking than with ophthalmoscopy.

Treatment with a senolytic agent may halt or reverse the effect of lipofuscin-associated damage.

Leber's Hereditary Optic Neuropathy (LHON)

Leber's hereditary optic neuropathy (LHON) is a mitochondrial genetic disease characterized by bilateral loss of central vision owing to focal degeneration of the optic nerve. The onset of visual loss ranges from age 8 to 60 but occurs mostly between the age of 15 and 30 years. However, visual deterioration can already occur during the first seven years of life. The disease predominantly affects males.

Symptoms of a subject suffering from LHON include blurring or clouding of vision, loss of visual acuity, loss of central vision, impairment of color vision, centrocecal scotomas, temporal pallor of the optic disc, circumpapillary telangiectatic microangiopathy, sparing of pupillary light responses, swelling of the retinal nerve fiber layer around the disc (pseudoedema) and optic atrophy. LHON subjects can remain asymptomatic until experiencing blurring or clouding of vision in one eye, in some cases, the second eye becoming affected with a delay of about six to eight weeks. LHON patients can experience a rapid and painless loss of central vision accompanied by the fading of colors especially in the green/red field. Visual acuity can reach levels of 20/400, e.g., in a few months. Optic atrophy is a characteristic of the disease and can occur after about 6 months.

Diagnostic methods include fundoscopic examination, fluorescein angiography and optical coherence tomography (OCT). At fundus examination, characteristic signs of the disease include vascular tortuosity of the central retinal vessels, circumpapillary telangiectatic microangiopathy and swelling of the retinal nerve fiber layer around the disc. Fluorescein angiogram may be performed to rule out true optic nerve edema. In some cases, no dye leakage is noted along the borders of an otherwise swollen-appearing optic nerve head. OCT of the optic nerve may show elevation in initial phases of the disease, or atrophy in later stages of the disease.

Type 4: Infectious Ophthalmic Conditions.

These are diseases caused by pathogenic microorganisms, such as bacteria, viruses, parasites or fungi; the diseases can be spread, directly or indirectly, from one person to another.

Infectious ocular diseases can be caused by bacterial agents, fungal agents, or viruses. Etiologic agents include herpes zoster varicella (HZV), herpes simplex, cytomegalovirus, and human immunodeficiency virus (HIV).

The general approach and objectives of senolytic therapy for infections conditions can be based upon the following:

Infectious disorders of the visual system impact all anatomic locations of the eye and are closely associated with aging and senescence. Infectious agents may contribute to the induction of senescence and a multifactorial cascade with senescent cells and SASP production contributing to ongoing cell dysfunction. Once present, senescent cells may in turn impact the ability to fight infection.

Senescent cells have an impaired ability to control viral replication (Kim et al, 2016), which is in line with the known increased susceptibility to infection that occurs with age. Senescence and the ability to respond to infectious agents are a category of ocular disease that can be significantly impacted by senolytic therapy. Elimination of senescent cells and their associated SASP factors can ameliorate damage to the cellular microenvironment. Infectious disorders of the visual system affect anterior and posterior structures. Thus, the senolytic agent is administered to the anterior or posterior compartment, or a combination thereof, depending on the site of the primary pathology.

Herpes Simplex-Associated Ophthalmic Disease

A senolytic agent can be used in treating a subject for viral induced senescence caused by herpes simplex-associated ophthalmic disease. The herpes simplex viruses (e.g., herpes simplex 1) are present in most adults. The viruses in the herpes family are usually located around nerve fibers in humans. Herpes viruses can infect the eye to cause inflammation and scarring of the cornea. Herpes of the eye can be transmitted through close contact with an infected person whose virus is active. Ranging from a simple infection to a condition that can cause blindness, there are several forms of ocular herpetic infection. Herpes keratitis is a viral corneal infection that generally affects the epithelium of the cornea. Stromal keratitis occurs when the infection goes deeper into the layers of the cornea and can lead to scarring and/or loss of vision. Stromal keratitis may be related to a late immune response to the original infection. Iridocyclitis is a serious form of infection where the iris and surrounding tissues inside the eye become inflamed, causing severe sensitivity to light, blurred vision, pain and red eyes. When infection occurs in the retina or the inside lining of the back of the eye, it can be referred to as herpes retinitis.

Symptoms include pain in and around only one eye, headache and fever, redness, rash or sores on the eyelids and around the eyes, especially on the forehead or tip of the nose, redness of the eye, blurry vision, inflammation or swelling and/or cloudiness of the cornea, feeling of dirt or grit in the eye, overflowing tears, pain when looking at bright light. Diagnostic methods include those previously outlined. In some cases, a Tzanck smear or Wright stain test can be used to determine whether lesions that are present contain herpes-type virus. Viral culture, direct immunofluorescence assay, and/or PCR methods may also be used to confirm the diagnosis of infection with a particular virus.

The senolytic agent can be administered by local topical administration to the site affected by the infection e.g., to the conjunctiva and/or cornea to treat, ameliorate, and/or prevent the eye disease. This can be achieved via application of a contact lens that delivers the senolytic within the patient's eye(s) at the site of action; or via intraocular injection to a particular site of infection in the eye. Optionally, the senolytic agent can be administered in combination with an anti-viral agent, which may include oral agents such as acyclovir, famciclovir or valacyclovir.

Herpes Zoster Ophthalmicus

Herpes varicella zoster virus (HZV) or varicella zoster virus (VZV) is a latent virus of the herpes family usually located around nerve fibers in humans. It is strongly associated with increasing age. Reactivation of the virus in the ophthalmic division of the trigeminal nerve leads to the ocular disease Herpes Zoster Ophthalmicus (ZHOU).

Symptoms include severe chronic pain, vision loss, dermatomal forehead rash, painful inflammation of all the tissues of the anterior and, in some cases, posterior structures of the eye, pain in and around only one eye, headache and fever, redness of the eye, blurry vision, inflammation or swelling and/or cloudiness of the cornea, feeling of dirt or grit in the eye, overflowing tears, pain when looking at bright light.

Subjects to be treated according to this invention can be selected based on a clinical presentation or ophthalmic examination that suggests the presence of HZO. Diagnostic methods include external inspection, visual acuity, visual fields, extra ocular movements, pupillary response, fundoscopy, intraocular pressure, anterior chamber slit lamp exam, and corneal exam with and without staining. In some cases, a Tzanck smear or Wright stain test can be used to determine whether lesions contain herpes-type virus. Viral culture, direct immunofluorescence assay, and/or PCR methods may also be used to confirm the diagnosis of infection with a particular virus.

A senolytic agent can be administered by local topical administration to the site affected by the infection e.g., to the conjunctiva and/or cornea, for example using eye drops, via application of a contact lens, or via intraocular injection to a particular site of infection in the eye. A senolytic agent can be administered in combination with a second agent, such as a corticosteroid or an anti-viral agent, e.g., an agent active against herpes varicella zoster virus, such as acyclovir, famciclovir or valacyclovir. In some cases, the anti-viral agent is administered orally.

Cytomegalovirus Retinitis

Cytomegalovirus (CMV)-associated ophthalmic diseases include CMV retinitis. CMV retinitis is a common opportunistic ocular infection seen most commonly in immune-compromised hosts (HIV, organ transplant) that leads to inflammation of the retina and can attack the light-sensing cells in the retina, leading to loss of vision, and in some cases, blindness. Following primary infection, CMV establishes latent infection in myeloid progenitor cells and intermittent viral reactivation from activated macrophages or dendritic cells, which is brought under control by strong virus-specific CD4+ T-cell and CD8+ T-cell responses. In some cases, patients with HIV become more susceptible to CMV-associated ophthalmic disease when their CD4 count drops below 50 cells/μL. Subjects who are HIV-positive or undergoing immunosuppressive chemotherapy can be susceptible to cytomegalovirus-associated ophthalmic disease.

Symptoms of CMV retinitis include infection in one or both eyes, floaters, flashes, blind spots, blurred vision, loss of peripheral vision and retinal detachment. The diagnosis of CMV retinitis can be confirmed by PCR amplification of viral DNA from a sample of the subject. The CD4+T-lymphocyte count of a sample of the subject can be used to predict and or diagnose the onset of an ocular infection. Patients with low CD4+T-lymphocyte counts should undergo regular ophthalmologic examinations for retinal symptoms of the disease.

A senolytic agent may be administered in the front of the eye using eye drops, via application of a contact lens, or via intraocular injection to a particular site of infection in the eye. In some cases, the senolytic agent is administered in combination with an anti-viral agent such as ganciclovir, valganciclovir, foscarnet or cidofovir.

Human Immunodeficiency Virus (HIV)-Associated Ophthalmic Disease

Human immunodeficiency virus (HIV) can affect the eye either directly or indirectly by means of non-infectious microvascular disorders, or various opportunistic infections. Ophthalmic manifestations of HIV infection may involve the anterior or posterior segment of the eye. The anterior segment can develop tumors of the periocular tissues and a variety of external infections. posterior segments can develop an HIV-associated retinopathy or an opportunistic infection of the retina and/or choroid. ophthalmic manifestations of HIV infection include molluscum contagiosum, herpes zoster ophthalmicus, Kaposi's sarcoma, conjunctival squamous cell carcinoma, trichomegaly, dry eye, anterior uveitis, retinal microvasculopathy, CMV Retinitis, acute retinal necrosis, progressive outer retinal necrosis, toxoplasmosis retinochoroiditis, syphilis retinitis and *Candida albicans* endophthalmitis.

Symptoms may include loss of visual acuity, retinal damage and a variety of other symptoms associated with opportunistic infections of interest. Diagnostic methods include those previously outlined.

In some cases, the CD4+T-lymphocyte count of a sample of the subject is used to predict and/or diagnose the onset of an ocular infection in patients who are HIV positive. In some cases, for patients with early-stage HIV disease (CD4 count>300 cells/μL), ocular syndromes associated with immunosuppression are uncommon.

The senolytic agent can be administered via intravitreal injection to a particular site of infection in the eye, optionally in combination with an anti-retroviral HIV agent or specific antivirals such as valgancyclovir given systemically by injection or oral administration.

Type 5: Inflammatory Conditions

These are conditions characterized by a localized response elicited by injury, foreign object, or destruction of tissues, which serves to destroy, dilute, or wall off both the injurious agent and the injured tissue via the production of pro-inflammatory mediators and the recruitment of immune system cells. The inflammatory response can be provoked by physical, chemical, and biologic agents, including mechanical trauma, exposure to excessive amounts of sunlight, x-rays and radioactive materials, corrosive chemicals, extremes of heat and cold, or by infectious agents such as bacteria, viruses, and other pathogenic microorganisms. Inflammation can be acute or chronic and associated with a known trigger or idiopathic (i.e. not associated with a clear inciting agent). Autoimmune ocular diseases also occur and can be associated with significant visual disability.

Examples of idiopathic posterior inflammatory ocular diseases include punctate choroiditis (PIC), multifocal choroiditis (MIC) and serpiginous choroidopathy. Inflammation can also play a role in ocular disorders associated with other etiologies.

The general approach and objectives of senolytic therapy for inflammatory conditions are based upon the following:

Primary and secondary inflammatory ocular conditions affect all anatomic locations of the visual system, from lids and cornea to optic nerve and visual pathway and can be acute or chronic. They are associated with a pathophysiologic cascade that is densely populated with features of senescence and SASP-related factors. The objective of senolytic therapy is to disrupt the inflammatory cycle via the elimination of senescent cells and their associated SASP. This limits ongoing damage in tissue and potentially restore function through improved features of the cellular microenvironment.

Chronic inflammation is a feature of aging and senescence, and of numerous diseases associated with aging. It therefore plays a role in all of the categories of disease presented thus far. Inflammatory disorders of the visual system affect anterior and posterior structures, and are treated accordingly, depending on the site of the primary pathology.

Punctate Choroiditis (PIC)

PIC is an idiopathic inflammatory disorder of the choroid characterized by multifocal, well-circumscribed, small choroidal lesions, after an infectious cause has been ruled out. Changes in the choroidal circulation related to inflammation may contribute to the pathogenesis of PIC. Symptoms of PIC include blurred vision, photopsia, central and/or peripheral scotomatas and metamorphopsias.

Diagnostic methods include those previously outlined. On fundoscopy, there can be multiple, small, round, yellowish-white punctate lesions, in the absence of signs of intraocular inflammation. SD-OCT can provide structural characteristics of PIC lesions. Autofluorescence images can show hypofluorescence in cicatricial lesions and autofluorescence in active lesions.

The senolytic agent can be administered via intravitreal injection, or via an intravitreal implant in the vitreous of the eye of a subject (e.g., a bioerodible implant). The senolytic agent may be administered in combination with corticosteroids, such as cortisone, dexamethasone, fluocinolone, hydrocortisone, methylprednisolone, prednisolone, prednisone and triamcinolone; immunosuppresants such as rapamycin; VEGF-A antagonists such as bevacizumab and ranibizumab; and antibiotics.

Multifocal Choroiditis (MFC)

Multifocal choroiditis (MFC) is a chronic inflammatory disorder characterized by uveitis (inflammation of the middle layer of the eye) and multiple lesions in the choroid. MFC presents most frequently in female patients with an age range of 6 to 69 years.

Symptoms of MFC include decreased visual acuity, blurry vision, floaters, sensitivity to light, blind spots, eye discomfort, photopsias, perceived flashes of light, photophobia, inflammation in the front, middle and/or back layers of the eye, posterior uveitis, multiple scattered yellow/gray-white spots in the choroid and/or retina. The lesions can range in size from 50 to 1,000 μm and have a distribution in the peripapillary region, within the arcades, and in the mid-periphery of the eye. In some cases, a subject can develop macular and peripapillary choroidal neovascularization or choroidal neovascular membranes (CNVMs), new blood vessels that can cause more severe vision loss.

Diagnostic methods include previously outlined techniques, as well as blood tests to eliminate possibility of a particular virus-associated disease.

The senolytic agent can be administered via intravitreal injection, or via an intravitreal implant. The senolytic agent can be administered in combination with a second active agent, which is administered topically or using an intraocular implant or an intraocular injection. Suitable second agents include corticosteroids, such as cortisone, dexamethasone, fluocinolone, hydrocortisone, methylprednisolone, prednisolone, prednisone and triamcinolone; immunosuppressants such as rapamycin; VEGF-A antagonists such as bevacizumab and ranibizumab; and antibiotics.

Serpiginous Choroidopathy

Serpiginous choroidopathy (also referred to as geographic choroiditis or helicoid peripapillary choroidopathy) is an inflammatory eye condition characterized by progressive destruction of the retinal pigment epithelium (RPE) and choriocapillaris with secondary involvement of the outer retina. Lesions can form in the eye that last from weeks to months, commonly recur, and can involve scarring of the eye tissue. If the centrifugally expanding lesions bypass the fovea, the central visual acuity of the subject can be retained. In the macular variant of serpiginous choroidopathy, patients can initially develop a geographic lesion in the macula causing early and profound visual loss without prior peripapillary activity. The condition develops typically in subjects between age 30 and 70 years and affected patients can show an increased frequency of HLA-B7 and retinal S-antigen associations.

Symptoms of serpiginous choroidopathy include painless unilateral vision loss, blurred vision, metamorphopsia, photopsias, scotomata, central scotoma, or yellowish-white chorioretinal lesions with a serpentine or pseudopodal appearance radiating centrifugally from the optic disc.

Diagnostic methods include imaging techniques as previously outlined.

Optionally, a senolytic agent can be administered in combination with other agents such as cortisone, dexamethasone, fluocinolone, hydrocortisone, methylprednisolone, prednisolone, prednisone and triamcinolone; immunosuppressants such as rapamycin; VEGF-A antagonists if indicated for associated choroidal neovascularization such as bevacizumab and ranibizumab; and antibiotics.

Type 6: Iatrogenic Conditions

Iatrogenic ophthalmic conditions are characterized as disease that is the result of diagnostic and therapeutic procedures undertaken on a patient. Examples of iatrogenic ocular conditions include caused post-vitrectomy cataract, or radiation retinopathy following treatment for a neoplasm.

The general approach and objectives of senolytic therapy for iatrogenic conditions are based on the following:

The induction of senescence by stressors associated with a procedure or therapeutic agent produces a pathophysiologic cascade similar to that seen in other forms of senescence induction. Ocular tissues subject to such stressors may have a higher prevalence of senescent cells, which in turn may lead to presentation of certain eye diseases at an earlier stage, or in a more severe form. The objective of senolytic therapy is to disrupt the senescent cell impact on tissue via the elimination of senescent cells and their associated SASP. This prevents or limit ongoing damage in tissue and potentially restores function through improved features of the cellular microenvironment. Given that in some cases the iatrogenic effect can be predicted, preventive therapy may be achievable.

Iatrogenic disorders of the visual system affect anterior and posterior structures. Thus, the senolytic agent is applied into the anterior or posterior compartment or both, depending on the site of the primary pathology, the nature of the procedure, and the senolytic agent that is chosen for use Post-Vitrectomy Cataract Cataract formation or acceleration can occur after intraocular surgery. Vitrectomy is a microsurgical technique used to gain access to the vitreous cavity and retina, and which is used to treat disorders that affect the posterior segment of the eye. Vitrectomy is associated with co-morbidities that may compromise visual acuity such as retinal detachment, corneal decompensation, and cataract formation or progression. In some cases, the type of cataract that forms or accelerates after vitrectomy is a nuclear sclerotic cataract. In some cases of eyes undergoing vitrectomy, the lens is also removed. Cataracts that develop after vitrectomy can limit visual acuity outcomes to a degree that would result in surgical removal of the lens in an otherwise normal eye. Cataract formation or acceleration after vitrectomy may be associated with light toxicity, oxidation of lens proteins, use of intraocular gas, length of operative time, and increased retrolental oxygen levels.

Symptoms of post-vitrectomy cataracts include decreased visual acuity despite anatomic and/or functional success of a previous vitrectomy surgery, glare, halos, etc. Individuals who have undergone vitrectomy may have lower levels of baseline (pre-cataract) visual acuity due to the underlying nature of their retinal pathology; therefore patients with post-vitrectomy cataract are more likely to present with poorer vision than individuals with typical senile cataracts.

Radiation Retinopathy

Radiation retinopathy is a radiation dose-dependent complication of exposure to radiation, such as external beam radiation or plaque brachytherapy. External beam radiation is used as treatment for nasopharyngeal, paranasal sinus or orbital tumors, where there is limited ability to protect the eye, and can lead to clinically significant radiation retinopathy. Plaque brachytherapy for treatment of intraocular tumors can also cause damage to the immediate retina and choroid. Exposure to radiation may cause preferential loss of vascular endothelial cells with relative sparing of the pericytes. Differential sensitivity between endothelial cells and pericytes may result from direct exposure of the endothelial cells to high ambient oxygen and iron found in the blood which generates free radicals and leads to cell membrane damage, occlusion of capillary beds and microaneurysm formation. The retinal ischemia from areas of retinal non-perfusion ultimately leads to macular edema, microaneurysm neovascularization, macular edema, vitreous hemorrhage and tractional retinal detachment.

Symptoms of radiation retinopathy include decreased vision, floaters, telangiectase, neovascularization, vitreous hemorrhage, hard exudates, cotton wool spots and/or macular edema.

Diagnostic methods include ophthalmic examination of a subject's eye, for example, by angiography and optical coherence tomography (OCT). A fluorescein angiogram can be used to identify and highlight the microvascular features of radiation retinopathy. Indocyanine green angiography can reveal precapillary arteriolar occlusion and areas of choroidal hypoperfusion. Optical coherence tomography (OCT) can find use in evaluating macular edema.

Combination of Senolytic Agents with Approved Standard-of-Care Therapies

Senolytic agents for treating ophthalmic conditions can be combined with other pharmaceutical agents that are approved for clinical use. Since the removal of senescent cells works by a different mechanism from current therapies, the two agents can operate synergistically or additively to minimize the administration schedule and improve outcomes. The senolytic agent will remove senolytic cells in the eye that are promoting persistence and progression of disease-related pathophysiology.

The standard of care for many vascular-related ophthalmic conditions is currently an agent that inhibits vascular endothelial growth factor (VEGF): namely, aflibercept (marketed as EYLEA® by Regeneron Pharmaceuticals). Aflibercept is a recombinant fusion protein consisting of VEGF-binding portions from the extracellular domains of human VEGF receptors 1 and 2, that are fused to the Fc portion of the human IgG1 immunoglobulin.

For neovascular (Wet) Age-Related Macular Degeneration (AMD), the recommended dose for EYLEA is 2 mg (0.05 mL or 50 microliters), administered by intravitreal injection every 4 weeks (monthly) for the first 12 weeks (3 months), followed by 2 mg (0.05 mL) via intravitreal injection once every 8 weeks (2 months). For macular edema following retinal vein occlusion (RVO), the recommended dose for EYLEA is 2 mg (0.05 mL or 50 microliters) administered by intravitreal injection once every 4 weeks (monthly). For diabetic macular edema (DME), the recommended dose for EYLEA is 2 mg (0.05 mL or 50 microliters) administered by intravitreal injection every 4 weeks (monthly) for the first 5 injections, followed by 2 mg (0.05 mL) via intravitreal injection once every 8 weeks (2 months). Although EYLEA may be dosed as frequently as 2 mg every 4 weeks (monthly), additional efficacy was not demonstrated in most patients when EYLEA was dosed every 4 weeks compared to every 8 weeks. Some patients may need every 4-week (monthly) dosing after the first 20 weeks (5 months). For diabetic retinopathy (DR) in patients with DME, the recommended dose for EYLEA is 2 mg (0.05 mL or 50 microliters) administered by intravitreal injection every 4 weeks (monthly) for the first 5 injections, followed by 2 mg (0.05 mL) via intravitreal injection once every 8 weeks (2 months).

Use of a senolytic agent in combination with anti-VEGF therapy is a new paradigm that can impact the disease features in important ways. Anti-VEGF therapy given alone requires frequent administration to prevent progression of disease. Combining anti-VEGF therapy with a senolytic agent may decrease the rate of progression or the rate of recurrence of active disease. It is possible that an anti-VEGF can acutely block the potential for leakage and bleeding and the senolytic agent can impact the CNV sub-acutely and then chronically—with the possibility that the need for combination therapy is reduced or obviated, or that it is used with a greater degree of efficacy in a broader group of patients. This in turn may allow the managing clinician to administer the anti-VEGF therapy on a less frequent basis, with improved visual outcomes.

The combination is expected to improve the response rate, improve outcomes, and reduce the treatment burden and combined cost of therapy. It can also impact aspects of the underlying dry AMD that are not addressed by anti-VEGF therapy. This is evident in long term outcomes of patients with wet AMD treated with anti-VEGF therapy who develop vision loss over time in the absence of active neovascularization, but rather due to atrophy or progression of the underlying dry AMD (Bhisitkul et al., 2015).

A senolytic agent can be combined with other agents that address the underlying pathophysiology or symptomatology of the condition.

Non-pharmaceutical intervention that can be performed in conjunction with senolytic administration includes punctal occlusion to decrease the outflow of tears from the eye. Another example is fitting the subject with scleral or semi-scleral contact lenses that create a fluid-filled layer over the cornea. In some cases, administration of the senolytic is performed in combination with a punctum plug device that blocks a tear duct draining tears from the eye.

In some cases, the eye condition is associated with other inflammatory conditions, and the senolytic agent is administered in combination with antihistamines (such as pheniramine, emedastine, or azelastine), decongestants (such as tetrahydrozoline hydrochloride or naphazoline), or a non-steroidal anti-inflammatory agent (such as nepafenac or ketorolac), corticosteroids (such as fluorometholone or loteprednol), mast cell stabilizers (such as azelastie, cromal, emedastine, ketotifen, Iodoxamine, nedocromil, olopatadine, or pemirolast), or steroids. In some cases, the pharmaceutical composition is administered in conjunction with a second active agent, e.g., a macrolide immunosuppressant such as ciclosporin, tacrolimus, pimecrolimus, everolimus, sirolimus, deforolimus, temsirolimus, and zotarolimus, abetimus, gusperimus, or mycophenolic acid.

If the target eye disease is associated with an infectious bacterial condition (such as meibomian gland infection or corneal infection) the eye drops or ointment can be administered with or in a combination composition that contains an antibiotic, such as ciprofloxacin, erythromycin, gentamicin, ofloxacin, sulfacetamine, tobramycin, or monofloxacin. If the dry eye condition is associated with a viral infection, the senolytic agent can be administered with or in a combination composition with an anti-viral agent such as trifluridine or idoxuridine. In another example, the subject presents with a pre-existing autoimmune disorder. The subject can also be treated with a systemic (for example) oral therapy for the associated condition.

In some instances, the senolytic agent is administered in conjunction with one or more different biologically active agents which may be of the same or different drug classes. Biologically active agents or drugs are selected from: anesthetics and analgesics, antiallergenics, antihistamines, anti-inflammatory agents, anti-cancer agents, antibiotics, antiinfectives, antibacterials, anti-fungal agents, anti-viral agents, cell transport/mobility impending agents, antiglaucoma drugs, antihypertensives, decongestants, immunological response modifiers, immunosuppresive agents, peptides and proteins, steroidal compounds (steroids), low solubility steroids, carbonic anhydrize inhibitors, diagnostic agents, antiapoptosis agents, gene therapy agents, sequestering agents, reductants, antipermeability agents, antisense compounds, antiproliferative agents, antibodies and antibody conjugates, bloodflow enhancers, antiparasitic agents, non-steroidal anti-inflammatory agents, nutrients and vitamins, enzyme inhibitors, antioxidants, anticataract drugs, aldose reductase inhibitors, cytoprotectants, cytokines, cytokine inhibitors, and cytokine protectants, UV blockers, mast cell stabilizers, and anti neovascular agents such as antiangiogenic agents like matrix metalloprotease inhibitors and Vascular endothelial growth factor (VEGF) modulators, neuroprotectants, miotics and anti-cholinesterase, mydriatics, artificial tear/dry eye therapies, anti-TNFα, IL-1 receptor antagonists, protein kinase C-13 inhibitors, somatostatin analogs and sympathomimetics.

Other combinations included in the invention may be found elsewhere in this disclosure.

Definitions

A "senescent cell" is generally thought to be derived from a cell type that typically replicates, but as a result of aging or other event that causes a change in cell state, can no longer replicate. It remains metabolically active and commonly adopts a senescence associated secretory phenotype (SASP) that includes chemokines, cytokines and extracellular matrix and fibrosis modifying proteins and enzymes. The nucleus of senescent cells is often characterized by senescence-associated heterochromatin foci and DNA segments with chromatin alterations reinforcing senescence. Without implying any limitation on the practice of what is claimed in this disclosure that is not explicitly stated or required, the invention is premised on the hypothesis that senescent cells cause or mediate certain conditions associated with tissue damage or aging. For the purpose of practicing aspects of this invention, senescent cells can be identified as expressing at least one marker selected from p16, senescence-associated β-galactosidase, and lipofuscin; sometimes two or more of these markers, and other markers of SASP such as but not limited to interleukin 6, and inflammatory, angiogenic and extracellular matrix modifying proteins.

A "senescence associated" disease, disorder, or condition is a physiological condition that presents with one or more symptoms or signs, wherein a subject having the condition needs or would benefit from a lessening of such symptoms or signs. The condition is senescence associated if it is caused or mediated in part by senescent cells, which may be induced by multiple etiologic factors including age, DNA damage, oxidative stress, genetic defects, etc. Lists of senescence associated disorders that can potentially be treated or managed using the methods and products taught in this disclosure include those discussed in this disclosure and the previous disclosures to which this application claims priority.

A compound is typically referred to as "senolytic" if it eliminates senescent cells, compared with replicative cells of the same tissue type, or quiescent cells lacking SASP markers. Alternatively, or in addition, a compound or combination may effectively be used according to this invention if it decreases the release of pathological soluble factors or mediators as part of the senescence associated secretory phenotype that play a role in the initial presentation or ongoing pathology of a condition, or inhibit its resolution. In this respect, the term "senolytic" is exemplary, with the understanding that compounds that work primarily by inhibiting rather than eliminating senescent cells (senescent cell inhibitors) can be used in a similar fashion with ensuing benefits.

Successful "treatment" of an eye disease according to this invention may have any effect that is beneficial to the subject being treated. This includes decreasing severity, duration, or progression of a condition, or of any adverse signs or symptoms resulting therefrom. In some circumstances, senolytic agents can also be used to prevent or inhibit presentation of a condition for which a subject is susceptible, for example, because of an inherited susceptibility of because of medical history.

A "therapeutically effective amount" is an amount of a compound of the present disclosure that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) at least partially reverses damage caused by the condition prior to treatment.

The terms "infectious eye disease" and "ophthalmic infection" refer to an infection caused by a microorganism or microorganisms in or around an eye or the eye structure which include the eyelids and lacrimal apparatus, the conjunctiva, the cornea, the uvea, the vitreous body, the retina, and the optic nerve.

A "phosphorylated" form of a compound is a compound in which one or more —OH or —COOH groups have been substituted with a phosphate group which is either —OPO$_3$H$_2$, —OC$_n$H$_{2n}$PO$_3$H$_2$, or —OC(=O)C$_n$H$_{2n}$PO$_3$H$_2$ (where n is 1 to 4), such that the phosphate group or groups may be removed in vivo (for example, by enzymolysis). A non-phosphorylated or dephosphorylated form has no such phosphate group.

Unless otherwise stated or required, all the compound structures referred to in the invention include conjugate acids and bases having the same structure, crystalline and amorphous forms of those compounds, pharmaceutically acceptable salts, and dissolved and solid forms thereof, including, for example, polymorphs, solvates, hydrates, unsolvated polymorphs (including anhydrates), conformational polymorphs, and amorphous forms of the compounds, as well as mixtures thereof.

An ophthalmic or ocular disorder is defined for the purposes of this disclosure as a disorder of the visual system. An anterior ocular condition is a disease, ailment or condition that affects or involves an anterior ocular region or site, such as a periocular muscle, an eye lid or an eye tissue or fluid which is located anterior to the posterior wall of the lens capsule or ciliary muscles. A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), visual pathway and blood vessels and nerves which vascularize or innervate a posterior ocular region or site.

Except where otherwise stated or required, other terms used in the specification have their ordinary meaning.

INCORPORATION BY REFERENCE

For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

US 2016/0339019 A1 (Laberge et al.) and WO 2016127135 (David et al.) are hereby incorporated herein for all purposes, including but not limited to the identification, formulation, and use of compounds capable of eliminating or reducing the activity of senescent cells and treating ophthalmic conditions. U.S. Pat. Nos. 8,691,184, 9,096,625, and 9,403,856 (Wang et al.) are hereby incorporated herein by reference in its entirety for all purposes, including the features of compounds in the Bcl library, their preparation and use.

EXAMPLES

Example 1: Measuring Bcl Inhibition

The ability of candidate compounds to inhibit Bcl-2 and Bcl-xL activity can be measured on the molecular level by direct binding. This assay uses a homogenous assay technology based on oxygen channeling that is marketed by PerkinElmer Inc., Waltham, Mass.: see Eglin et al., Current Chemical Genomics, 2008, 1, 2-10. The test compound is combined with the target Bcl protein and a peptide representing the corresponding cognate ligand, labeled with biotin. The mixture is then combined with streptavidin bearing luminescent donor beads and luminescent acceptor beads, which proportionally reduces luminescence if the compound has inhibited the peptide from binding to the Bcl protein.

Bcl-2, Bcl-xL and Bcl-w are available from Sigma-Aldrich Co., St. Louis, Mo. Biotinylated BIM peptide (ligand for Bcl-2) and BAD peptide (ligand for Bcl-xL) are described in US 2016/0038503 A1. AlphaScreen® Streptavidin donor beads and Anti-6×His AlphaLISA® acceptor beads are available from PerkinElmer.

To conduct the assay, a 1:4 dilution series of the compound is prepared in DMSO, and then diluted 1:100 in assay buffer. In a 96-well PCR plate, the following are combined in order: 10 µL peptide (120 nM BIM or 60 nM BIM), 10 µL test compound, and 10 µL Bcl protein (0.8 nM Bcl-2/W or 0.4 nM Bcl-XL). The assay plate is incubated in the dark at room temperature for 24 h. The next day, donor beads and acceptor beads are combined, and 5 µL is added to each well. After incubating in the dark for 30 minute, luminescence is measured using a plate reader, and the affinity or degree of inhibition by each test compound is determined.

Example 2: Measuring MDM2 Inhibition

MDM2 (mouse double minute 2 homolog, also known as E3 ubiquitin-protein ligase) is a negative regulator of the p53 tumor suppressor. Inhibiting MDM2 promotes p53 activity, thereby conferring senolytic activity. The ability of compounds to act as agonists for MDM2 can be measured indirectly in cells by monitoring the effect on p53.

A p53 luciferase reporter RKO stable cell line can be obtained from Signosis Inc., Santa Clara Calif. In the p53 luciferase cell line, luciferase activity is specifically associated with the activity of p53. The cell line was established by transfection of a p53 luciferase reporter vector along with a G418 expression vector, followed by G418 selection.

The assay is conducted as follows. Cells from the reporter cell line are treated for 24 h with the candidate compound. Media is then removed, the cells are washed with PBS, and 20 µL of lysis buffer is added to each well. Cells are shaken for 10 s using a plate reader agitator. Luciferase buffer is prepared and added to the wells. p53 activity is then read using a Victor™ multilabel plate reader (PerkinElmer, San Jose Calif.).

Example 3: Measuring Senolytic Activity Using Senescent Fibroblasts

Human fibroblast IMR90 cells can be obtained from the American Type Culture Collection (ATCC®) with the designation CCL-186. The cells are maintained at <75% confluency in DMEM containing FBS and Pen/Strep in an atmosphere of 3% O$_2$, 10% CO$_2$, and ~95% humidity. The cells are divided into three groups: irradiated cells (cultured for 14 days after irradiation prior to use), proliferating normal cells (cultured at low density for one day prior to use), and quiescent cells (cultured at high density for four day prior to use).

On day 0, the irradiated cells are prepared as follows. IMR90 cells are washed, placed in T175 flasks at a density of 50,000 cells per mL, and irradiated at 10-15 Gy. Following irradiation, the cells are plated at 100 µL in 96-well plates. On days 1, 3, 6, 10, and 13, the medium in each well is aspirated and replaced with fresh medium.

On day 10, the quiescent healthy cells are prepared as follows. IMR90 cells are washed, combined with 3 mL of TrypLE trypsin-containing reagent (Thermofisher Scientific, Waltham, Mass.) and cultured for 5 min until the cells have rounded up and begin to detach from the plate. Cells are dispersed, counted, and prepared in medium at a concentration of 50,000 cells per mL. 100 µL of the cells is plated in each well of a 96-well plate. Medium is changed on day 13.

On day 13, the proliferating healthy cell population is prepared as follows. Healthy IMR90 cells are washed, combined with 3 mL of TrypLE and cultured for 5 minutes until the cells have rounded up and begin to detach from the plate. Cells are dispersed, counted, and prepared in medium at a concentration of 25,000 cells per mL. 100 µL of the cells is plated in each well of a 96-well plate.

On day 14, test Bcl-2 inhibitors or MDM2 inhibitors are combined with the cells as follows. A DMSO dilution series of each test compound is prepared at 200 times the final desired concentration in a 96-well PCR plate. Immediately before use, the DMSO stocks are diluted 1:200 into pre-warmed complete medium. Medium is aspirated from the cells in each well, and 100 µL/well of the compound containing medium is added.

Candidate senolytic agents for testing are cultured with the cells for 6 days, replacing the culture medium with fresh medium and the same compound concentration on day 17. Bcl-2 inhibitors like 001967 are cultured with the cells for 3 days. The assay system uses the properties of a thermostable luciferase to enable reaction conditions that generate a stable luminescent signal while simultaneously inhibiting endogenous ATPase released during cell lysis. At the end of the culture period, 100 µL of CellTiter-Glo® reagent (Promega Corp., Madison, Wis.) is added to each of the wells. The cell plates are placed for 30 seconds on an orbital shaker, and luminescence is measured.

Example 3A: Screening a Compound Library for Bcl Antagonists

Discovery of senolytic agents useful for implementation according to this invention was based on the premise that senescent cells can be killed by inhibiting one or more of the Bcl family of regulator proteins that are anti-apoptotic. A molecule with high affinity and selectivity for a Bcl isoform was hypothesized to be effective in inducing apoptosis in senescent cells but not proliferating or non-senescent cells of the same tissue type. Compounds with these properties would be candidates for development as therapeutic agents for clinical medicine.

A library that was initially constructed that contained several hundred compounds. Synthesis and use of such library are explained in U.S. Pat. Nos. 8,691,184, 9,096,625, and 9,403,856. The library was initially screened elsewhere for compounds that were able to bind or inhibit Bcl-xL and/or Bcl-2. Fifteen compounds were chosen from the initial screening for further analysis. FIGS. 1A, 1B, and 1C show nine of the fifteen compounds.

The chosen compounds were further assayed to quantitatively determine the actual affinity for Bcl-xL, Bcl-2, and Bcl-w with a view to identifying candidate senolytic agents for use in treating age related conditions. FIGS. 2A, 2B, and 2C show the results of the binding assay, with those compounds towards the left of each graph having the highest affinity.

Figure 3A:
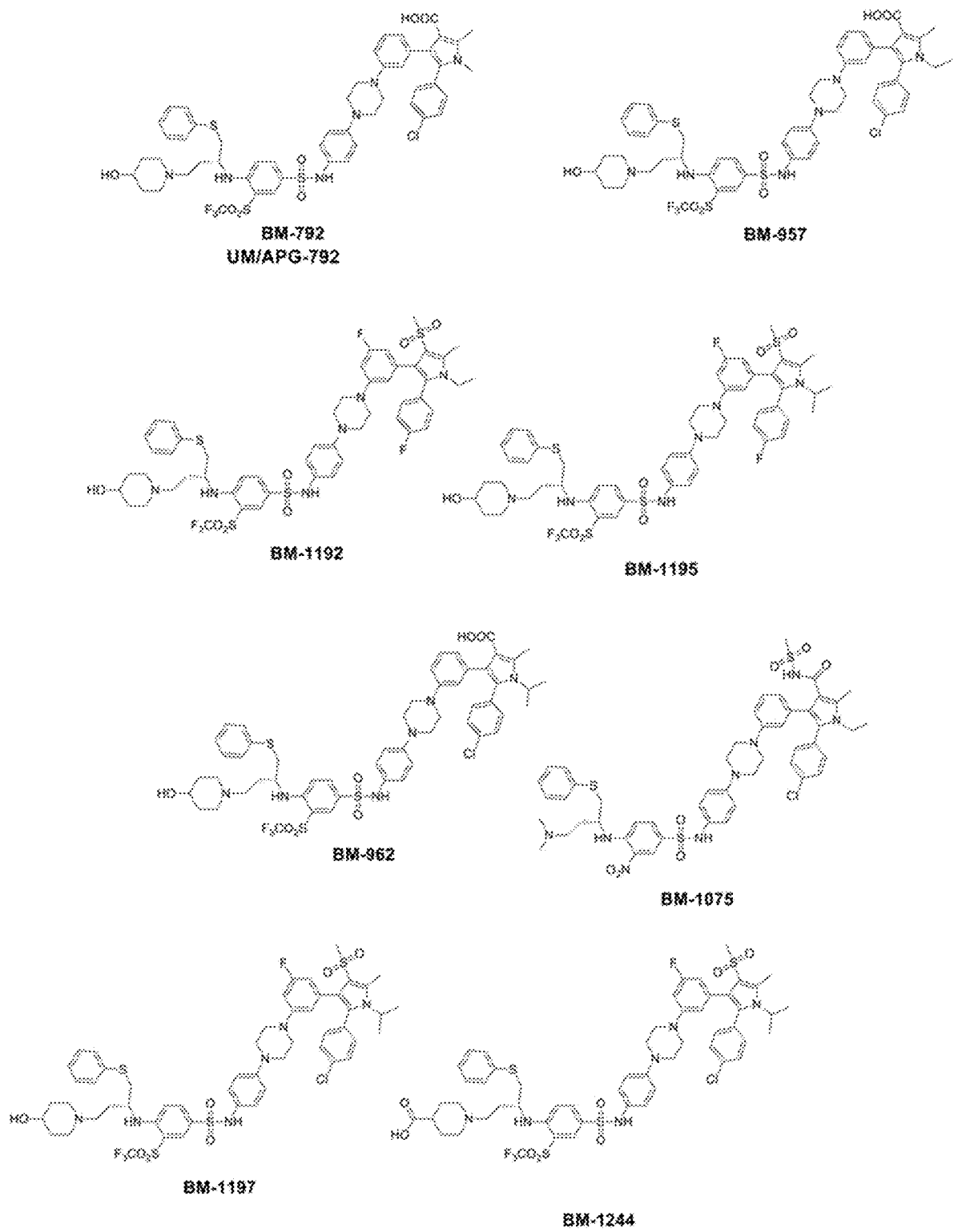
Figure 3B:
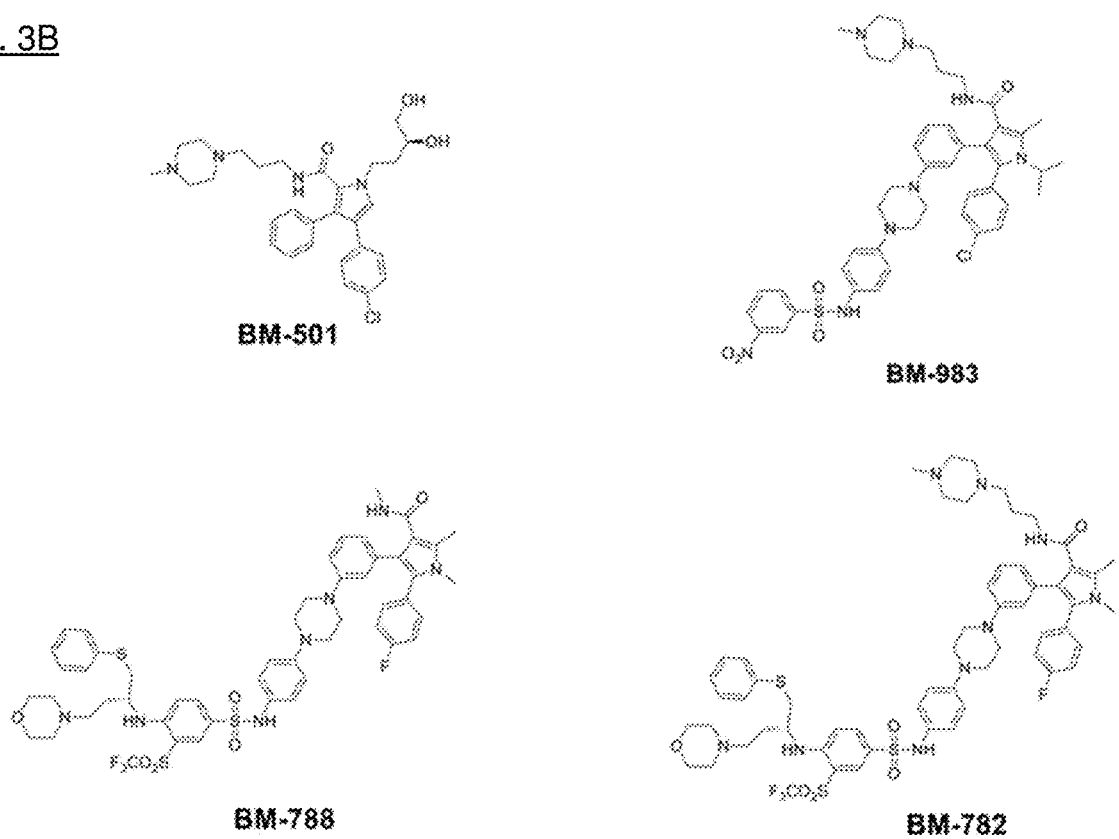

Individual compounds in the library had similar core structures. As shown in FIGS. 3A, 3B, and 3C, the structures of each of the compounds having the most promise were compared with a view to identifying substituents of the molecular structure that were contributing to the desired effect.

Example 3B: Screening High Affinity Bcl Antagonists for Senolytic Potency and Specificity An ability to bind Bcl regulatory proteins does not necessarily mean that the compound is suitable for inducing apoptosis in a clinical setting. Furthermore, even if the compound is potent, it would not be suitable for use as a therapeutic unless it preferentially kills senescent cells with a high degree of selectivity. Accordingly, compounds in the library showing high Bcl binding affinity were further screened for their ability to kill irradiated fibroblasts, in comparison with replicating fibroblasts or fibroblasts that were quiescent (due to confluence) but not senescent.

Figure 4A:
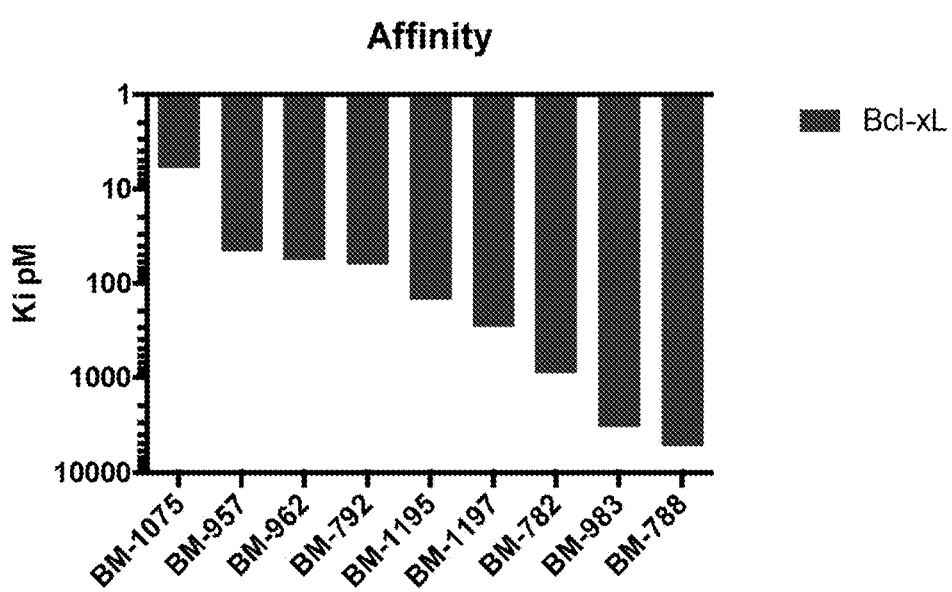
Figure 4B:
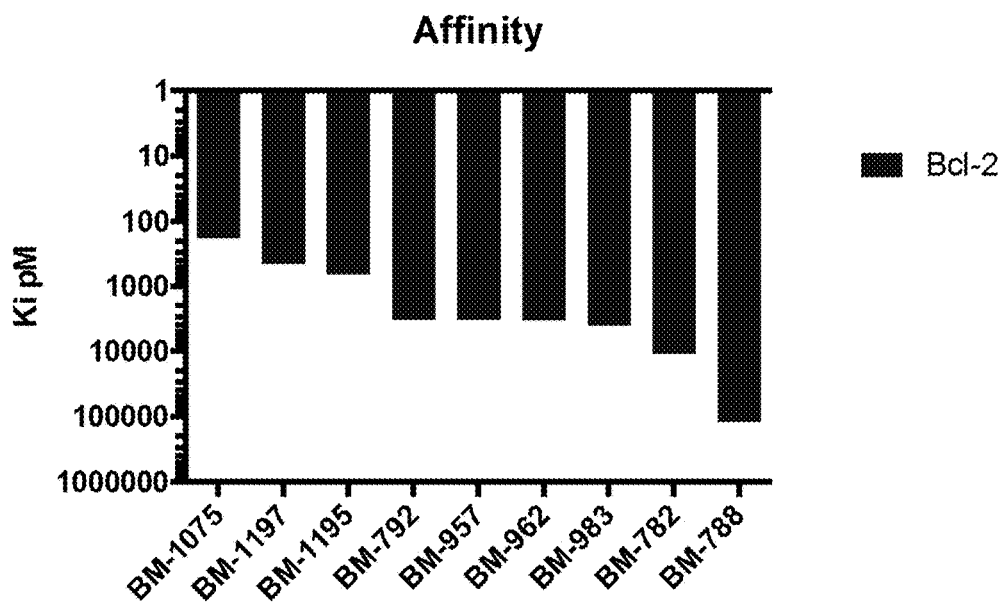
Figure 4C:
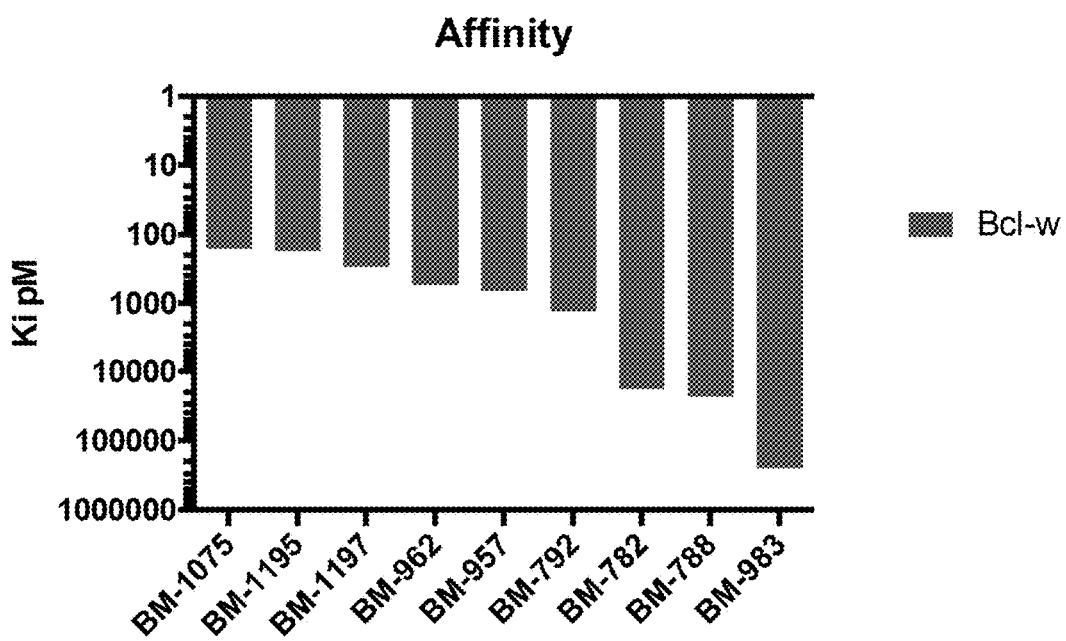
Figure 5A:
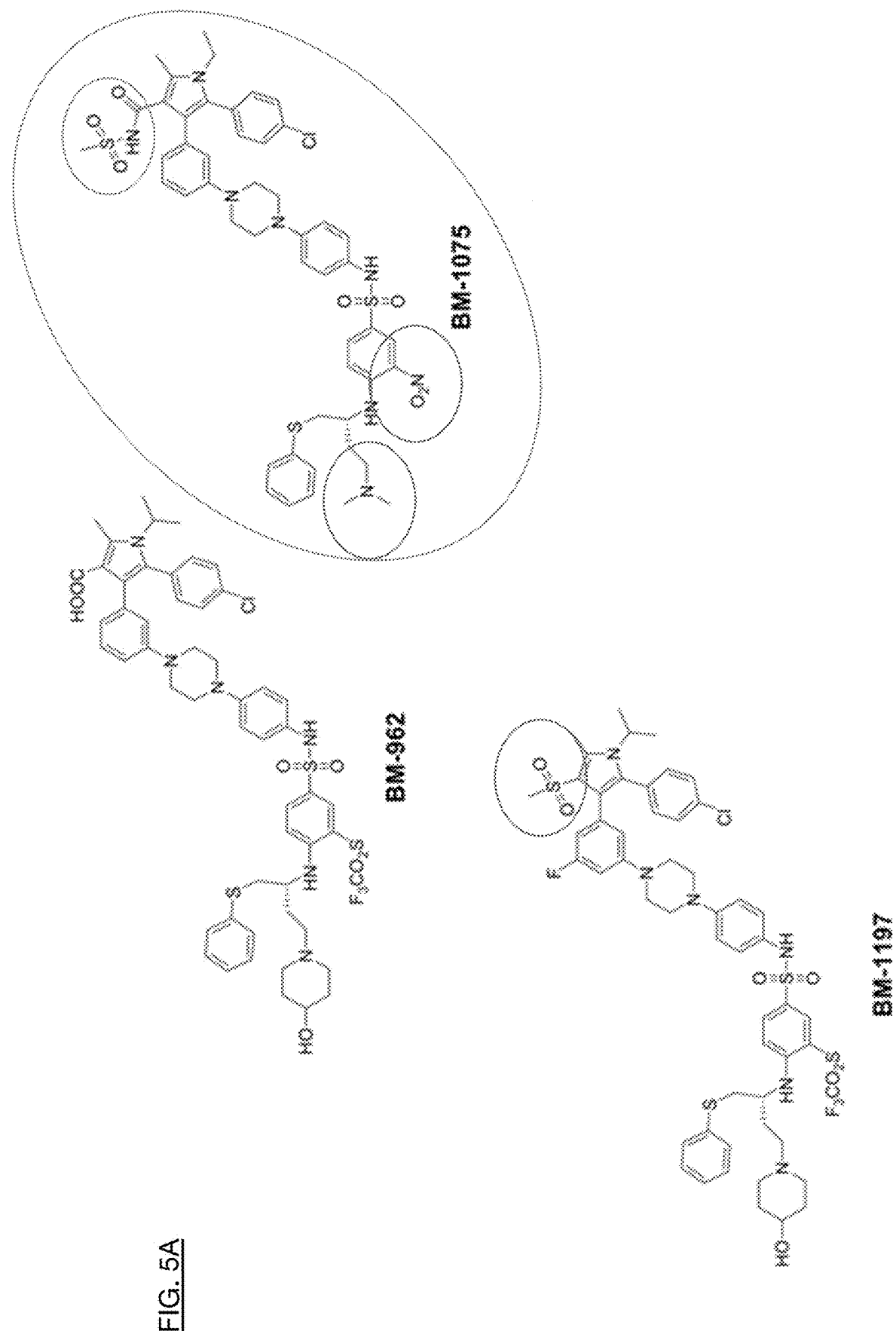
Figure 5B:
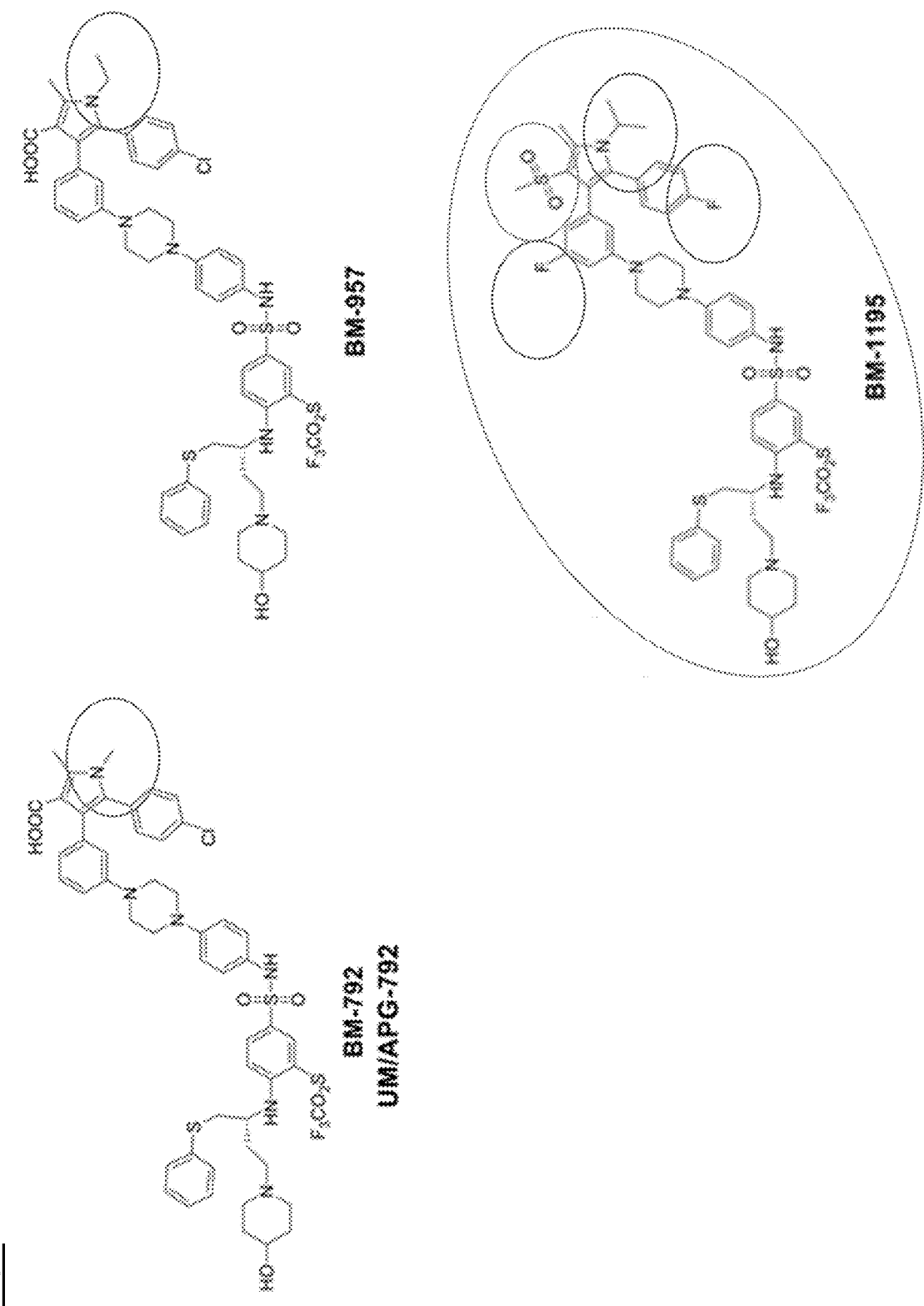
Figure 5C:
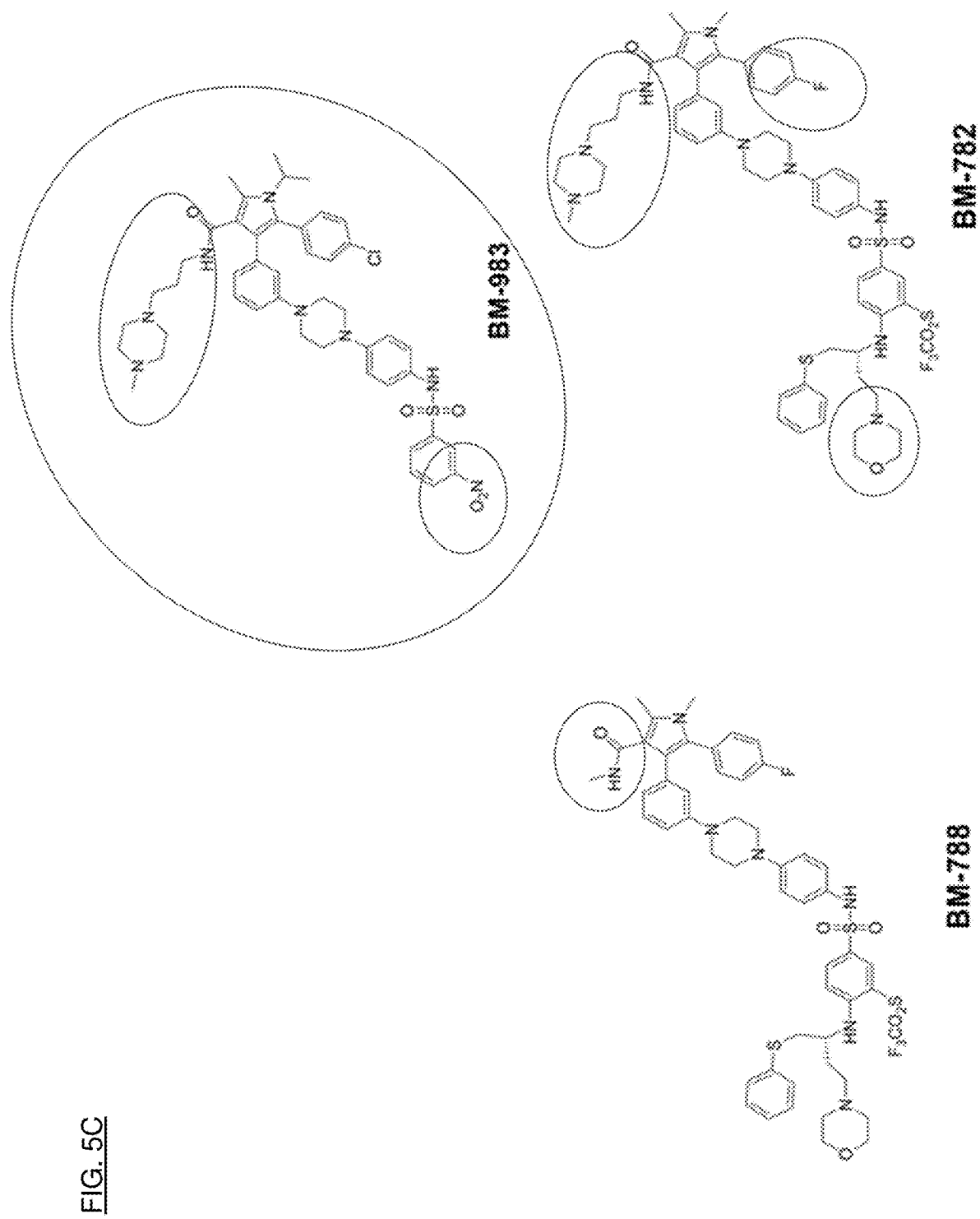
Figure 6:
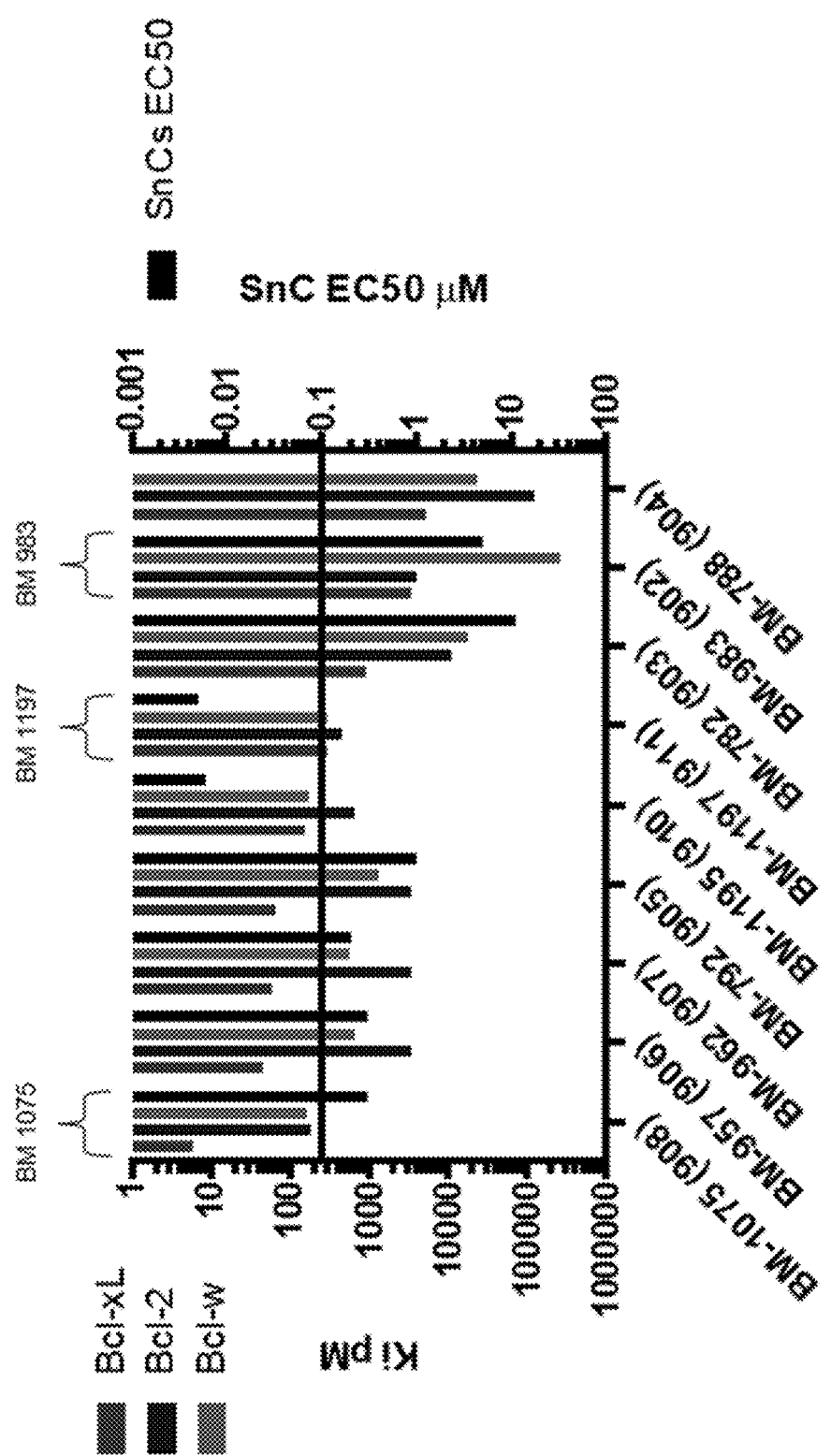
FIG. 6 shows binding affinity to Bcl isoforms, and the effective concentration (EC$_{50}$) for killing senescent fibroblasts (SnCs) in culture.

FIG. 4 shows data obtained from the nine model compounds: affinity of binding to each of the Bcl isoforms, and the effective concentration ($EC_{50}$) for killing senescent fibroblasts (SnCs) in culture. The data are summarized in TABLE 1, below.

| | | | Binding Affinities ($K_i$ ± SD) | | | Best | |
|---|---|---|---|---|---|---|---|
| IDs | Original IDs | Molecular Weight | Bcl-xL (pM) | Bcl-2 (pM) | Bcl-w (pM) | SnCs $EC_{50}$ (µM) | SI |
| UM/APG-901 | BM-501 | 639.1 | NA | NA | NA | NA | NA |
| UM/APG-902 | BM-983 | 967.5 | 3307 | 4037 | >250000 | 5.000 | 1.0 |
| UM/APG-903 | BM-782 | 1274.4 | 885.55 | 10923 | 17694 | 11.000 | 1.3 |
| UM/APG-904 | BM-788 | 1348.2 | 5292 | 121045 | 23132.5 | NA | NA |
| UM/APG-905 | BM-792 | 1165.7 | 64.125 | 3324 | 1295.5 | 1.000 | 3.3 |
| UM/APG-906 | BM-957 | 1179.7 | 45.3 | 3333 | 659.95 | 0.300 | 11.7 |
| UM/APG-907 | BM-962 | 1193.7 | 57.41 | 3389.5 | 538.15 | 0.200 | 18.5 |
| UM/APG-908 | BM-1075 | 1113.7 | 5.7285 | 178.95 | 161.45 | 0.300 | 15.3 |
| UM/APG-909 | BM-1192 | 1215.3 | NA | NA | NA | 0.050 | 60.0 |
| UM/APG-910 | BM-1195 | 1229.3 | 148.565 | 666.55 | 174.7 | 0.006 | 128.7 |
| UM/APG-911 | BM-1197 | 1245.8 | 295 | 447.95 | 291.6 | 0.005 | 366.7 |
| UM/APG-912 | BM-1244 | 1273.8 | 134.52 | 450.75 | 356.75 | 0.300 | 66.7 |
| UM/APG-913 | BM-1261 | 1409.9 | 106.89 | 274.45 | 239.45 | 27.000 | NA |
| UM/APG-914 | BM-1252 | 1395.9 | 81.085 | 135.85 | 123.95 | 6.000 | NA |

The data show that binding to any of the Bcl isoforms with high affinity was not necessarily predictive of an effective senolytic agent. The compounds designated BM-1075, BM-1195, BM-1197, BM-1244, BM-1261, and BM-1252 all had binding affinities (Ki) for the Bcl isoforms that were in the nanomole to picomole range. However, in the assay to determine effective concentration for killing the cells ($EC_{50}$), some of these molecules, such as BM-1244, BM-1261, and BM-125, were 60 to 5,000-fold less potent than the compounds ultimately chosen for development.

The compounds with the best senolytic activity, BM-1195 and BM-1197, were potent in the nanomole range. There was a wide range of specificity for senescent cells (SI) determined for the various compounds, ranging from 1.0 (non-specific) to over 300. The best compound in terms of both potency and specificity was BM-1197, with BM-1195, BM-1244, BM-1105, and BM-1075 also being of interest.

In accordance with the data, the following deductions were made with respect to the chemical structure. This substructure was at the core of effective compounds:

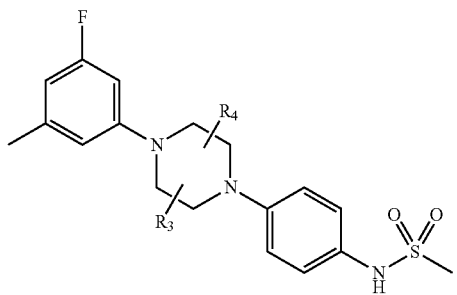

with the $R_3$, $R_4$, and F groups being optional. The —$SO_2CF_3$ in BM-1197 is influential, but could be substituted with groups having similar properties, such as —$NO_2$ in BM-1075. The —$SO_2R'$ group is influential, although R' could be varied from —$CH_3$ to other short-chain alkyl groups. The aryl —S—$C_6H_5$ group is also influential, although it could potentially have neutral substituents. With respect to the following part of the structure:

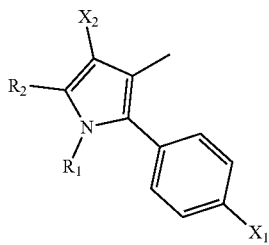

$R_1$ can be several short-chain alkyl groups, and $X_1$ can be varied (Cl in BM-1197; F in BM-1195). The following part of BM-1197:

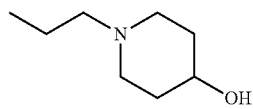

appears to be forgiving in form, with a range of alternative substructures being effective for many purposes of this invention.

These and other deductions lead to the drawing of the generic structure shown earlier as Formula VI and Formula VII.

Example 4: Effect of Senolytic Agents on Senescent Retinal Vascular Cells

The ability of candidate agents to eliminate senescent cells or senescent-like retinal endothelial cells was measured directly in the following assay.

Human retinal microvascular endothelial cells (HRMEC) were obtained from Neuromics with the designation HEC09. The cells were initially maintained and propagated at <75% confluency in ENDO-Growth Media (Neuromics, Edina Minn.) at 3% O2, 10% CO2, and ~95% humidity. The cells were divided into three groups: irradiated cells (cultured for 7 days after irradiation prior to use), proliferating normal cells (cultured at low density for one day prior to use), and quiescent cells (cultured to confluency over 4 days).

On day 0, the irradiated cells were prepared as follows, HRMEC cells were covered with 3 mL of TrypLE trypsin-containing reagent (Thermofisher Scientific, Waltham, Mass.) and incubated for 5 min until the cells rounded up and began to detach from the plate. Cells were dispersed, counted, and prepared in medium at a concentration of 100,000 cells per mL. This cell suspension was placed in T175 flasks at a density of 100,000 cells per mL and irradiated at 10-15 Gy. Following irradiation, the cells were plated at 100 µL in 96-well plates. On days 1, 3, 6, the medium in each well was aspirated and replaced with fresh medium.

On day 3, the quiescent healthy cells were prepared as follows. Healthy, non-senescent HRMEC cells were released from the culture flask by incubation with 3 mL of TrypLE trypsin-containing reagent (Thermofisher Scientific, Waltham, Mass.) and incubated for 5 min until the cells rounded up and began to detach from the plate. Cells were dispersed, counted, and prepared in medium at a concentration of 80,000 cells per mL. 100 µL of the cells was plated in each well of a 96-well plate. Medium was changed on days 1, 3, 6, and 10.

On day 6, the proliferating healthy cell population as prepared as follows. Healthy non-senescent HRMEC cells were washed, covered with 3 mL of TrypLE and cultured for 5 minutes until the cells rounded up and began to detach from the plate. Cells were dispersed, counted, and prepared in medium at a concentration of 40,000 cells per mL. 100 µL of the cells was plated in each well of a 96-well plate.

On day 7, candidate senolytic agents were combined with the cells as follows. A DMSO dilution series of each test compound was prepared at 200 times the final desired concentration in a 96-well PCR plate. Immediately before use, the DMSO stocks were diluted 1:200 into prewarmed complete medium. Medium was aspirated from the cells in each well, and 100 µL/well of the compound containing medium was added.

The candidate senolytic agents were cultured with the cells for 3 days. The assay system used the properties of a thermostable luciferase to enable reaction conditions that generate a stable luminescent signal while simultaneously inhibiting endogenous ATPase released during cell lysis. At the end of the culture period, the plates were removed from the incubator and allowed to equilibrate at room temperature for 20 minutes then 100 µL of CellTiter-Glo® reagent (Promega Corp., Madison, Wis.) was added to each of the wells. The cell plates were placed for 30 seconds on an orbital shaker and then allowed to stand at room temperature for 10 minutes before measuring luminescence. The luminescence readings were normalized to determine % cell survival/growth and plotted against test compound concentrations, and potencies ($IC_{50}$ values) were determined by non-linear curve fitting in Graphpad Prism®.

Figure 7:
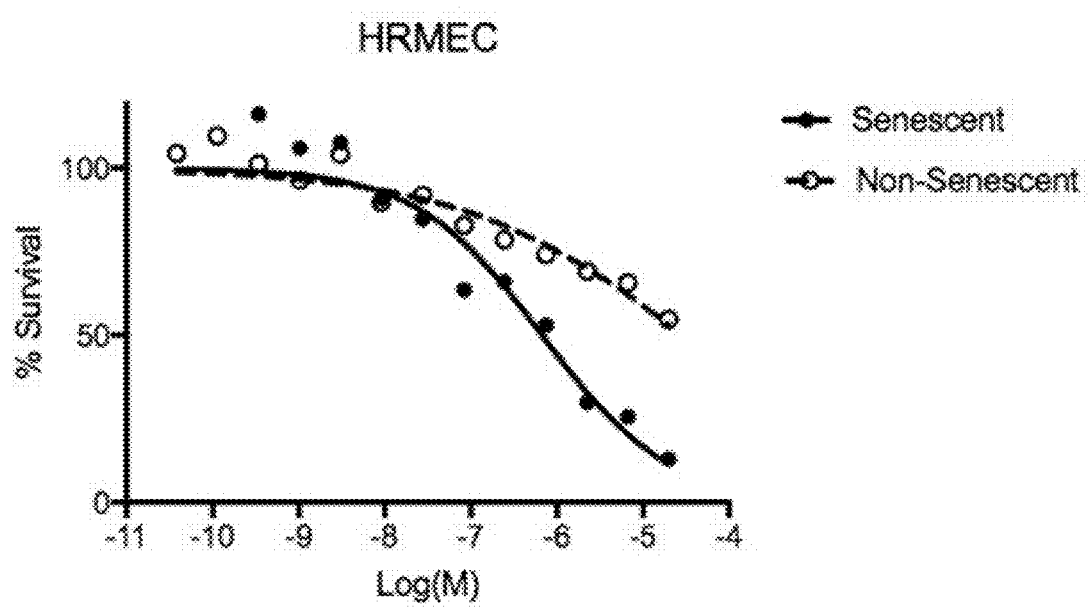
FIG. 7 is a concentration-response curve for senescent human retinal microvascular endothelial cells HRMEC cells and control cells treated in vivo with a senolytic agent.

FIG. 7 shows the results. The concentration-response curve for an example test compound, demonstrates sensitivity of senescent HRMEC cell survival to incubation with a senolytic molecule. These data show that senolytic agents are capable of eliminating senescent HRMEC cells in culture.

Example 5: Effect of Senolytic Agents on Senescent Cells from the Eye

The ability of candidate agents to eliminate senescent cells or senescent-like cells was measured directly in the following assay.

Human retinal pigmented epithelial (RPE) cells were obtained from Lonza with the designation 194987. The cells were initially maintained and propagated at <75% confluency in RPE media defined by Sonoda et al. in 2009 with 5% FBS and Pen/Strep in an atmosphere of 3% O2, 10% CO2, and ~95% humidity. The cells were divided into three groups: irradiated cells (cultured for 12 days after irradiation prior to use), proliferating normal cells (cultured at low density for two day prior to use), and quiescent cells (cultured to confluency over 12 days).

On day 0, the irradiated cells were prepared as follows, RPE cells were covered with 3 mL of TrypLE trypsin-containing reagent (Thermofisher Scientific, Waltham, Mass.) and incubated for 5 min until the cells rounded up and began to detach from the plate. Cells were dispersed, counted, and prepared in medium at a concentration of 100,000 cells per mL. This cell suspension was placed in T175 flasks at a density of 100,000 cells per mL and irradiated at 10-15 Gy. Following irradiation, the cells were plated at 100 µL in 96-well plates. On days 1, 3, 6, and 10 the medium in each well was aspirated and replaced with fresh medium.

On day 0, the quiescent healthy cells were prepared as follows. Healthy, non-senescent RPE cells were released from the culture flask using trypsin, covered with 3 mL of TrypLE trypsin-containing reagent (Thermofisher Scientific, Waltham, Mass.) and incubated for 5 min until the cells rounded up and began to detach from the plate. Cells were dispersed, counted, and prepared in medium at a concentration of 100,000 cells per mL. 100 µL of the cells was plated in each well of a 96-well plate. Medium was changed on days 1, 3, 6, and 10.

On day 10, the proliferating healthy cell population as prepared as follows. Healthy non-senescent RPE cells were washed, covered with 3 mL of TrypLE and cultured for 5 minutes until the cells rounded up and began to detach from the plate. Cells were dispersed, counted, and prepared in medium at a concentration of 30,000 cells per mL. 100 µL of the cells was plated in each well of a 96-well plate.

On day 12, candidate senolytic agents were combined with the cells as follows. A DMSO dilution series of each test compound was prepared at 200 times the final desired concentration in a 96-well PCR plate. Immediately before use, the DMSO stocks were diluted 1:200 into prewarmed complete medium. Medium was aspirated from the cells in each well, and 100 L/well of the compound containing medium was added.

The candidate senolytic agents were cultured with the cells for 3 days. The assay system used the properties of a thermostable luciferase to enable reaction conditions that generate a stable luminescent signal while simultaneously inhibiting endogenous ATPase released during cell lysis. At the end of the culture period, the plates were removed from the incubator and allowed to equilibrate at room temperature for 20 minutes then 100 µL of CellTiter-Glo® reagent (Promega Corp., Madison, Wis.) was added to each of the wells. The cell plates were placed for 30 seconds on an orbital shaker and then allowed to stand at room temperature for 10 minutes before measuring luminescence. The luminescence readings were normalized to determine % cell survival/growth and plotted against test compound concentrations, and potencies ($IC_{50}$ values) were determined by non-linear curve fitting in Graphpad Prism.

FIG. 8 shows the results. The concentration-response curve for an example test compound, demonstrates sensitivity of senescent RPE cell survival to incubation with a senolytic molecule. In contrast, the $IC_{50}$ for proliferating, non-senescent RPE is higher than that determined for the senescent cells. These data show that senolytic agents are capable of eliminating senescent RPE cells in culture.

Example 6: Efficacy of Compounds in an Animal Model of Ischemic Retinopathy

The efficacy of model compound UBX1967 was studied in the mouse oxygen-induced retinopathy (OIR) model, which provides an in vivo model of retinopathy of prematurity (ROP) and diabetic retinopathy.

C57B1/6 mouse pups and their CD1 foster mothers were exposed to a high oxygen environment (75% O2) from postnatal day 7 (P7) to P12. At P12, animals were injected intravitreally with 1 µl test compound (200, 20, or 2 uM) formulated in 1% DMSO, 10% Tween-80, 20% PEG-400, and returned to room air until P17. Eyes were enucleated at P17 and retinas dissected for either vascular staining or qRT-PCR. To determine avascular or neovascular area, retinas were flatmounted, and stained with isolectin B4 (IB4) diluted 1:100 in 1 mM $CaCl_2$. For quantitative measurement of senesecence markers (e.g., Cdkn2a, Cdkn1a, 116, Vegfa), qPCR was performed. RNA was isolated and cDNA was generated by reverse-transcription, which was used for qRT-PCR of the selected transcripts.

FIGS. 9A and 9B show that intravitreal (IVT) administration UBX1967 resulted in statistically significant improvement in the degree of neovascularization and vaso-obliteration at all dose levels.

Figure 10A:
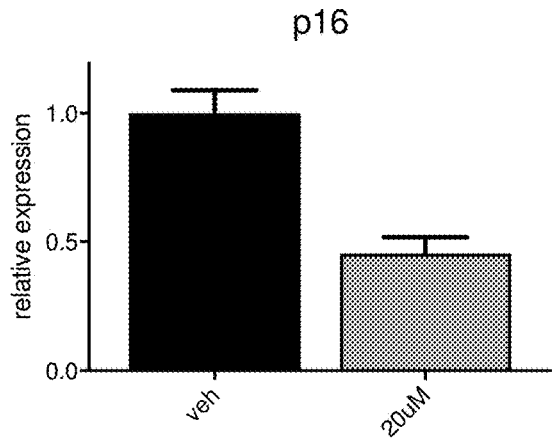
Figure 10B:
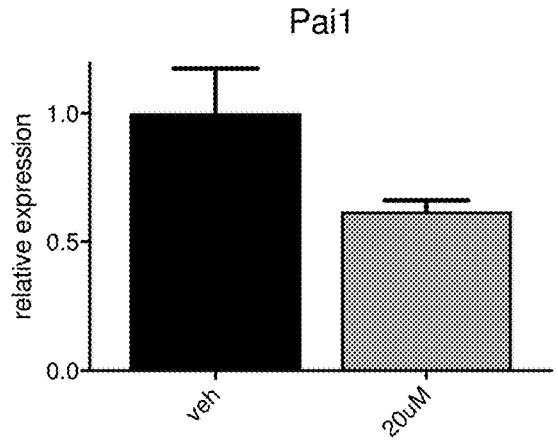
Figure 10C:
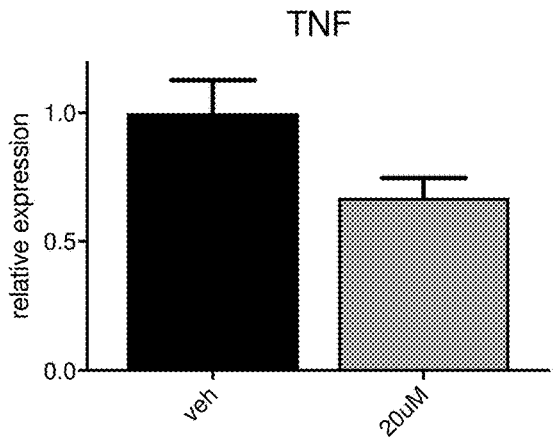
Figure 10D:
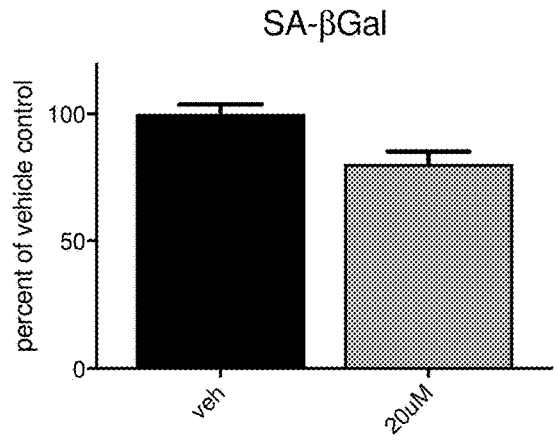

FIGS. 10A and 10B show the relative abundance of several transcripts associated with senescence (p16, pai1) and human disease (vegf). Treatment with UBX1967 resulted in a 58%, 35%, and 24% reduction in p16, pai1, and vegf, respectively. Senescence-associated β-galactosidase (SA-BGal) activity was reduced by 17% after administration of UBX1967.

These results show that a single ocular injection of UBX1967 can functionally inhibit pathogenic angiogenesis and promote vascular repair in this key OIR disease model. We believe that efficacy of UBX1967 in the OIR model is due to elimination of senescent cells and accompanying SASP that propagates senescence in retinal cells and promotes neovascularization of retinal vessels.

Example 7: Efficacy of Compounds in an Animal Model of Diabetes Induced Retinopathy The efficacy of UBX1967 was studied in a mouse model of diabetic retinopathy, by a single administration of streptozotocin (STZ).

C57BL/6J mice of 6- to 7-week were weighted and their baseline glycemia was measured (Accu-Chek, Roche). Mice were injected intraperitoneally with STZ (Sigma-Alderich, St. Lois, Mo.) for 5 consecutive days at 55 mg/Kg. Age-matched controls were injected with buffer only. Glycemia was measured again a week after the last STZ injection and mice were considered diabetic if their non-fasted glycemia was higher than 17 mM (300 mg/dL). STZ treated diabetic C57BL/6J mice were intravitreally injected with 1 l of UBX1967 (2 µM or 20 µM, formulated as a suspension in 0.015% polysorbate-80, 0.2% Sodium Phosphate, 0.75% Sodium Chloride, pH 7.2) at 8 and 9 weeks after STZ administration. Retinal Evans blue permeation assay was performed at 10 weeks after STZ treatment.

FIGS. 11A and 11B show preliminary results for this protocol. Retinal and choroidal vascular leakage after intra-vitreal (IVT) administration UBX1967 improved in vascular permeability at both dose levels.

Example 8: Efficacy of Compounds in an Animal Model of Glaucoma

Administration of bleomycin, a DNA damaging agent, to the anterior chamber of the mouse or rabbit eye leads to cellular senescence, as detected by the induction of p16 transcript in the trabecular meshwork.

To induce a senescent phenotype in the trabecular meshwork in vivo, C57Bl/6 mice (aged 8 to 10 weeks) were injected intracamerally with 2 µL of 0.0075 U bleomycin sulfate. In the rabbit, 30 µL of 0.0075 U bleomycin sulfate were injected intracamerally in New Zealand white rabbits. Eyes were enucleated 14 days post-bleomycin injury and TM-enriched samples were micro-dissected. To determine change in senescent cells, RNA was isolated from TM and qPCR analysis was done to assess the effect of bleomycin on p16 mRNA levels.

FIGS. 12A and 12B show elevated relative expression of p16 at 14 days after intracameral (IC) injection of bleomycin in the right (OD) eye relative to the PBS-injected left (OS) eye of the test animals. This model can also be used to assess whether a test compound is pharmacologically capable of reducing or ameliorating the increased intraocular pressure that is a hallmark of primary open angle glaucoma (POAG).

Example 9: Senescent Cells in the Trabecular Meshwork of Tissue Samples from Humans Having POAG To obtain evidence for the presence of senescent cells in human patients having primary open angle glaucoma (POAG), tissue samples obtained from affected patents were stained for p16, a marker of senescent cells.

Donor globes were procured prospectively from eye banks and placed immediately into Davidson's reagent to fix for at least 48 hours. After fixation, the solution was exchanged for 70% ethanol. Tissue was then placed in histology cassettes and processed for paraffin infiltration and embedding. Paraffin blocks were mounted on a microtome and sectioned to 5-9 µm thickness. Cut tissue sections were placed into a 45° C. water bath, and Superfrost Plus™ microscope slides were used to pick up sections, wicking away excess water with a Kimwipe™ tissue. Slides were then placed upright to dry for 30 min at room temperature, followed by incubation overnight in a 37° C. incubator. Slides are baked for 15-20 min at 60° C. and then allowed to cool to room temperature.

Slides were dewaxed by incubation in BOND Dewaxing Solution at 70° C. for 30 s. Slides were then rehydrated by serial incubations in decreasing concentrations of ethanol as follows: twice in 100% ethanol for 5 min each, twice in 90% ethanol for 2 min each, twice in 75% ethanol for 2 min each, twice in 50% ethanol for 2 min each, and then rinsed under water for 4 min. Slides were then washed twice in Tris-buffered saline supplemented with 0.1% Triton-X 100 (TBST).

Antigen retrieval was performed by incubation in BOND ER1 solution (sodium citrate buffer, pH 6.0) at 95° C. for 20 min. Slides were incubated in 3% $H_2O_2$ for 10 min at room temperature, followed by washing twice in TBST.

Slides were incubated for 30 min at room temperature with p16 primary antibody (Roche, #9517), diluted 1:2 in TBST. After primary antibody incubation, slides were washed twice with TBST prior to incubation with the rabbit-anti-mouse secondary antibody for 20 min at room temperature. Slides were washed twice with TBST and incubated for 20 min at room temperature in HRP-conjugated secondary antibody. After antibody incubation, slides were washed twice with TBST and AEC chromogen was used for detection, prepared per manufacturer protocol, and color was allowed to develop for approximately 20 min. Slides were then rinsed three times in water, before incubation in Harris' hematoxylin for 20 s. Slides were washed thoroughly in water, and coverslips were applied to the slides over Vectashield™ mounting media (Vector Labs, Burlingame Calif.) and allowed to dry before imaging.

FIGS. 13A and 13B are representative images of p16 immunohistochemistry on human eye tissue obtained from donors diagnosed with POAG. Cells positive for expression of p16 appear with dark staining in the cells in and around the trabecular meshwork (circled area).

Example 10: Senescent Cells in Tissue from Humans with Age-Related Macular Degeneration (AMD)

To obtain evidence for the presence of senescent cells in AMD, tissue samples from affected patents were stained for p16.

Donor globes were procured prospectively from eye banks and placed immediately into Davidson's reagent to fix for at least 48 hours. After fixation, the solution was exchanged for 70% ethanol. Tissue was then placed in histology cassettes and processed for paraffin infiltration and embedding. Paraffin blocks were mounted on a microtome and sectioned to 5-9 µm thickness. Cut tissue sections were placed into a 45° C. water bath, and Superfrost Plus microscope slides were used to pick up sections, wicking away excess water with a Kimwipe. Slides were then placed upright to dry for 30 min at room temperature, followed by incubation overnight in a 37° C. incubator. Slides were baked for 15-20 min at 60° C. and then allowed to cool to room temperature. Slides were dewaxed using xylene or xylene substitute (e.g., Histoclear™) for 4 min, repeated for a total of 3 incubations. Slides were then rehydrated by serial incubations in decreasing concentrations of ethanol as follows: twice in 100% ethanol for 5 min each, twice in 90% ethanol for 2 min each, twice in 75% ethanol for 2 min each, twice in 50% ethanol for 2 min each, and then rinsed under water for 4 min.

Antigen retrieval was performed by incubation in acidic sodium citrate buffer at 120° C. for 3 min (or 95° C. for 20 min) using a steamer or pressure cooker. Slides were cooled to room temperature for 15 min following by washing twice in Tris-buffered saline supplemented with 0.1% Triton-X 100 (TBST) for 2 min each. Slides were washed twice again with TBST for 5 min each prior to blocking for 1 h at room temperature in TBST containing 5% normal serum, from the species of origin of the secondary antibody to be used. After blocking, the slides were drained and excess solution was wiped away. Slides were incubated overnight at 4° C. (or for 2 h at room temperature) with p16 primary antibody diluted 1:2 in TBST. After primary antibody incubation, slides were washed twice with TBST for 5 min each, then treated with 3% $H_2O_2$ in TBST for 15 min. Slides were then washed twice with TBST for 5 min each prior to secondary antibody incubation. Slides were incubated for 1 h at room temperature in HRP-conjugated secondary antibody. After antibody incubation, slides were washed three times with TBS for 5 min each. AEC chromogen was used for detection, prepared per manufacturer protocol, and color was allowed to develop for approximately 20 min. Slides were then rinsed in water for 5 min, before counterstaining with hematoxylin. Coverslips were applied to the slides over Vectashield mounting media (Vector Labs, Burlingame Calif.) and allowed to dry before imaging.

FIGS. 14A and 14B are representative images of p16 immunohistochemistry on human eye tissue obtained from donors diagnosed with AMD. Cells positive for expression of p16 appear with dark staining in areas with obvious disease pathology (circled area).

Example 11: Clinical Assessment

This example provides an outline for a pre-clinical or clinical trial to evaluate the safety and efficacy of a senolytic agent for the treatment of ophthalmic conditions.

The senolytic is administered to subjects in the trial by standard intravitreal (ITV) administration technique, with the eye washed and draped in usual sterile fashion following pre-injection IOP measurement. Topical anesthesia is applied and a lid speculum placed for adequate exposure. The injection quadrant is chosen by the treating physician, and a location for the injection measured at 3 to 4 mm posterior to the corneo-scleral limbus. A 28-32-gauge needle is used to administer a 0.05 mL to 0.1 mL injection of the compound. The lid speculum is removed at the conclusion of the injection procedure. Depending on the nature of the condition, potentially suitable intra- or peri-ocular delivery methods include intravitreal, intracameral, posterior juxtascleral, subconjunctival or suprachoroidal injection.

Following the treatment, subjects are evaluated to determine whether symptoms or signs of the ophthalmic condition are improved, relative to subjects in a control group, using commonly available tests of ocular structure and function (supra).

Example 12: Combination Therapy

This example illustrates the clinical use of a senolytic agent in combination with standard-of-care anti-VEGF therapy for VEGF-related ocular disease.

Subjects are recruited into the study that have wet AMD, and are already undergoing anti-VEGF therapy, or that have a need to initiate VEGF therapy. First administration of a senolytic compound is done on the same day as one of the regular administrations of anti-VEGF therapies. There are no expected contraindications to the use of ophthalmic therapies in conjunction with the senolytic compound. The senolytic agent is administered first by standard intravitreal (ITV) administration. Intraocular pressure (IOP) is measured at 15 and 30 minutes post-injection. When IOP is normalized to pre-injection levels, the anti-VEGF therapy (for example aflibercept 2.0 mg in 0.05 mL) is administered second. The eye is washed and draped in usual sterile fashion, as an entirely new sterile procedure from the first injection. Topical anesthesia is given and a lid speculum placed for adequate exposure. The injection quadrant is chosen by the treating physician, and a location for the injection measured at 3 to 4 mm posterior to the corneo-scleral limbus. A 28-32-gauge needle is used to administer a 0.05 mL injection of the compound. The lid speculum is removed at the conclusion of the injection. IOP is monitored at 5, 15 and 30 minutes following the second ITV injection.

Safety and efficacy of the combined treatment is assessed as follows. In the immediate post-injection period, the eye is monitored for any acute loss of vision or increase in intraocular pressure. At 30 minutes post-injection if vision and IOP are stable, the patient is discharged from the clinic under the standard post-procedure instructions of the treating physician. The patient is instructed to call immediately for the development of any change in vision or onset of pain or redness in the injected eye.

In the setting of this disease example of wet AMD, follow up evaluation is scheduled within one week to one month of treatment. Follow-up evaluation includes visual acuity and IOP measurement, monitoring for any improvement or decline since the therapy was administered. The anterior and posterior segment of the eye is examined and standard ancillary testing is performed, including but not limited to photography, IV fluorescein angiography and Optical Coherence Tomography (OCT).

Response to the senolytic is documented using this combination of clinical examination, functional and structural testing described above. Further follow-up is scheduled based on patient response. If the senolytic is given in conjunction with an anti-VEGF agent, the physician continues to follow the visit and treatment administration schedule associated with that agent.

REFERENCES

Acosta, J C et al. 2013. A Complex Secretory Program Orchestrated by the Inflammasome Controls Paracrine Senescence. Nature Cell Biology 15 (8). Nature Publishing Group: 978-90.
Moreno Menghini, Jacque L. Duncan. 2014. Diagnosis and ComplementaryExaminations in Cell-Based Therapy for Retinal Degenerative Disease. Casaroli-Marano R P, Zarbin M A (eds): Cell-Based Therapy for Retinal Degenerative Disease. Dev Ophthalmol. Basel, Karger, 2014, vol 53, pp 53-69.
Stein J D, Challa P. 2007. Mechanisms of action and efficacy of argon laser trabeculoplasty and selective laser trabeculoplasty. Curr Opin Ophthalmol. March; 18(2):140-5.
American Academy of Ophthalmology Retina/Vitreous Panel. 2014. Preferred Practice Pattern Guidelines. Posterior Vitreous Detachment, Retinal Breaks and Lattice Degeneration. San Francisco, Calif.
Bhisitkul R B et al. 2015. Macular atrophy progression and 7-year vision outcomes in subjects from the ANCHOR, MARINA, and HORIZON studies: the SEVEN-UP study. Am J Ophthalmol. May; 159(5):915-24.e2.
Levin L. 2005. Pathophysiology of the Progressive Optic Neuropathy of Glaucoma. Ophth Clin N Am. 18: 355-364.
Kozak I, Luttrull J K. 2015. Modern retinal laser therapy. Saudi J Ophthalmol. April-June; 29(2): 137-146.
Damji K F et al. 2006. Selective Laser Trabeculoplasty versus argon laser trabeculoplasty: results from a 1 year randomized clinical trial. Br J Ophthalmol. 90:1490-94.
Maguire M G et al. 2016. Five-Year Outcomes with Anti-Vascular Endothelial Growth Factor Treatment of Neovascular Age-Related Macular Degeneration: The Comparison of Age-Related Macular Degeneration Treatments Trials. Ophthalmology. August; 123(8):1751-6.

Holz F G et al. 2015. Multi-country real-life experience of anti-vascular endothelial growth factor therapy for wet age-related macular degeneration. Br J Ophthalmol; 99:220-6.

Kumar S and Fu Y. 2014. Age-related macular Degeneration: A Complex Pathology. Austin J Genet Genomic Res.; 1(1): 5.

Scott A and Fruttiger M. 2010. Oxygen-induced retinopathy: a model for vascular pathology in the retina. Eye. 24, 416-421

Oubaha M, Sapieha P et al. 2016. Senescence-associated secretory phenotype contributes to pathological angiogenesis in retinopathy. Sci Transl Med. October 26; 8(362): 362ra144.

Ito Y A et al. 2016. A Magnetic Microbead Occlusion Model to Induce Ocular Hypertension-Dependent Glaucoma in Mice. J Vis Exp. March 23; (109).

Almasieh M, Levin L A. 2017. Neuroprotection in Glaucoma: Animal Models and Clinical Trials. Annu Rev Vis Sci. September 15; 3:91-120. 061422. Epub 2017 Jul. 21.

Zhou, T, et al. 1998. Development of a multiple-drug delivery implant for intraocular management of proliferative vitreoretinopathy. Journal of Controlled Release 55: 281-295, 1998.

Osborne N N et al. Retinal ischemia: mechanisms of damage and potential therapeutic strategies. Prog Retin Eye Res. January; 23(1):91-147.

Ucuzian A A et al. 2010. Molecular Mediators of Angiogenesis. J Burn Care Res. 31(1):158 Campochiaro P A. 2015. Molecular pathogenesis of retinal and choroidal vascular diseases. Prog Retin Eye Res. November; 49:67-81.

Choi J1, Kook M S. 2015. Systemic and Ocular Hemodynamic Risk Factors in Glaucoma. Biomed Res Int.: 141905.

Wang H et al. The nerve growth factor signaling and its potential as therapeutic target for glaucoma. Biomed Res Int.:759473. Epub 2014 Aug. 31.

Caprioli, J. 2013. Glaucoma: A Disease of Early Cellular Senescence. Invest Ophthalmol Vis Sci. December 13; 54(14): ORSF 60-7.

Lutty G A. 2013. Effects of Diabetes on the Eye. Invest Ophthalmol Vis Sci. December 13; 54(14): ORSF 81-7.

Committee for the Classification of Retinopathy of Prematurity, 1984. Arch Ophthalmol. 102(8): 1130-1134.

Skowronska-Krawczyk D et al. Upregulation Mediated by SIX6 Defines Retinal Ganglion Cell Pathogenesis in Glaucoma. Mol Cell. September 17; 59(6):931-40

Li Lu, Zhao Y, Zhang H. 2017. P16INK4a upregulation mediated by TBK1 induces retinal ganglion cell senescence in ischemic injury. Cell Death Dis. April 20; 8(4): e2752

Matthaei M et al. 2014. Transcript profile of cellular senescence-related genes in Fuchs endothelial corneal dystrophy. Exp Eye Res. December; 129:13-17.

Man P Y W et al. 2002. Leber Hereditary Optic Neuropathy. J Med Genet; 39:162-169.

Dryja T P. 1986. 235: Retinitis Pigmentosa and Stationary Night Blindness. The Online Metabolic and Molecular Bases of Inherited Disease. DOI: 10.1036/ommbid.275

Kim J A et al. 2016. Enhanced Viral Replication by Cellular Replicative Senescence Immune Netw. October; 16(5): 286-295.

The several hypotheses presented in this disclosure provide a premise by way of which the reader may understand the invention. This premise is provided for the enrichment and appreciation of the reader. Practice of the invention does not require detailed understanding or application of the hypothesis. Except where stated otherwise, features of the hypothesis presented in this disclosure do not limit application or practice of the claimed invention. For example, except where the elimination of senescent cells is explicitly required, the compounds of this invention may be used for treating the conditions described regardless of their effect on senescent cells. Although many of the ophthalmic conditions referred to in this disclosure occur predominantly in older patients, the invention may be practiced on patients of any age having the condition indicated, unless otherwise explicitly indicated or otherwise required.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed.

The invention claimed is:

1. A method of promoting vascular repair in an eye of a subject in need thereof, comprising administering a therapeutically effective dose of a pharmaceutical composition comprising a compound selected from:

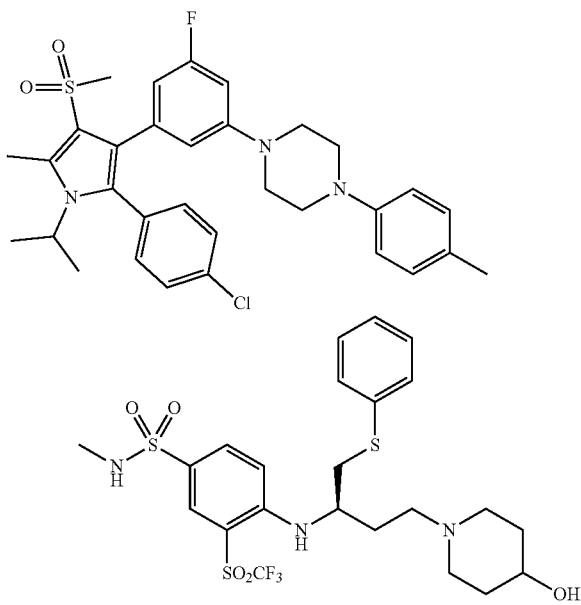

and phosphorylated forms and pharmaceutically acceptable salts thereof; and

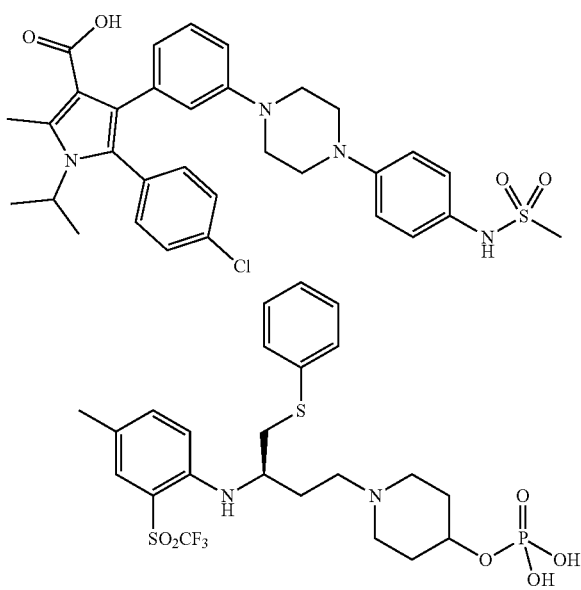

and pharmaceutically acceptable salts thereof.

2. The method of claim 1, wherein the promotion of vascular repair is a result of a reversal of neovascularization and/or vaso-obliteration in the eye.

3. The method of claim 1, wherein the compound is

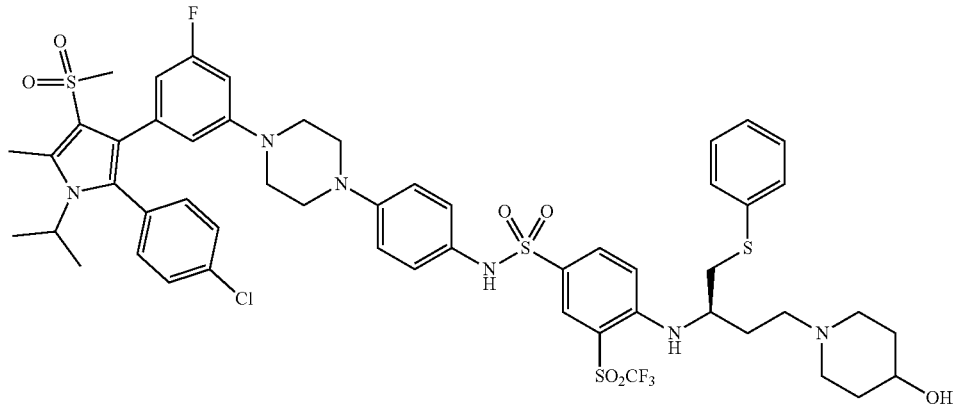

and phosphorylated forms and pharmaceutically acceptable salts thereof.

4. The method of claim 1, wherein the compound is

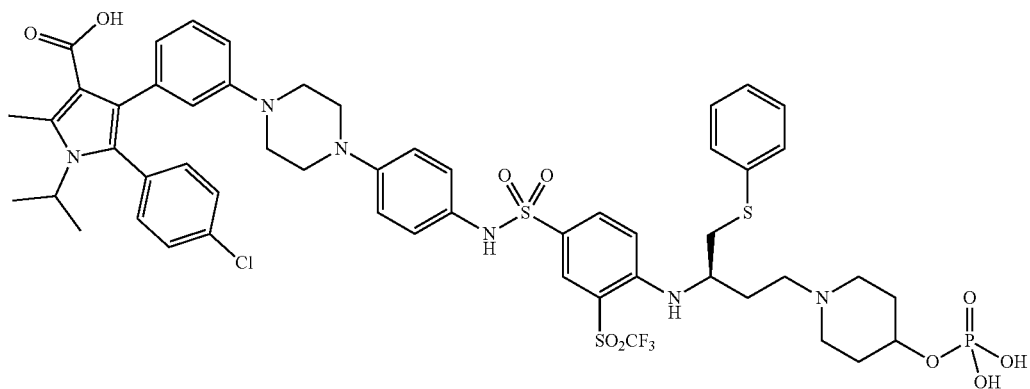

and pharmaceutically acceptable salts thereof.

5. The method of claim 1, wherein the pharmaceutical composition is administered intravitreally.

6. The method of claim 1, wherein the subject has diabetic retinopathy (DR), or has diabetic macular edema (DME), or has age-related macular degeneration (AMD), or has geographic atrophy (GA), or has retinopathy of prematurity (ROP).

* * * * *